(12) United States Patent
Horiguchi et al.

(10) Patent No.: US 11,370,740 B2
(45) Date of Patent: Jun. 28, 2022

(54) METHOD FOR PRODUCING ESTER GROUP-CONTAINING COMPOUND

(71) Applicant: DIC Corporation, Tokyo (JP)

(72) Inventors: Masahiro Horiguchi, Kitaadachi-gun (JP); Toru Tsuruta, Kitaadachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 16/079,293

(22) PCT Filed: Feb. 23, 2017

(86) PCT No.: PCT/JP2017/006767
§ 371 (c)(1),
(2) Date: Aug. 23, 2018

(87) PCT Pub. No.: WO2017/154588
PCT Pub. Date: Sep. 14, 2017

(65) Prior Publication Data
US 2019/0062256 A1 Feb. 28, 2019

(30) Foreign Application Priority Data
Mar. 10, 2016 (JP) .............................. JP2016-046961

(51) Int. Cl.
| | | |
|---|---|---|
| C07C 67/08 | (2006.01) | |
| C07D 277/82 | (2006.01) | |
| C09K 19/38 | (2006.01) | |
| C09K 19/54 | (2006.01) | |
| C09K 19/34 | (2006.01) | |
| C09K 19/32 | (2006.01) | |
| C07D 487/22 | (2006.01) | |
| C07D 493/04 | (2006.01) | |
| C08F 220/10 | (2006.01) | |
| G02B 5/30 | (2006.01) | |
| C09D 4/00 | (2006.01) | |
| C07D 213/30 | (2006.01) | |
| C07D 417/04 | (2006.01) | |
| C07C 69/757 | (2006.01) | |
| C07C 69/92 | (2006.01) | |
| C09K 19/04 | (2006.01) | |
| C08F 20/10 | (2006.01) | |
| C08L 33/06 | (2006.01) | |

(52) U.S. Cl.
CPC ............ *C07C 67/08* (2013.01); *C07C 69/757* (2013.01); *C07C 69/92* (2013.01); *C07D 213/30* (2013.01); *C07D 277/82* (2013.01); *C07D 417/04* (2013.01); *C07D 487/22* (2013.01); *C07D 493/04* (2013.01); *C08F 220/10* (2013.01); *C09D 4/00* (2013.01); *C09K 19/32* (2013.01); *C09K 19/322* (2013.01); *C09K 19/3486* (2013.01); *C09K 19/3491* (2013.01); *C09K 19/3497* (2013.01); *C09K 19/38* (2013.01); *C09K 19/54* (2013.01); *G02B 5/30* (2013.01); *C07C 2601/14* (2017.05); *C08F 20/10* (2013.01); *C08L 33/06* (2013.01); *C08L 2203/20* (2013.01); *C09K 2019/0448* (2013.01); *C09K 2019/3408* (2013.01); *Y02P 20/55* (2015.11)

(58) Field of Classification Search
None
See application file for complete search history.

(56) References Cited

FOREIGN PATENT DOCUMENTS

| | | |
|---|---|---|
| CN | 101838264 A | 9/2010 |
| CN | 107001242 A | 8/2017 |
| CN | 107108458 A | 8/2017 |
| CN | 107108473 A | 8/2017 |
| CN | 107108770 A | 8/2017 |
| CN | 107108775 A | 8/2017 |
| CN | 107207652 A | 9/2017 |
| CN | 107207676 A | 9/2017 |
| CN | 107209307 A | 9/2017 |
| CN | 108137486 A | 6/2018 |
| CN | 108290850 A | 7/2018 |
| CN | 108349925 A | 7/2018 |
| DE | 10146970 A1 | 4/2003 |
| JP | 53-84902 A | 7/1978 |
| JP | 2014-123134 A | 7/2014 |
| JP | 2016-17034 A | 2/2016 |

(Continued)

OTHER PUBLICATIONS

International Search Report dated May 23, 2017, issued in counterpart International Application No. PCT/JP2017/006767 (5 pages).
Ono et al., "δ-Lactone formation from δ-hydroxy-trans-α,β-unsaturated carboxylic acids accompanied by trans-cis isomerization: synthesis of (−)-tetra-O-acetylosmundalin", Tetrahedron 63 (2007), pp. 10140-10148, cited in the specification.

(Continued)

*Primary Examiner* — Sudhakar Katakam
*Assistant Examiner* — Jennifer C Sawyer
(74) *Attorney, Agent, or Firm* — WHDA, LLP

(57) ABSTRACT

The present invention provides a novel method for producing an ester group-containing compound and a derivative produced using the compound as a synthetic intermediate. The invention also provides a polymerizable composition containing the compound obtained by the production method and a film-shaped polymer obtained by polymerizing the polymerizable composition. The present invention is a method for producing an ester group-containing compound, the method including a mixing step of mixing a condensing agent, a Bronsted acid, a carboxylic acid, and a phenol or an alcohol to prepare a reaction mixture. The Bronsted acid selected is other than the condensing agent, the carboxylic acid, and the phenol.

2 Claims, No Drawings

(56) References Cited

FOREIGN PATENT DOCUMENTS

WO 2014/010325 A1 1/2014

OTHER PUBLICATIONS

Raju et al., "Alterntnate routes for the synthesis of ibuprofen piconol", Indian Journal of Chemistry, vol. 46B, Jan. 2007, pp. 170-172, cited in the specification.

Office Action dated Aug. 18, 2021, issued in counterpart CN application No. 201780008914.4, with English translation. (11 pages).

METHOD FOR PRODUCING ESTER GROUP-CONTAINING COMPOUND

TECHNICAL FIELD

The present invention relates to a method for producing an ester group-containing compound, to a derivative produced using the compound as a synthetic intermediate, to a polymerizable composition containing the compound, to a polymerizable liquid crystal composition containing the compound, and to an optically anisotropic body using the polymerizable liquid crystal composition.

BACKGROUND ART

Various methods for forming an ester group are known. A reaction using a condensing agent is widely used because the reaction proceeds mildly and its procedure is simple. However, the intended ester compound may not be obtained in high yield, depending on the types of substrates used. For example, when a compound having a carbodiimide structure is used as the condensing agent, a large amount of N-acylurea may be produced as a by-product. In such a case, disadvantageously, the step of removing the by-product is necessary, or a reduction in yield occurs (PTL 1, NPL1, and NPL 2). When an ester compound containing a trace amount of the by-product remaining therein is used for a liquid crystal material or an optical film, image-sticking may occur on a liquid crystal display, or the heat resistance and lightfastness of the film deteriorate. There is therefore a need to develop an ester group formation method in which a lesser amount of N-acylurea is produced as a by-product.

CITATION LIST

Patent Literature

PTL 1: DE10146970A1

Non Patent Literature

NPL 1: Tetrahedron, 2007, Vol. 63, No. 41, pp. 10140-10148
NPL 2: Indian Journal of Chemistry, Section B: Organic Chemistry Including Medicinal Chemistry, 2007, Vol. 46B, No. 1, pp. 170-172

SUMMARY OF INVENTION

Technical Problem

The present invention provides a novel method for producing an ester group-containing compound and a compound produced using the above compound as a synthetic intermediate. The invention also provides a polymerizable composition that contains the compound obtained by the above production method or a derivative of the compound and is useful to produce a polymer excellent in heat resistance and lightfastness. The invention also provides a polymer obtained by polymerizing a polymerizable composition containing the compound obtained by the above production method or a derivative of the compound and also provides an optically anisotropic body using the polymer.

Solution to Problem

To achieve the above object, the present inventor have conducted extensive studies and succeeded in developing a novel method for producing an ester group-containing compound. Specifically, the present invention provides a method for producing an ester group-containing compound, the method including a mixing step of mixing a condensing agent, a Bronsted acid, a carboxylic acid, and a phenol or an alcohol to prepare a reaction mixture, wherein the Bronsted acid selected is other than the condensing agent, the carboxylic acid, and the phenol. Moreover, the invention provides: a derivative produced using the compound as a synthetic intermediate; a composition containing the compound; a resin, a resin additive, an oil, a filter, an adhesive, a glue, a fat, an ink, a medicine, a cosmetic, a detergent, a building material, a packaging material, a liquid crystal material, an organic EL material, an organic semiconductor material, an electronic material, a display element, an electronic device, a communication device, an automobile component, an aircraft component, a mechanical component, an agricultural chemical, and a food product that use the compound; a product that uses any of them; a polymerizable liquid crystal composition using the compound; a polymer obtained by polymerizing the polymerizable liquid crystal composition; and an optically anisotropic body using the polymer.

Advantageous Effects of Invention

With the production method of the present invention, the ester group-containing compound can be obtained in high yield. In the optically anisotropic body using the polymerizable liquid crystal composition containing the compound produced by the production method of the present invention, deterioration of heat resistance and lightfastness after irradiation with UV light for a long time is less likely to occur, and therefore the compound produced by the production method of the present invention is useful for optical material applications such as optical compensation films.

DESCRIPTION OF EMBODIMENTS

The present invention provides a method for producing an ester group-containing compound, a derivative produced using the compound as a synthetic intermediate, and a composition containing the compound or the derivative thereof. The invention also provides: a resin, a resin additive, an oil, a filter, an adhesive, a glue, a fat, an ink, a medicine, a cosmetic, a detergent, a building material, a packaging material, a liquid crystal material, an organic EL material, an organic semiconductor material, an electronic material, a display element, an electronic device, a communication device, an automobile component, an aircraft component, a mechanical component, an agricultural chemical, and a food product that use the compound; and a product that uses any of them. The invention also provides a polymerizable liquid crystal composition, a polymer obtained by polymerizing the polymerizable liquid crystal composition, and an optically anisotropic body using the polymer.

The production method of the present invention includes a mixing step of mixing a condensing agent, a Bronsted acid, a carboxylic acid, and a phenol or an alcohol to produce a reaction mixture. In the mixing step, the Bronsted acid selected is other than the condensing agent, the carboxylic acid, and the phenol.

By allowing the condensation reaction of the carboxylic acid with the phenol or alcohol to proceed in the reaction mixture obtained in the mixing step, the formation of a by-product is reduced, and the ester group-containing compound can be obtained in high yield. The production method of the present invention includes an esterification step of forming the ester group-containing compound through the condensation reaction of the carboxylic acid with the phenol or alcohol in the reaction mixture. It is not always necessary to provide the esterification step separately from the mixing step, and the esterification step may be completed together with the completion of the mixing step.

In the mixing step, it is preferable to prepare the reaction mixture by further mixing a base. By allowing the condensation reaction to proceed in the presence of the base, the yield of the ester group-containing compound and its reaction rate can be increased.

In the mixing step, it is preferable from the viewpoint of availability, yield, and reaction rate that the condensing agent is a compound having a structure selected from carbodiimide, imidazole, triazine, phosphonium, uronium, and azodicarboxylic acid, and it is particularly preferable that the condensing agent is a compound having a carbodiimide structure. Specific examples include 1-cyclohexyl-3-(2-morpholinoethyl)carbodiimide metho-p-toluenesulfonate, N-cyclohexylcarbodiimidomethyl polystyrene resin, N,N'-diisopropylcarbodiimide, N,N'-dicyclohexylcarbodiimide, 1-(3-dimethylaminopropyl)-3-ethylcarbodiimide hydrochloride, 1-(3-dimethylaminopropyl)-3-ethylcarbodiimide resin, and 1-(3-dimethylaminopropyl)-3-ethylcarbodiimide. From the viewpoint of availability, cost, and degeneration resistance of a film prepared using as a raw material the ester group-containing compound or its derivative, the condensing agent is preferably a compound selected from N-cyclohexylcarbodiimidomethyl polystyrene resin, N,N'-diisopropylcarbodiimide, N,N'-dicyclohexylcarbodiimide, 1-(3-dimethylaminopropyl)-3-ethylcarbodiimide resin, and 1-(3-dimethylaminopropyl)-3-ethylcarbodiimide, more preferably a compound selected from N,N'-diisopropylcarbodiimide, N,N'-dicyclohexylcarbodiimide, and 1-(3-dimethylaminopropyl)-3-ethylcarbodiimide, and still more preferably a compound selected from N,N'-diisopropylcarbodiimide and N,N'-dicyclohexylcarbodiimide. From the viewpoint of ease of handling, the condensing agent is particularly preferably N,N'-diisopropylcarbodiimide.

In the mixing step, the base is preferably an aromatic amine from the viewpoint of yield and reaction rate, more preferably an aromatic amine having a six-membered ring and/or a five-membered ring, and still more preferably an aromatic amine having a structure selected from isoxazole, isothiazole, imidazole, oxadiazole, oxazole, thiadiazole, thiazole, tetrazole, triazole, pyrazole, indazole, pyrrole, indole, carbazole, carboline, tetrazine, triazine, pyrazine, pyridine, quinoline, isoquinoline, acridine, pyridazine, phthalazine, pyrimidine, quinazoline, purine, and/or pteridine. From the viewpoint of availability and cost, the base is particularly preferably an aromatic amine having a pyridine structure. Specific examples include pyridine, 4-dimethylaminopyridine, 2,4,6-trimethylpyridine, and 4-pyrrolidinopyridine.

In the esterification step, the Bronsted acid in the reaction mixture may be in the form of a free acid or may be in the form of a salt or complex. From the viewpoint of yield and reaction rate, it is preferable that the Bronsted acid is in the form of a free acid. It is also preferable that protons are dissociated from at least part of the Bronsted acid in the reaction mixture. In the esterification step, it is preferable that the content of water in the reaction mixture is small. For example, the content of water in the reaction system is preferably 10 molar equivalents or less relative to the condensing agent, more preferably 1 molar equivalent or less relative to the condensing agent, still more preferably 0.5 molar equivalents or less relative to the condensing agent, yet more preferably 0.1 molar equivalents or less relative to the condensing agent, and particularly preferably 0.01 molar equivalents or less relative to the condensing agent. To reduce the content of water in the reaction system, a desiccant, a dehydrator, and/or a water absorbent may be used. For example, silica gel, alumina, activated carbon, sodium sulfate, magnesium sulfate, a molecular sieve, or a water-absorbing polymer may be used.

When the Bronsted acid is an inorganic acid, specific examples of the Bronsted acid include hydrofluoric acid, hydrochloric acid, hydrobromic acid, nitric acid, phosphoric acid, sulfuric acid, and boric acid. When the Bronsted acid is an organic acid, examples of the Bronsted acid include carboxylic acids, sulfonic acids, sulfinic acids, phosphoric acids, polyphosphoric acids, and boric acids. From the viewpoint of ease of handling and yield, the Bronsted acid is preferably an inorganic acid, a sulfonic acid, or a sulfinic acid and particularly preferably hydrochloric acid, sulfuric acid, a sulfonic acid, or a sulfinic acid. Specific examples include hydrochloric acid, sulfuric acid, fluorosulfonic acid, chlorosulfonic acid, methanesulfonic acid, trifluoromethanesulfonic acid, 2-aminoethanesulfonic acid, 2-[4-(2-hydroxyethyl)-1-piperazinyl]ethanesulfonic acid, 3-morpholinopropanesulfonic acid, piperazine-1,4-bis(2-ethanesulfonic acid), 10-camphorsulfonic acid, benzenesulfonic acid, p-toluenesulfonic acid, 4-chlorobenzenesulfonic acid, sulfanilic acid, 3-pyridinesulfonic acid, 2-aminoethanesulfinic acid, benzenesulfinic acid, and 4-methylbenzenesulfinic acid. However, when the condensing agent used in the mixing step is a Bronsted acid or contains a Bronsted acid, a Bronsted acid different from the condensing agent is selected.

From the viewpoint of increasing the yield of the ester group-containing compound, the amount of the Bronsted acid added in the mixing step is preferably 0.0001 molar equivalents to 100 molar equivalents relative to the condensing agent, more preferably 0.001 molar equivalents to 10 molar equivalents relative to the condensing agent, still more preferably 0.01 molar equivalents to 1 molar equivalent relative to the condensing agent, and particularly preferably 0.05 molar equivalents to 0.5 molar equivalents relative to the condensing agent. In the mixing step, when the Bronsted acid and also the base are present in a solution serving as the reaction mixture, no particular limitation is imposed on the amount of the Bronsted acid added, so long as the Bronsted acid is present in the form of a free acid. However, when the molar amount of the Bronsted acid added is excessively smaller than the molar amount of the base, the molar amount of the dissociated Bronsted acid in the solution mixture is small, and therefore the amount of N-acylurea formed is large. When the molar amount of the Bronsted acid added is excessively larger than the molar amount of the base, the amount of the dissociated Bronsted acid in the solution is large. However, since post-reaction treatment may be complicated and other by-products may be formed, the yield of the intended ester group-containing compound decreases. Therefore, the amount of the Bronsted acid added is preferably 0.001 molar equivalents to 1,000 molar equivalents relative to the base, more preferably 0.01 molar equivalents to 100 molar equivalents relative to the base, still more preferably 0.1 molar equivalents to 10 molar equivalents relative to the condensing agent, and particularly preferably 0.5 molar equivalents to 5 molar equivalents. From the viewpoint of reducing the amount of the Bronsted acid used, it is preferable that the base selected is other than Bronsted bases.

In the mixing step, when the reaction mixture is prepared, it is preferable from the viewpoint of yield and ease of operation that the phenol or alcohol, the carboxylic acid, the base, the Bronsted acid, and the condensing agent are added such that, after the Bronsted acid is added, the condensing agent is added. Specific procedures are as follows. For example, it is preferable that the condensing agent is added to a solution containing the Bronsted acid and any of the above components. More preferably, the condensing agent is added to a solution containing the Bronsted acid and at least the phenol or alcohol. Still more preferably, the condensing agent is added to a solution containing the Bronsted acid and at least the phenol or alcohol and the base. Particularly preferably, the condensing agent is added to a solution containing the Bronsted acid and at least the phenol or alcohol, the carboxylic acid, and the base.

No particular limitation is imposed on the components contained in the reaction mixture and the contents of the components etc., so long as the reaction mixture is prepared by mixing the phenol or alcohol, the carboxylic acid, the base, the Bronsted acid, and the condensing agent. The reaction mixture contains the phenol or alcohol, the carboxylic acid, the base, the Bronsted acid, and the condensing agent and may further contain any additional component that is not derived from these components. The additional component may be, for example, a reaction solvent. From the viewpoint of ease of handling, the reaction mixture is preferably in the form of a dispersion or solution.

In the production method of the present invention, no particular limitation is imposed on the carboxylic acid used and the phenol or alcohol used, and the following compounds can be shown as examples.

The carboxylic acid is preferably a compound represented by the following general formula (a-1):

[Chem. 1]

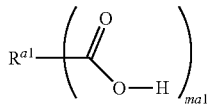

(a-1)

(wherein $R^{a1}$ represents a hydrogen atom or an organic group having 1 to 1,000 carbon atoms; ma1 represents an integer from 1 to 20; and, when ma2 in general formula (a-2) below is an integer other than 1, ma1 represents 1). From the viewpoint of obtaining a preferred ester group-containing compound described later, ma1 preferably represents an integer from 0 to 4, more preferably represents an integer from 1 to 3, and still more preferably represents an integer of 1 or 2.

The phenol or alcohol is preferably a compound represented by the following general formula (a-2):

[Chem. 2]

$R^{a2}\!-\!\!\!-\!\!(O\!-\!H)_{ma2}$ (a-2)

(wherein $R^{a2}$ represents an organic group having 1 to 1,000 carbon atoms; ma2 represents an integer from 1 to 20; and, when ma1 in general formula (a-1) above is an integer other than 1, ma2 represents 1). From the viewpoint of obtaining a preferred ester group-containing compound described later, ma1 preferably represents an integer from 0 to 4, more preferably represents an integer from 1 to 3, and still more preferably represents 1 or 2.

The ester group-containing compound is preferably a compound represented by the following general formula (a-3-1) or general formula (a-3-2):

[Chem. 3]

(a-3-1)

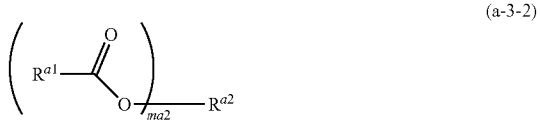

(a-3-2)

(wherein $R^{a1}$ and $R^{a2}$ have the same meanings as above; when ma1 in general formula (a-1) above is an integer other than 1, the ester group-containing compound is a compound represented by general formula (a-3-1); and, when ma2 in general formula (a-2) above is an integer other than 1, the ester group-containing compound is a compound represented by general formula (a-3-2)). When ma1 and ma2 both are an integer of 1, the ester group-containing compound is represented by general formula (a-3-1).

Preferably, the carboxylic acid and the phenol or alcohol are selected such that a preferred ester group-containing compound described later is obtained by the production method of the invention. In this case, $R^{a1}$ and $R^{a2}$ may be determined according to formula (a-3-1) or formula (a-3-2) on the basis of the structure of the intended ester group-containing compound.

More specifically, the carboxylic acid is preferably a compound represented by the following general formula (a-1-1) or general formula (a-1-2):

[Chem. 4]

(a-1-1)

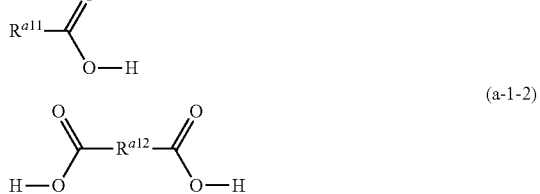

(a-1-2)

(wherein $R^{a11}$ represents a hydrogen atom or a monovalent organic group having 1 to 100 carbon atoms, and $R^{a12}$ represents a divalent organic group having 1 to 100 carbon atoms). The phenol or alcohol is preferably a compound represented by the following general formula (a-2-1) or general formula (a-2-2):

[Chem. 5]

$R^{a21}\!-\!O\!-\!H$ (a-2-1)

$H\!-\!O\!-\!R^{a22}\!-\!O\!-\!H$ (a-2-2)

(wherein $R^{a21}$ represents a hydrogen atom or a monovalent organic group having 1 to 100 carbon atoms, and $R^{a22}$ represents a divalent organic group having 1 to 100 carbon atoms). The ester group-containing compound is preferably a compound represented by the following general formula (a-3-1-1), formula (a-3-2-1), or general formula (a-3-1-2):

[Chem. 6]

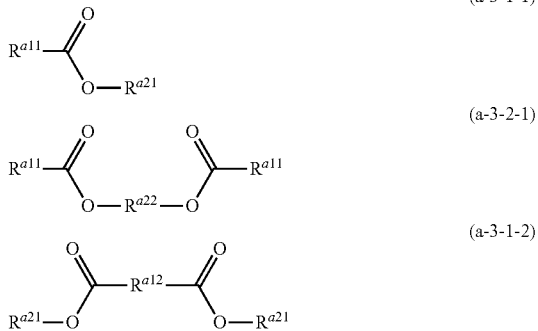

(wherein $R^{a11}$, $R^{a12}$, $R^{a21}$, and $R^{a22}$ have the same meanings as above; when the carboxylic acid is represented by general formula (a-1-1) above and the phenol or alcohol is represented by general formula (a-2-1) above, the ester group-containing compound is a compound represented by general formula (a-3-1-1); when the carboxylic acid is represented by general formula (a-1-1) above and the phenol or alcohol is represented by general formula (a-2-2) above, the ester group-containing compound is a compound represented by general formula (a-3-2-1); and, when the carboxylic acid is represented by general formula (a-1-2) above and the phenol or alcohol is represented by general formula (a-2-1) above, the ester group-containing compound is a compound represented by general formula (a-3-1-2)).

One example of the ester group-containing compound is a compound represented by the following general formula (I):

[Chem. 7]

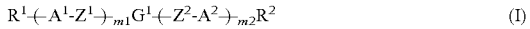

(wherein $R^1$ represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group which has 1 to 20 carbon atoms and in which one —$CH_2$— group or two or more non-adjacent —$CH_2$— groups are each independently optionally replaced with —O—, —S—, —CO—, —COO—, —OCO—, —CO—S—, —S—CO—, —O—CO—O—, —CO—NH—, —NH—CO—, —CH=CH—, —CF=CF—, or —C≡C—, any hydrogen atom in the alkyl group being optionally replaced with a fluorine atom, wherein, alternatively, $R^1$ represents a group represented by $P^1$-$(Sp^1$-$X^1)_{k1}$— (wherein $P^1$ represents a polymerizable group and preferably represents a group polymerizable through radical polymerization, radical addition polymerization, cationic polymerization, or anionic polymerization; $Sp^1$ represents a spacer group or a single bond; when a plurality of $Sp^1$s are present, they may be the same or different; $X^1$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO— CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond; when a plurality of $X^1$s are present, they may be the same or different (provided that $P^1$-$(Sp^1$-$X^1)_{k1}$— contains no —O—O— bond); and k1 represents an integer from 0 to 10), wherein, alternatively, $R^1$ represents a hydroxyl group protected by a protecting group, an amino group protected by a protecting group, a mercapto group protected by a protecting group, a carbonyl group protected by a protecting group, or a carboxyl group protected by a protecting group, wherein $R^2$ represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group which has 1 to 20 carbon atoms and in which one —$CH_2$— group or two or more non-adjacent —$CH_2$— groups are each independently optionally replaced with —O—, —S—, —CO—, —COO—, —OCO—, —CO—S—, —S—CO—, —O—CO—O—, —CO—NH—, —NH—CO—, —CH=CH—, —CF=CF—, or —C≡C—, any hydrogen atom in the alkyl group being optionally replaced with a fluorine atom, wherein, alternatively, $R^2$ represents a group represented by $P^2$-$(Sp^2$-$X^2)_{k2}$— (wherein $P^2$ represents a polymerizable group and preferably represents a group polymerizable through radical polymerization, radical addition polymerization, cationic polymerization, or anionic polymerization; $Sp^2$ represents a spacer group or a single bond; when a plurality of $Sp^2$s are present, they may be the same or different; $X^2$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO— CH=CH—, —OCO—CH=CH—, —COO—$CH_2CH_2$—, —OCO—$CH_2CH_2$—, —$CH_2CH_2$—COO—, —$CH_2CH_2$— OCO—, —COO—$CH_2$—, —OCO—$CH_2$—, —$CH_2$— COO—, —$CH_2$—OCO—, —CH=CH—, —N=N—, —CH=N—N=CH—, —CF=CF—, —C≡C—, or a single bond; when a plurality of $X^2$s are present, they may be the same or different (provided that $P^2$-$(Sp^2$-$X^2)_{k2}$— contains no —O—O— bond); and k2 represents an integer from 0 to 10), wherein, alternatively, $R^2$ represents a hydroxyl group protected by a protecting group, an amino group protected by a protecting group, a mercapto group protected by a protecting group, a carbonyl group protected by a protecting group, or a carboxyl group protected by a protecting group, wherein $A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, a tetrahydropyran-2,5-diyl group, or a 1,3-dioxane-2,5-diyl group, each of which may be unsubstituted or substituted by at least one substituent L; when a plurality of $A^1$s are present in the compound, they may be the same or different; and, when a plurality of $A^2$s are present in the compound, they may be the same or different, wherein L represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group which has 1 to 20 carbon atoms and in which one —CH$_2$— group or two or more non-adjacent —CH$_2$— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom in the alkyl group being optionally replaced with a fluorine atom, wherein, alternatively, L may represent a group represented by P$^L$-(Sp$^L$-X$^L$)$_{kL}$— wherein P$^L$ represents a polymerizable group and preferably represents a group polymerizable through radical polymerization, radical addition polymerization, cationic polymerization, or anionic polymerization; Sp$^L$ represents a spacer group or a single bond; when a plurality of Sp$^L$s are present, they may be the same or different; X$^L$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond; when a plurality of X$^L$s are present, they may be the same or different (provided that P$^L$-(Sp$^L$-X$^L$)$_{kL}$— contains no —O—O— bond); kL represents an integer from 0 to 10; and, when a plurality of Ls are present in the compound, they may be the same or different, wherein Z$^1$ and Z$^2$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CH=N—N=CH—, —CF=CF—, —C≡C—, or a single bond; when a plurality of Z$^1$s are present, they may be the same or different; when a plurality of Z$^2$s are present, they may be the same or different; and, at least one of Z$^1$ and Z$^2$ represents a group selected from —COO— and —OCO—, wherein G$^1$ represents a divalent group having at least one aromatic ring selected from the group consisting of aromatic hydrocarbon rings and aromatic heterocycles; the number of π electrons contained in the aromatic ring in the group represented by G$^1$ is 12 or more; and the group represented by G$^1$ may be unsubstituted or substituted by at least one substituent L$^{G1}$, wherein, alternatively, G$^1$ represents a group represented by A$^G$ or a group represented by C$^G$, wherein L$^{G1}$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group which has 1 to 20 carbon atoms and in which one —CH$_2$— group or two or more non-adjacent —CH$_2$— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom in the alkyl group being optionally replaced with a fluorine atom, wherein, alternatively, L$^{G1}$ may represent a group represented by P$^{LG}$-(Sp$^{LG}$-X$^{LG}$)$_{kLG}$— wherein P$^{LG}$ represents a polymerizable group and preferably represents a group polymerizable through radical polymerization, radical addition polymerization, cationic polymerization, or anionic polymerization; Sp$^{LG}$ represents a spacer group or a single bond; when a plurality of Sp$^{LG}$s are present, they may be the same or different; X$^{LG}$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond; when a plurality of X$^{LG}$s are present, they may be the same or different (provided that P$^{LG}$-(Sp$^{LG}$-X$^{LG}$)$_{kLG}$— contains no —O—O— bond); kLG represents an integer from 0 to 10; and, when a plurality of L$^{G1}$s are present in the compound, they may be the same or different, wherein A$^G$ represents a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, a tetrahydropyran-2,5-diyl group, or a 1,3-dioxane-2,5-diyl group, each of which is substituted by at least one substituent L$^{AG}$; L$^{AG}$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group which has 1 to 20 carbon atoms and in which one —CH$_2$— group or two or more non-adjacent —CH$_2$— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom in the alkyl group being optionally replaced with a fluorine atom; or, alternatively, L$^{AG}$ may represent a group represented by P$^{LAG}$-(Sp$^{LAG}$-X$^{LAG}$)$_{kLAG}$— wherein P$^{LAG}$ represents a polymerizable group and preferably represents a group polymerizable through radical polymerization, radical addition polymerization, cationic polymerization, or anionic polymerization; Sp$^{LAG}$ represents a spacer group or a single bond; when a plurality of Sp$^{LAG}$s are present, they may be the same or different; X$^{LAG}$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—

—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond; when a plurality of X$^{LAG}$s are present, they may be the same or different (provided that P$^{LAG}$-(Sp$^{LAG}$-X$^{LAG}$)$_{kLAG}$— contains no —O—O— bond); kLAG represents an integer from 0 to 10; and, when a plurality of L$^{AG}$s are present in the compound, they may be the same or different, and at least one LAG present in the compound represents a linear or branched alkyl group which has 1 to 20 carbon atoms, in which any hydrogen atom in the alkyl group is optionally replaced with a fluorine atom, and in which one —CH$_2$— group or two or more non-adjacent —CH$_2$— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, at least one —CH$_2$— group in the alkyl group being replaced with —CO—, wherein C$^G$ represents a groups having a chiral structure; C$^G$ may be unsubstituted or substituted by at least one substituent L$^{CG}$; L$^{CG}$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group which has 1 to 20 carbon atoms and in which one —CH$_2$— group or two or more non-adjacent —CH$_2$— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom in the alkyl group being optionally replaced with a fluorine atom; or, alternatively, L$^{CG}$ may represent a group represented by P$^{LCG}$-(Sp$^{LCG}$-X$^{LCG}$)$_{kLCG}$— wherein P$^{LCG}$ represents a polymerizable group and preferably represents a group polymerizable through radical polymerization, radical addition polymerization, cationic polymerization, or anionic polymerization; Sp$^{LCG}$ represents a spacer group or a single bond; when a plurality of Sp$^{LCG}$s are present, they may be the same or different; X$^{LCG}$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond; when a plurality of X$^{LCG}$s are present, they may be the same or different (provided that P$^{LCG}$-(Sp$^{LCG}$-X$^{LCG}$)$_{kLCG}$— contains no —O—O— bond); kLCG represents an integer from 0 to 10; and, when a plurality of L$^{CG}$s are present in the compound, they may be the same or different, wherein m1 represents an integer from 0 to 8, and wherein m2 represents an integer from 0 to 8). In general formula (I), when R$^1$ represents a group represented by P$^1$-(Sp$^1$-X$^1$)$_{k1}$— and/or R$^2$ is a group represented by P$^2$-(Sp$^2$-X$^2$)$_{k2}$—, P$^1$ and P$^2$ each represent a polymerizable group and each preferably represent a group polymerizable through radical polymerization, radical addition polymerization, cationic polymerization, or anionic polymerization. More preferably, P$^1$ and P$^2$ each independently represent a group selected from the following formula (P-1) to formula (P-20).

[Chem. 8]

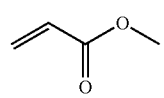 (P-1)

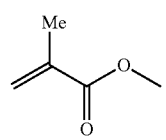 (P-2)

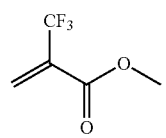 (P-3)

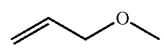 (P-4)

(P-5)

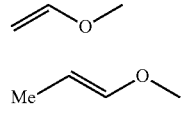 (P-6)

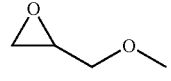 (P-7)

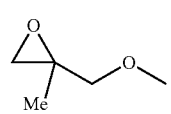 (P-8)

(P-9)

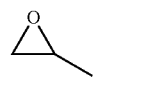 (P-10)

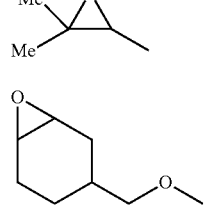 (P-11)

(P-12)

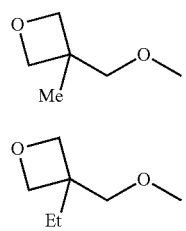 (P-13)

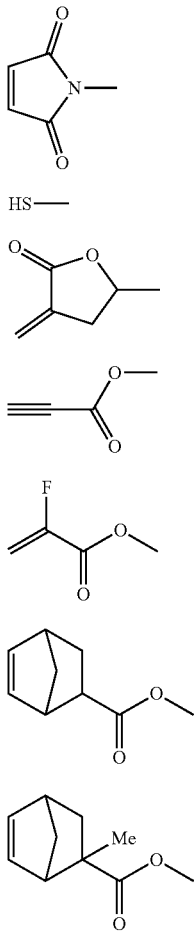

(P-124)

(P-15)

(P-16)

(P-17)

(P-18)

(P-19)

(P-20)

In particular, when the polymerization method used is ultraviolet polymerization, $P^1$ and $P^2$ preferably each independently represent a group selected from formula (P-1), formula (P-2), formula (P-3), formula (P-4), formula (P-5), formula (P-7), formula (P-11), formula (P-13), formula (P-15), and formula (P-18), more preferably each independently represent a group selected from formula (P-1), formula (P-2), formula (P-3), formula (P-7), formula (P-11), and formula (P-13), still more preferably each independently represent a group selected from formula (P-1), formula (P-2), and formula (P-3), and particularly preferably each independently represent a group selected from formula (P-1) and formula (P-2).

$Sp^1$ and $Sp^2$ each independently represent a spacer group or a single bond. When a plurality of $Sp^1$s and $Sp^2$s are present, they may be the same or different. The spacer group is preferably an alkylene group which has 1 to 20 carbon atoms and in which one —$CH_2$— group or two or more non-adjacent —$CH_2$— groups are each independently optionally replaced with —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, or —C≡C—. When a plurality of $Sp^1$s and $Sp^2$s are present, they may be the same or different. From the viewpoint of availability of raw materials and ease of synthesis, $Sp^1$ and $Sp^2$ preferably each independently represent an alkylene group which has 1 to 20 carbon atoms and in which one —$CH_2$— group or two or more non-adjacent —$CH_2$— groups are each independently optionally replaced with —O—, —COO—, —OCO—, —OCO—O—, —CO—NH—, —NH—CO—, —CH=CH—, or —C≡C—, more preferably each independently represent a single bond or an alkylene group which has 1 to 10 carbon atoms and in which one —$CH_2$— group or two or more non-adjacent —$CH_2$— groups are each independently optionally replaced with —O—, —COO—, or —OCO—, still more preferably each independently represent a single bond or an alkylene group having 1 to 10 carbon atoms. When a plurality of $Sp^1$s and $Sp^2$s are present, they may be the same or different, and it is particularly preferable that they each independently represent an alkylene group having 1 to 8 carbon atoms.

$X^1$ and $X^2$ each represent —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond. When a plurality of $X^1$s and $X^2$s are present, they may be the same or different. From the viewpoint of availability of raw materials and ease of synthesis, when a plurality of $X^1$s and $X^2$s are present, they may be the same or different, preferably each independently represent —O—, —S—, —$OCH_2$—, —$CH_2O$—, —COO—, —OCO—, —CO—S—, —S—CO—, —O—CO—O—, —CO—NH—, —NH—CO—, —COO—$CH_2CH_2$—, —OCO—$CH_2CH_2$—, —$CH_2CH_2$—COO—, —$CH_2CH_2$—OCO—, or a single bond, and more preferably each independently represent —O—, —$OCH_2$—, —$CH_2O$—, —COO—, —OCO—, —COO—$CH_2CH_2$—, —OCO—$CH_2CH_2$—, —$CH_2CH_2$—COO—, —$CH_2CH_2$—OCO—, or a single bond. When a plurality of $X^1$s and $X^2$s are present, they may be the same or different and particularly preferably each independently represent —O—, —COO—, —OCO—, or a single bond.

k1 and k2 each independently represent an integer from 0 to 10, preferably each independently represent an integer from 0 to 5, more preferably each independently represent an integer from 0 to 2, and particularly preferably each represent 1.

When $R^1$ and $R^2$ each represent a hydroxyl group protected by a protecting group, an amino group protected by a protecting group, a mercapto group protected by a protecting group, a carbonyl group protected by a protecting group, or a carboxyl group protected by a protecting group, the protecting groups are preferably those listed in, for example, GREENE'S PROTECTIVE GROUPS IN ORGANIC SYNTHESIS ((Fourth Edition), PETER G. M. WUTS and THEODORA W. GREENE, John Wiley & Sons, Inc., Publication). More specifically, $R^1$ and $R^2$ are each independently a tetrahydropyranyloxy group, a tert-butyloxy group, a methoxymethoxy group, an ethoxymethoxy group, an acetyloxy group, a benzyloxy group, a tetrahydropyranyloxycarbonyl group, a tert-butyloxycarbonyl group, a methoxymethoxycarbonyl group, an ethoxymethoxycarbonyl group, a benzyloxycarbonyl group, etc.

When $R^1$ is a group other than the group represented by $P^1\text{-}(Sp^1\text{-}X^1)_{k1}\text{—}$, a hydroxyl group protected by a protecting group, an amino group protected by a protecting group, a mercapto group protected by a protecting group, a carbonyl group protected by a protecting group, and a carboxyl group protected by a protecting group and when $R^2$ is a group other than the group represented by $P^2\text{-}(Sp^2\text{-}X^2)_{k2}\text{—}$, a hydroxyl group protected by a protecting group, an amino group protected by a protecting group, a mercapto group protected by a protecting group, a carbonyl group protected by a protecting group, and a carboxyl group protected by a protecting group, it is preferable from the viewpoint of liquid crystallinity and ease of synthesis that $R^1$ and $R^2$ each independently represent a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group which has 1 to 20 carbon atoms, in which any hydrogen atom in the group is optionally substituted by a fluorine atom, and in which one —$CH_2$— group or two or more non-adjacent —$CH_2$— groups are each independently optionally replaced with —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, or —C≡C—. $R^1$ and $R^2$ more preferably each independently represent a hydrogen atom, a fluorine atom, a chlorine atom, or a linear or branched alkyl group which has 1 to 12 carbon atoms and in which one —$CH_2$— group or two or more non-adjacent —$CH_2$— groups are each independently optionally replaced with —O—, —COO—, —OCO—, or —O—CO—O—, still more preferably each independently represent a hydrogen atom, a fluorine atom, a chlorine atom, a linear alkyl group having 1 to 12 carbon atoms, or a linear alkoxy group having 1 to 12 carbon atoms, and particularly preferably each independently represent a linear alkyl group having 1 to 12 carbon atoms or a linear alkoxy group having 1 to 12 carbon atoms.

When importance is placed on the mechanical strength of a film formed from the compound represented by general formula (I), it is preferable that at least one of $R^1$ and $R^2$ present in the compound is the group represented by $P^1\text{-}(Sp^1\text{-}X^1)_{k1}\text{—}$ or the group represented by $P^2\text{-}(Sp^2\text{-}X^2)_{k2}\text{—}$, and it is more preferable that $R^1$ and $R^2$ present in the compound are each the group represented by $P^1\text{-}(Sp^1\text{-}X)_{k1}\text{—}$ or the group represented by $P^2\text{-}(Sp^2\text{-}X^2)_{k2}\text{—}$.

In general formula (I), $A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, each of which may be unsubstituted or substituted by at least one substituent L described above. $A^1$ and $A^2$ preferably each independently represent a 1,4-phenylene group, a 1,4-cyclohexylene group, or a naphthalene-2,6-diyl group, each of which may be unsubstituted or substituted by at least one substituent L. $A^1$ and $A^2$ more preferably each independently represent a group selected from the following formula (A-1) to formula (A-11):

[Chem. 9]

(A-1)

(A-2)

(A-3)

(A-4)

(A-5)

(A-6)

(A-7)

(A-8)

(A-9)

(A-10)

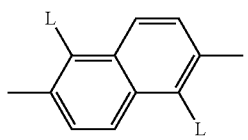
(A-11)

still more preferably each independently represent a group selected from formula (A-1) to formula (A-8), and particularly preferably each independently represent a group selected from formula (A-1) to formula (A-4).

In general formula (I), L represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group which has 1 to 20 carbon atoms and in which one —CH$_2$— group or two or more non-adjacent —CH$_2$— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom in the alkyl group being optionally replaced with a fluorine atom. Alternatively, L may represent a group represented by P$^L$-(Sp$^L$-X$^L$)$_{kL}$—. Here, P$^L$ represents a polymerizable group and preferably represents a group polymerizable through radical polymerization, radical addition polymerization, cationic polymerization, or anionic polymerization, and Sp$^L$ represents a single bond or a linear alkylene group which has a 1 to 10 carbon atoms and in which one —CH$_2$— group or two or more non-adjacent —CH$_2$— groups are each independently optionally replaced with —O—, —COO—, or —OCO—. When a plurality of Sp$^L$s are present, they may be the same or different. X$^L$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —COO—CH$_2$CH$_2$—, —OCO—CH$_2$CH$_2$—, —CH$_2$CH$_2$—COO—, —CH$_2$CH$_2$—OCO—, —CH$_2$—OCO—, —CH$_2$—COO—, —CH$_2$—OCO—, —CH=CH—, —N=N—, —CH=N—N=CH—, —CF=CF—, —C≡C—, or a single bond. When a plurality of X$^L$s are present, they may be the same or different (provided that P$^L$-(Sp$^L$-X$^L$)$_{kL}$— contains no —O—O— bond). kL represents an integer from 0 to 10. When a plurality of Ls are present in the compound, they may be the same or different. From the viewpoint of liquid crystallinity and ease of synthesis, when a plurality of Ls are present, they may be the same or different and each preferably represent a fluorine atom, a chlorine atom, a pentafluorosulfuranyl group, a nitro group, a methylamino group, a dimethylamino group, a diethylamino group, a diisopropylamino group, or a linear or branched alkyl group which has 1 to 20 carbon atoms, in which any hydrogen atom is optionally replaced with a fluorine atom, and in which one —CH$_2$— group or non-adjacent two or more —CH$_2$— groups are each independently optionally replaced with a group selected from —O—, —S—, —CO—, —COO—, —OCO—, —O—CO—O—, —CH=CH—, —CF=CF—, and —C≡C—. When a plurality of Ls are present, they may be the same or different and more preferably each represent a fluorine atom, a chlorine atom, or a linear or branched alkyl group which has 1 to 12 carbon atoms, in which any hydrogen atom is optionally replaced with a fluorine atom, and in which one —CH$_2$— group or non-adjacent two or more —CH$_2$— groups are each independently optionally replaced with a group selected from —O—, —CO—, —COO—, and —OCO—. When a plurality of Ls are present, they may be the same or different and still more preferably each represent a fluorine atom, a chlorine atom, or a linear or branched alkyl or alkoxy group which has 1 to 12 carbon atoms and in which any hydrogen atom is optionally replaced with a fluorine atom. When a plurality of Ls are present, they may be the same or different and particularly preferably each represent a fluorine atom, a chlorine atom, or a linear alkyl or alkoxy group having 1 to 8 carbon atoms.

In general formula (I), Z$^1$ and Z$^2$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond. When a plurality of Z$^1$s are present, they may be the same or different. When a plurality of Z$^2$s are present, they may be the same or different. And at least one of Z$^1$ and Z$^2$ represents a group selected from —COO— and —OCO—. In general formula (I), when the sum of m$^1$ and m$^2$ is 3 or more, a plurality of Z$^1$s and/or a plurality of Z$^2$s are present. In this case, it is preferable that at least one of Z$^1$ and Z$^2$ that are adjacent to G$^1$ or at least one of Z$^1$ and Z$^2$ that are adjacent to an (A$^1$-Z$^1$) or (Z$^2$-A$^2$) unit adjacent to G$^1$ represents a group selected from —COO— and —OCO—. From the viewpoint of liquid crystallinity, availability of raw materials, and ease of synthesis, Z$^1$s and Z$^2$s preferably each independently represent —OCH$_2$—, —CH$_2$O—, —COO—, —OCO—, —CF$_2$O—, —OCF$_2$—, —CH$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —CH=CH—, —CF=CF—, —C≡C—, or a single bond, more preferably each independently represent —OCH$_2$—, —CH$_2$O—, —COO—, —OCO—, —CF$_2$O—, —OCF$_2$—, —CH$_2$CH$_2$—, —COO—CH$_2$CH$_2$—, —OCO—CH$_2$CH$_2$—, —CH$_2$CH$_2$—COO—, —CH$_2$CH$_2$—OCO—, —CH=CH—, —C≡C—, or a single bond, still more preferably each independently represent —OCH$_2$—, —CH$_2$O—, —COO—, —OCO—, —CF$_2$O—, —OCF$_2$—, or a single bond, yet more preferably each independently represent —OCH$_2$—, —CH$_2$O—, —COO—, —OCO—, or a single bond, and particularly preferably each independently represent —OCH$_2$—, —CH$_2$O—, —COO—, or —OCO—.

In general formula (I), G$^1$ represents a divalent group having at least one aromatic ring selected from the group consisting of aromatic hydrocarbon rings and aromatic heterocycles. The number of π electrons contained in the aromatic ring in the group represented by $G^1$ is 12 or more, and the group represented by $G^1$ may be unsubstituted or substituted by at least one substituent $L^{G1}$. When importance is attached to reverse wavelength dispersion, $G^1$ is preferably a group having an absorption maximum at 300 nm to 900 nm and more preferably a group having an absorption maximum at 310 nm to 500 nm. From the viewpoint of the liquid crystallinity of the compound, availability of raw materials, and ease of synthesis, $G^1$ more preferably represents a group selected from the following formula (M-1) to formula (M-6):

[Chem. 10]

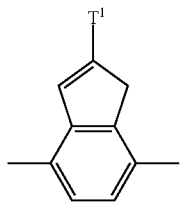
(M-1)

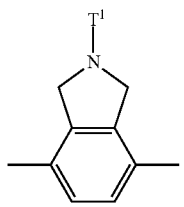
(M-2)

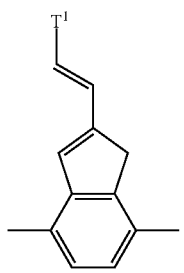
(M-3)

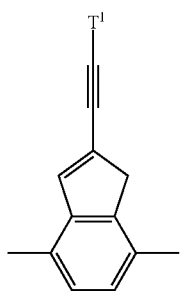
(M-4)

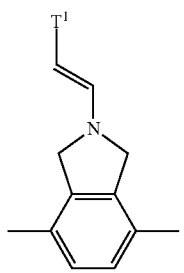
(M-5)

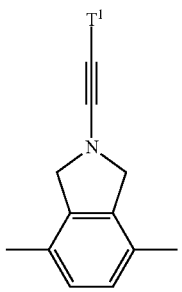
(M-6)

(wherein each of these groups may be unsubstituted or substituted by at least one substituent $L^{G1}$ described above; each —CH= is independently optionally replaced with —N=; each —CH$_2$— is independently optionally replaced with —O—, —S—, —NR$^T$— (wherein R$^T$ represents a hydrogen atom or an alkyl group having 1 to 20 carbon atoms), —CS—, or —CO—; and T$^1$ represents a group selected from the following formula (T1-1) to formula (T1-6):

[Chem. 11]

(T1-1)

(T1-2)

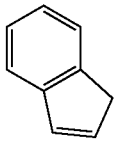
(T1-3)

(T1-4)

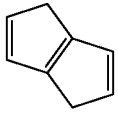
(T1-5)

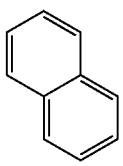
(T1-6)

(wherein each of these groups may have a bond at any position; each —CH= is independently optionally replaced with —N=; each —CH$_2$— is independently optionally replaced with —O—, —S—, —NR$^T$— (wherein R$^T$ represents a hydrogen atom or an alkyl group having 1 to 20 carbon atoms), —CS—, or —CO—, wherein the phrase "each of these groups may have a bond at any position"

means that, when, for example, formula (T1-1) is bonded to T¹ of one of formula (M-1) to formula (M-6), formula (T1-1) may have one bond at any position (as for the phrase "each of these groups may have a bond at any position" in the following description of the present invention, the same meaning applies), and wherein each of these groups may be unsubstituted or substituted by at least one substituent $L^{G1}$ described above). Alternatively, $G^1$ more preferably represents a group selected from the following formula (M-7) to formula (M-14):

[Chem. 12]

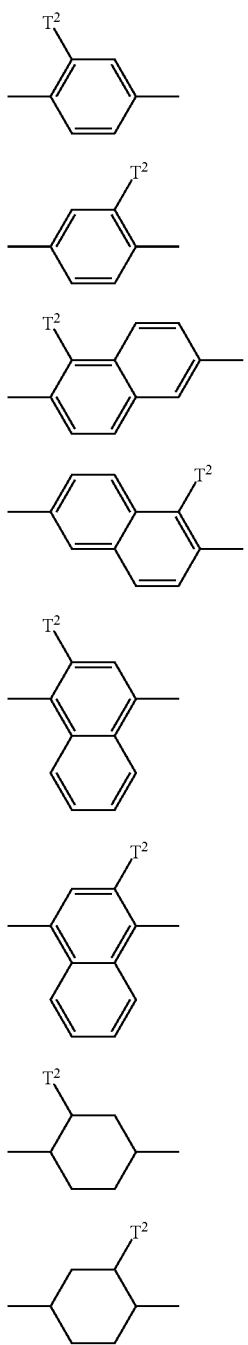

(M-7)
(M-8)
(M-9)
(M-10)
(M-11)
(M-12)
(M-13)
(M-14)

(wherein each of these groups may be unsubstituted or substituted by at least one substituent $L^{G1}$ described above; each —CH= is independently optionally replaced with —N=; each —CH$_2$— is independently optionally replaced with —O—, —S—, —NR$^T$— (wherein R$^T$ represents a hydrogen atom or an alkyl group having 1 to 20 carbon atoms), —CS—, or —CO—; and T² represents a group selected from the following formula (T2-1) and formula (T2-2):

[Chem. 13]

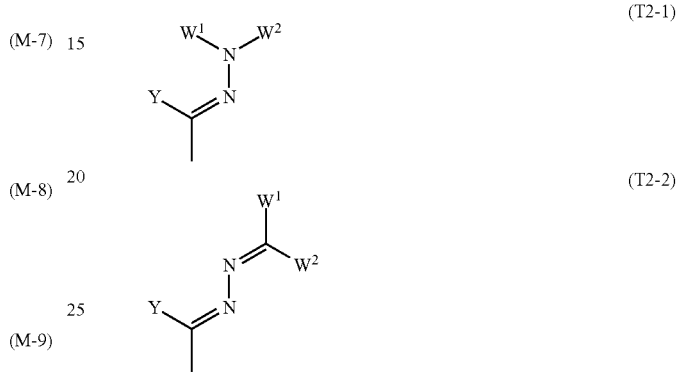

(T2-1)
(T2-2)

(wherein W¹ represents a group containing an optionally substituted aromatic group having 1 to 40 carbon atoms and/or an optionally substituted non-aromatic group having 1 to 40 carbon atoms; the aromatic group may be a hydrocarbon ring or a heterocycle; and the non-aromatic group may be a hydrocarbon group or a hydrocarbon group in which a carbon atom in the group is replaced with a heteroatom (provided that oxygen atoms are not bonded directly to each other), wherein W² represents a hydrogen atom or a linear or branched alkyl group which has 1 to 20 carbon atoms and in which one —CH$_2$— group or two or more non-adjacent —CH$_2$— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom in the alkyl group being optionally replaced with a fluorine atom, wherein, alternatively, W² may represent a group having at least one aromatic group and having 2 to 30 carbon atoms (excluding carbon atoms in the aromatic group), and the group may be unsubstituted or substituted by at least one substituent $L^W$, wherein, alternatively, W² may represent a group represented by P$^W$-(Sp$^W$-X$^W$)$_{kW}$— wherein P$^W$ represents a polymerizable group and preferably represents a group polymerizable through radical polymerization, radical addition polymerization, cationic polymerization, or anionic polymerization; preferred polymerizable groups are as defined above for P¹; Sp$^W$ represents a spacer group or a single bond; preferred spacer groups are as defined above for Sp¹; when a plurality of Sp$^W$s are present, they may be the same or different; X$^W$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—

CH=CH—, —OCO—CH=CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—N=CH—, —CF=CF—, —C≡C—, or a single bond; when a plurality of $X^W$s are present, they may be the same or different (provided that $P^W$-$(Sp^W$-$X^W)_{kW}$— contains no —O—O— bond); and kW represents an integer from 0 to 10, wherein $L^W$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group which has 1 to 20 carbon atoms and in which one —CH₂— group or two or more non-adjacent —CH₂— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom in the alkyl group being optionally replaced with a fluorine atom, wherein, alternatively, $L^W$ may represent a group represented by $P^{LW}$-$(Sp^W$-$X^W)_{kLW}$— wherein $P^{LW}$ represents a polymerizable group and preferably represents a group polymerizable through radical polymerization, radical addition polymerization, cationic polymerization, or anionic polymerization; $Sp^{LW}$ represents a spacer group or a single bond; when a plurality of $Sp^{LW}$s are present, they may be the same or different; $X^{LW}$ represents —O—, —S—, —OCH₂—, —CH₂O—, —CO—, —COO—, —OCO—, —CO—S—, —S—CO—, —O—CO—O—, —CO—NH—, —NH—CO—, —SCH₂—, —CH₂S—, —CF₂O—, —OCF₂—, —CF₂S—, —SCF₂—, —CH=CH—COO—, —CH=CH—OCO—, —COO—CH=CH—, —OCO—CH=CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—N=CH—, —CF=CF—, —C≡C—, or a single bond; when a plurality of $X^{LW}$s are present, they may be the same or different (provided that $P^{LW}$-$(Sp^{LW}$-$X^{LW})_{kLW}$— contains no —O—O— bond); kLW represents an integer from 0 to 10; and, when a plurality of $L^W$s are present in the compound, they may be the same or different, wherein Y represents a hydrogen atom, a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group which has 1 to 20 carbon atoms and in which one —CH₂— group or two or more non-adjacent —CH₂— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom in the alkyl group being optionally replaced with a fluorine atom, and wherein, alternatively, Y may represent a group represented by $P^Y$-$(Sp^Y$-$X^Y)_{kY}$— wherein $P^Y$ represents a polymerizable group; preferred polymerizable groups are as defined above for $P^1$; $Sp^Y$ represents a spacer group or a single bond; preferred spacer groups are as defined above for $Sp^1$; when a plurality of $Sp^Y$s are present, they may be the same or different; $X^Y$ represents —O—, —S—, —OCH₂—, —CH₂O—, —CO—, —COO—, —OCO—, —CO—S—, —S—CO—, —O—CO—O—, —CO—NH—, —NH—CO—, —SCH₂—, —CH₂S—, —CF₂O—, —OCF₂—, —CF₂S—, —SCF₂—, —CH=CH—COO—, —CH=CH—OCO—, —COO—CH=CH—, —OCO—CH=CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—N=CH—, —CF=CF—, —C≡C—, or a single bond; when a plurality of $X^Y$s are present, they may be the same or different (provided that $P^Y$-$(Sp^Y$-$X^Y)_{kY}$— contains no —O—O— bond); kY represents an integer from 0 to 10; and $W^1$ and $W^2$ may together form a ring structure)). From the viewpoint of solubility in a solvent and ease of synthesis, $G^1$ more preferably represents a group selected from formula (M-1), formula (M-3), formula (M-4), formula (M-7), and formula (M-8) above, still more preferably represents a group selected from formula (M-1), formula (M-7), and formula (M-8), and particularly preferably represents a group selected from formula (M-7) and formula (M-8). More specifically, the group represented by formula (M-1) preferably represents a group selected from the following formula (M-1-1) to formula (M-1-6):

[Chem. 14]

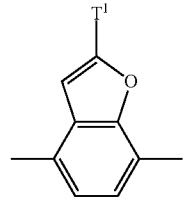
(M-1-1)

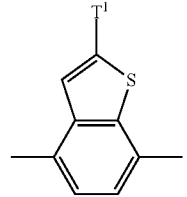
(M-1-2)

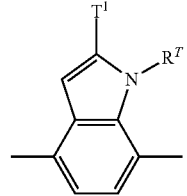
(M-1-3)

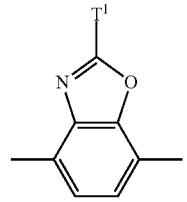
(M-1-4)

(M-1-5)

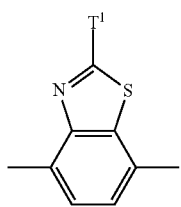

(M-1-6)

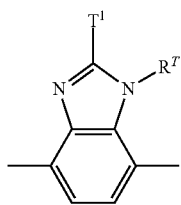

(wherein $T^1$ has the same meaning as above, and $R^T$ represents a hydrogen atom or an alkyl group having 1 to 20 carbon atoms), more preferably represents a group selected from formula (M-1-4) and formula (M-1-5), and particularly preferably represents a group represented by formula (M-1-5). The group represented by formula (M-3) preferably represents a group selected from the following formula (M-3-1) to formula (M-3-6):

[Chem. 15]

(M-3-1)

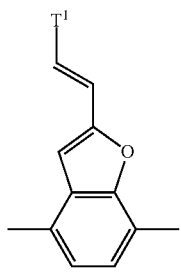

(M-3-2)

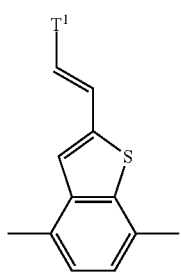

(M-3-3)

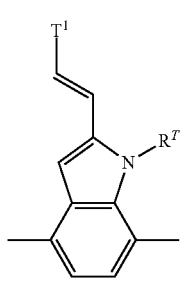

(M-3-4)

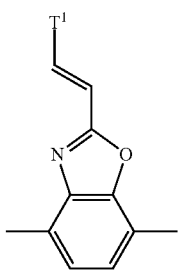

(M-3-5)

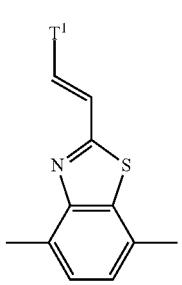

(M-3-6)

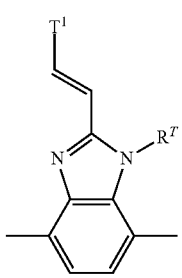

(wherein $T^1$ has the same meaning as above, and $R^T$ represents a hydrogen atom or an alkyl group having 1 to 20 carbon atoms), more preferably represents a group selected from formula (M-3-4) and formula (M-3-5), and particularly preferably a group represented by formula (M-3-5). The group represented by formula (M-4) preferably represents a group selected from the following formula (M-4-1) to formula (M-4-6):

[Chem. 16]

(M-4-1)

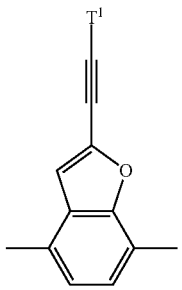

-continued (M-4-2)

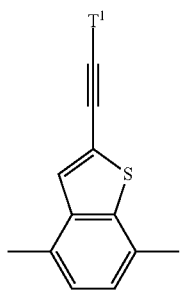

(M-4-3)

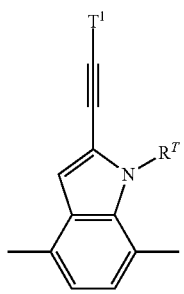

(M-4-4)

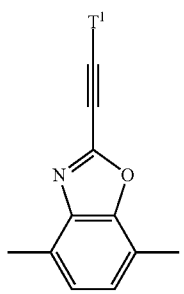

(M-4-5)

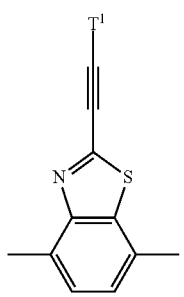

(M-4-6)

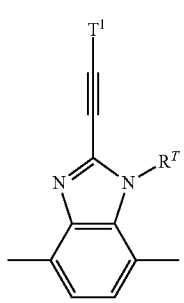

(wherein $T^1$ has the same meaning as above, and $R^T$ represents a hydrogen atom or an alkyl group having 1 to 20 carbon atoms), more preferably represents a group selected from formula (M-4-4) and formula (M-4-5), and particularly preferably represents a group represented by formula (M-4-5). The groups represented by formula (M-7) to formula (M-14) are preferably groups represented by the following formula (M-7-1) to formula (M-14-1):

[Chem. 17]

(M-7-1)

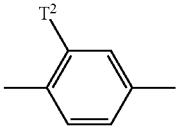

(M-8-1)

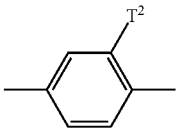

(M-9-1)

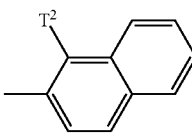

(M-10-1)

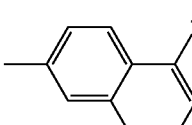

(M-11-1)

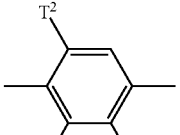

(M-12-1)

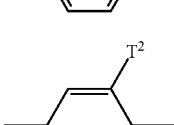

(M-13-1)

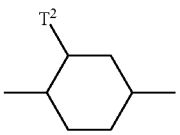

(M-14-1)

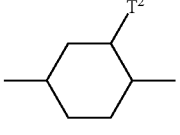

(wherein $T^2$ has the same meaning as above), more preferably groups selected from formula (M-7-1) to formula (M-12-1), and particularly preferably groups represented by formula (M-7-1) and formula (M-8-1).

In formula (M-1) to formula (M-6), it is preferable from the viewpoint of wavelength dispersion and ease of synthesis that $T^1$ represents a group selected from formula (T1-1), formula (T1-2), formula (T1-3), and formula (T1-6). $T^1$ more preferably represents a group selected from formula (T1-3) and formula (T1-6) and particularly preferably represents formula (T1-3). More specifically, the group represented by formula (T1-1) preferably represents a group selected from the following formula (T1-1-1) to formula (T1-1-7):

[Chem. 18]

(T1-1-1)

(T1-1-2)

(T1-1-3)
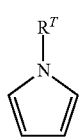

(T1-1-4)

(T1-1-5)

(T1-1-6)
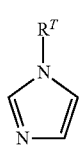

(T1-1-7)
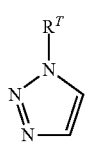

(wherein each of these groups may have a bond at any position; $R^T$ represents a hydrogen atom or an alkyl group having 1 to 20 carbon atoms; and each of these groups may be unsubstituted or substituted by at least one substituent $L^{G1}$ described above) and more preferably represents a group selected from formula (T1-1-2), formula (T1-1-4), formula (T1-1-5), formula (T1-1-6), and formula (T1-1-7). The group represented by formula (T1-2) preferably represents a group selected from the following formula (T1-2-1) to formula (T1-2-8):

[Chem. 19]

(T1-2-1)

(T1-2-2)

(T1-2-3)
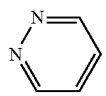

(T1-2-4)
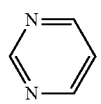

(T1-2-5)
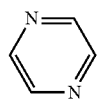

(T1-2-6)
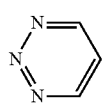

(T1-2-7)
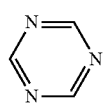

(T1-2-8)
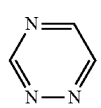

(wherein each of these groups may have a bond at any position, and each of these groups may be unsubstituted or substituted by at least one substituent $L^{G1}$ described above) and more preferably represents a group represented by formula (T1-2-1). The group represented by formula (T1-3) preferably represents a group selected from the following formula (T1-3-1) to formula (T1-3-8):

[Chem. 20]

(T1-3-1)
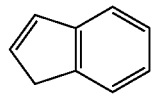

(T1-3-2)
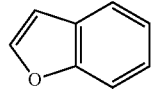

(T1-3-3)
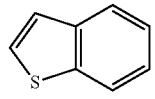

(T1-3-4)
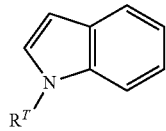

(T1-3-5)
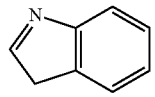

(T1-3-6)
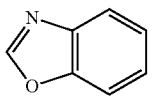

(T1-3-7)
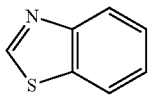

(T1-3-8)
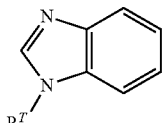

(wherein each of these groups may have a bond at any position; $R^T$ represents a hydrogen atom or an alkyl group having 1 to 20 carbon atoms; and each of these groups may be unsubstituted or substituted by at least one substituent $L^{G1}$ described above) and more preferably represents a group selected from formula (T1-3-2), formula (T1-3-3), formula (T1-3-6), and formula (T1-3-7). The group represented by formula (T1-4) preferably represents a group selected from the following formula (T1-4-1) to formula (T1-4-6):

[Chem. 21]

(T1-4-1)
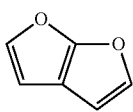

(T1-4-2)
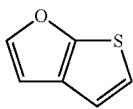

(T1-4-3)
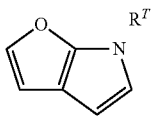

(T1-4-4)
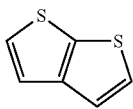

(T1-4-5)
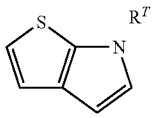

(T1-4-6)
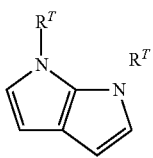

(wherein each of these groups may have a bond at any position; $R^T$ represents a hydrogen atom or an alkyl group having 1 to 20 carbon atoms; and each of these groups may be unsubstituted or substituted by at least one substituent $L^{G1}$ described above). The group represented by formula (T1-5) preferably represents a group selected from the flowing formula (T1-5-1) to formula (T1-5-9):

[Chem. 22]

(T1-5-1)
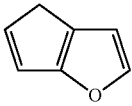

(T1-5-2)
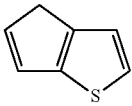

(T1-5-3)
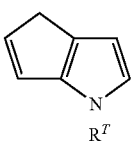

(T1-5-4)
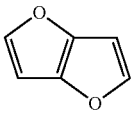

(T1-5-5)
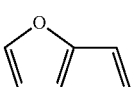

(T1-5-6)
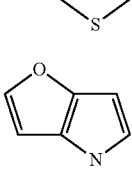

(T1-5-7)
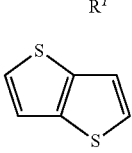

(T1-5-8)
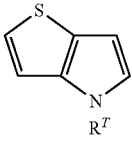

(T1-5-9)
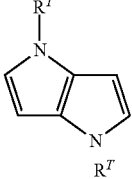

(wherein each of these groups may have a bond at any position; $R^T$ represents a hydrogen atom or an alkyl group having 1 to 20 carbon atoms; and each of these groups may be unsubstituted or substituted by at least one substituent $L^{G1}$ described above). The group represented by formula (T1-6) preferably represents a group selected from the following formula (T1-6-1) to formula (T1-6-7):

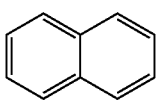 (T1-6-1)

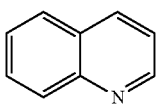 (T1-6-2)

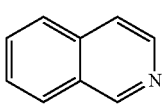 (T1-6-3)

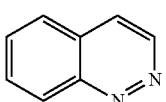 (T1-6-4)

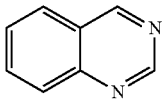 (T1-6-5)

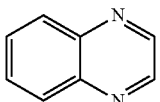 (T1-6-6)

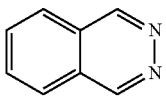 (T1-6-7)

(wherein each of these groups may have a bond at any position, and each of these groups may be unsubstituted or substituted by at least one substituent $L^{G1}$ described above)

From the viewpoint of ease of synthesis, availability of raw materials, and liquid crystallinity, $L^{G1}$ preferably represents a fluorine atom, a chlorine atom, a nitro group, a cyano group, a methylamino group, a dimethylamino group, a diethylamino group, a diisopropylamino group, or a linear or branched alkyl group which has 1 to 20 carbon atoms, in which any hydrogen atom in the group is optionally replaced with a fluorine atom, and in which one —CH$_2$— group or two or more non-adjacent —CH$_2$— groups are each independently optionally replaced with —O—, —S—, —CO—, —COO—, —OCO—, —O—CO—O—, —CH=CH—, —CF=CF—, or —C≡C—. $L^{G1}$ preferably represents a fluorine atom, a chlorine atom, a nitro group, a cyano group, a methylamino group, a dimethylamino group, or a linear or branched alkyl group which has 1 to 20 carbon atoms, in which any hydrogen atom in the group is optionally replaced with a fluorine atom, and in which one —CH$_2$— group or two or more non-adjacent —CH$_2$— groups are each independently optionally replaced with —O—, —S—, or —CO—. $L^{G1}$ more preferably represents a fluorine atom, a chlorine atom, a nitro group, a cyano group, a methylamino group, a dimethylamino group, or a linear alkyl group which has 1 to 10 carbon atoms, in which any hydrogen atom in the group is optionally replaced with a fluorine atom, and in which one —CH$_2$— group or two or more non-adjacent —CH$_2$— groups are each independently optionally replaced with —O—. $L^{G1}$ still more preferably represents a fluorine atom, a chlorine atom, a nitro group, a cyano group, a dimethylamino group, or a linear alkyl group which has 1 or 2 carbon atoms, in which any hydrogen atom in the group is optionally replaced with a fluorine atom, and in which one —CH$_2$— group or two or more non-adjacent —CH$_2$— groups are each independently optionally replaced with —O—.

In general formula (I), when the group represented by $G^1$ is a divalent group which may be unsubstituted or substituted by at least one substituent $L^{G1}$, which has at least one aromatic ring selected from the group consisting of aromatic hydrocarbon rings and aromatic heterocycles, and in which the number of π electrons contained the aromatic ring in the group is 12 or more, $G^1$ more preferably represents a group selected from the following formula (G-1) to formula (G-22):

[Chem. 24]

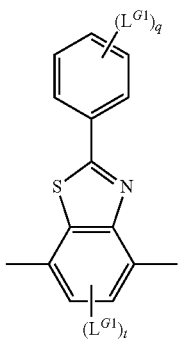 (G-1)

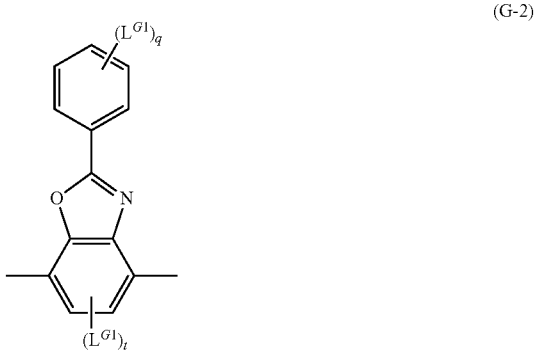 (G-2)

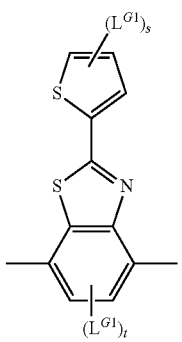 (G-3)

(G-4) 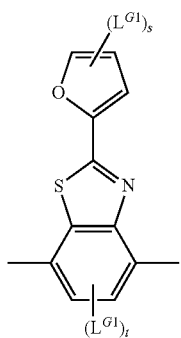
(G-5) 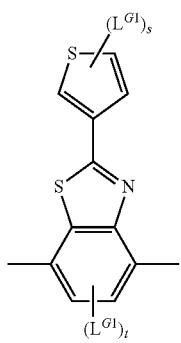
(G-6) 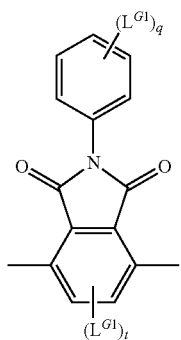
(G-7) 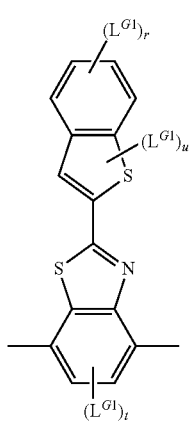
(G-8) 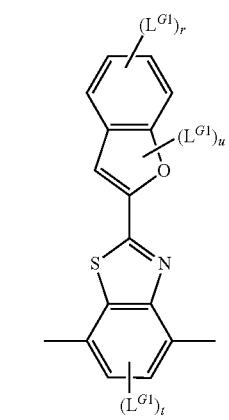
(G-9) 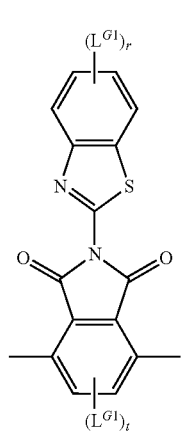
(G-10)

[Chem. 25]
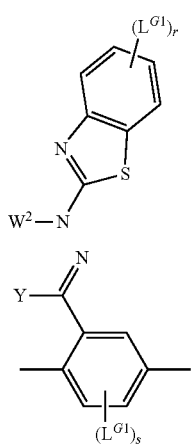
(G-11)
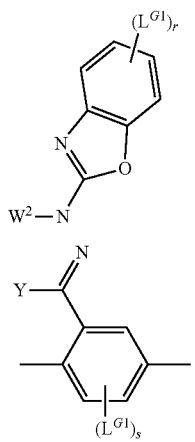
(G-12)
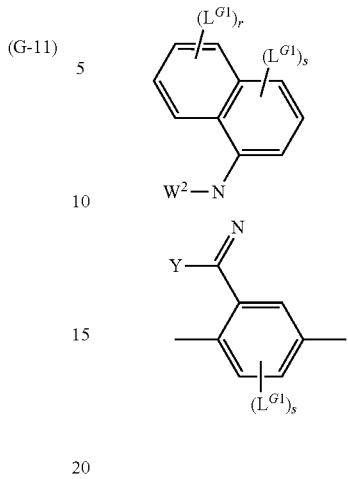
(G-13)
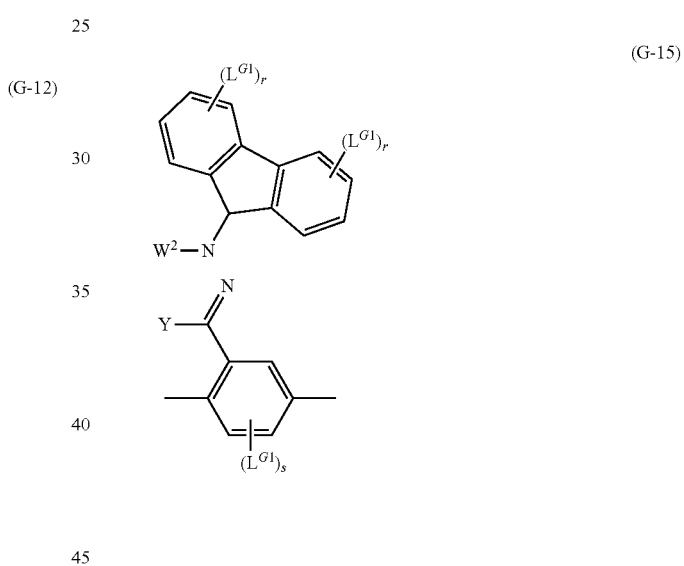
(G-14)
(G-15)
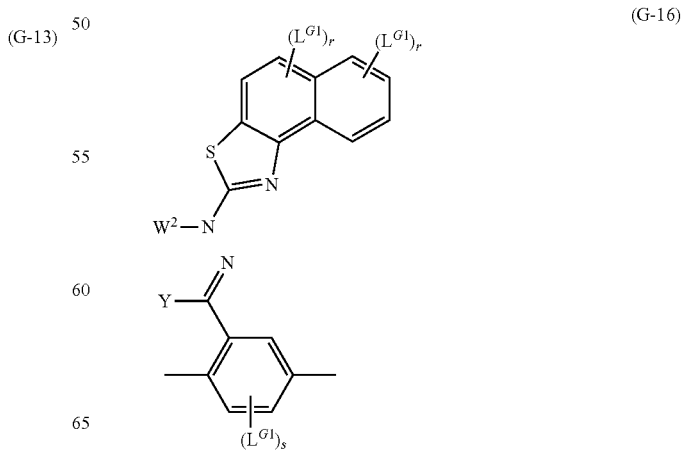
(G-16)

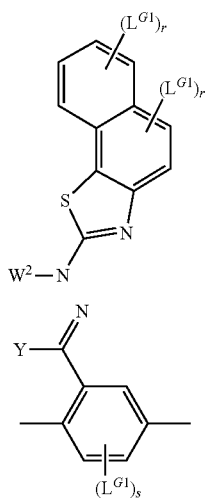
(G-17)

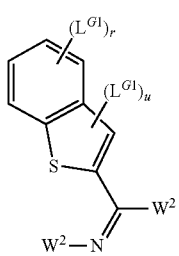
(G-18)

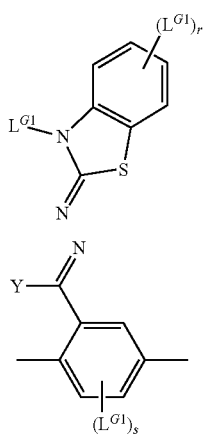
(G-19)

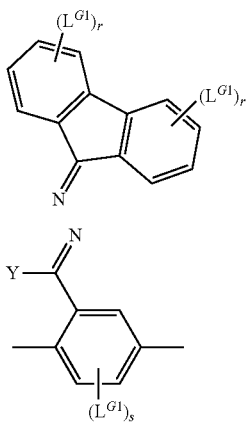
(G-20)

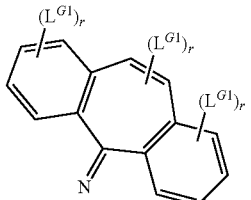

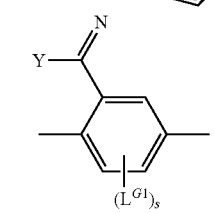
(G-21)

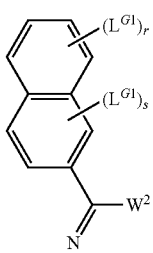

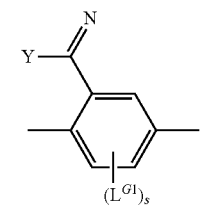
(G-22)

(wherein $L^{G1}$, Y, and $W^2$ have the same meanings as above; q represents an integer from 0 to 5; r represents an integer from 0 to 4; s represents an integer from 0 to 3; t represents an integer from 0 to 2; u represents 0 or 1; and each of these groups may be mirror-inverted). Among formula (G-1) to formula (G-10) above, a group selected from formula (G-1), formula (G-3), formula (G-5), formula (G-6), formula (G-7), formula (G-8), and formula (G-10) is more preferable, and a group with t=0 is still more preferable. A group selected from the following formula (G-1-1) to formula (G-10-1):

[Chem. 26]
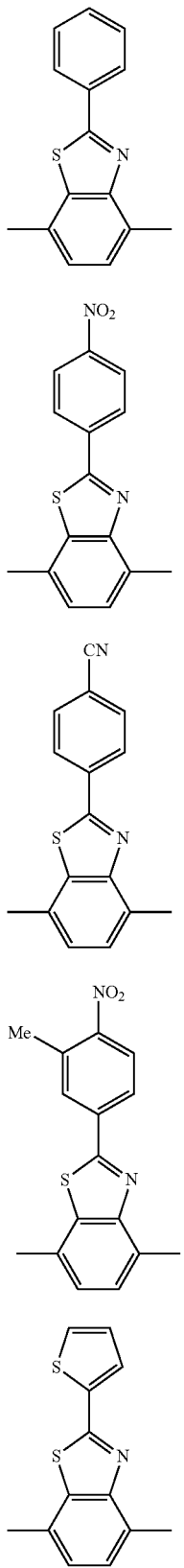
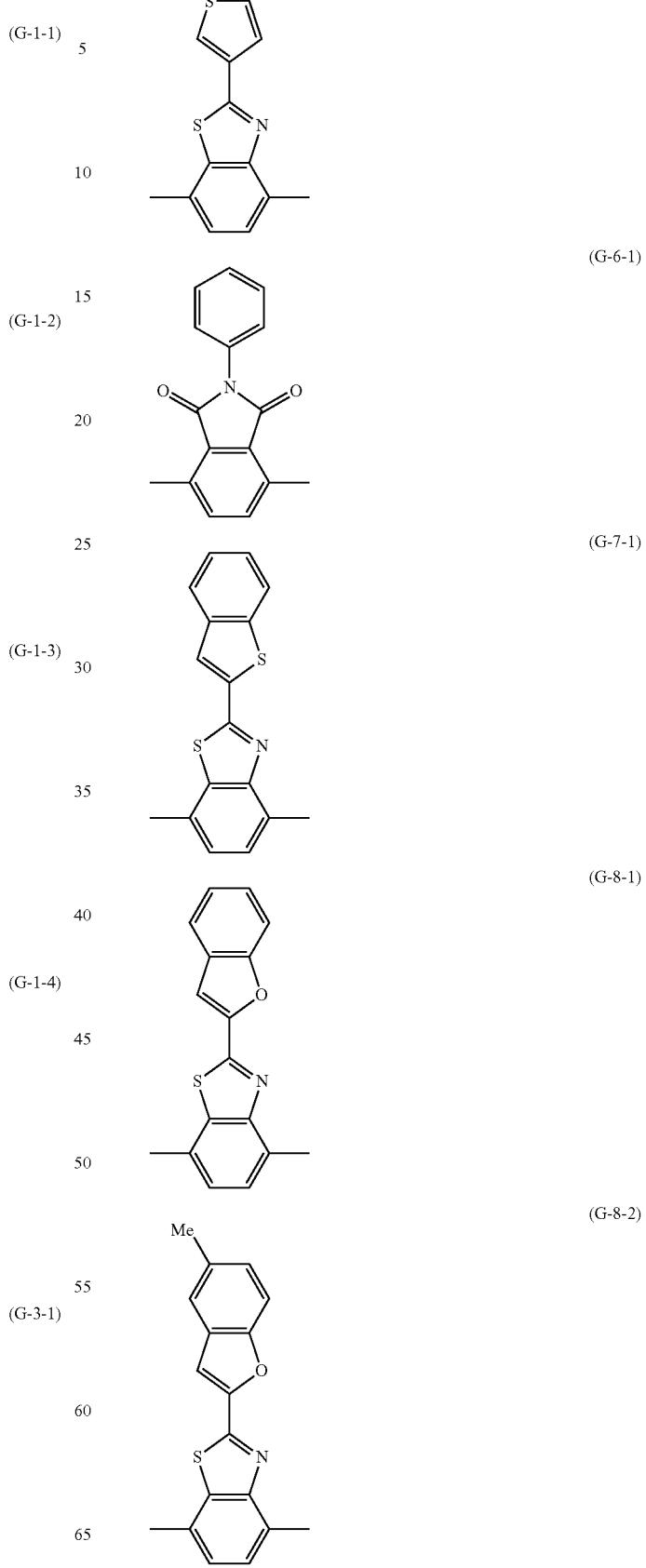

-continued
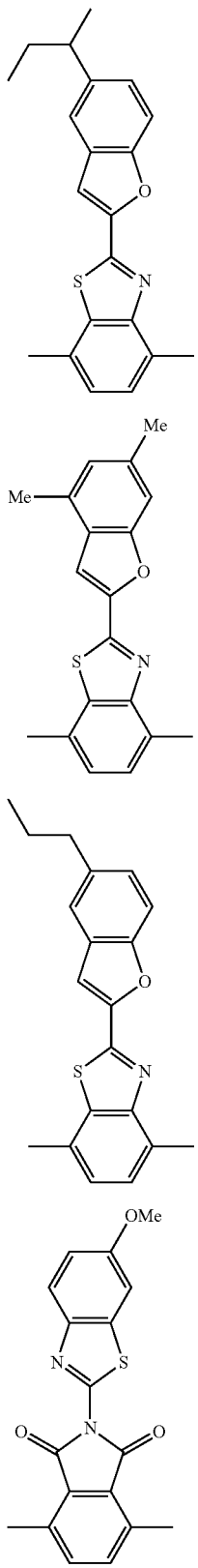
(G-8-2)
(G-8-3)
(G-8-4)
(G-10-1)
(wherein each of these groups may be mirror-inverted) is particularly preferable. In formula (G-11) to formula (G-22) above, Y more preferably represents a hydrogen atom, and r, s, t, and u more preferably each represent 0. A group selected from the following formula (G-11-1) to formula (G-20-1):
[Chem. 27]
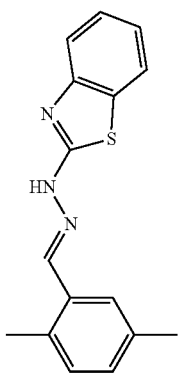
(G-11-1)
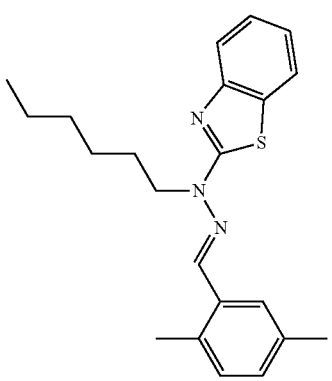
(G-11-2)
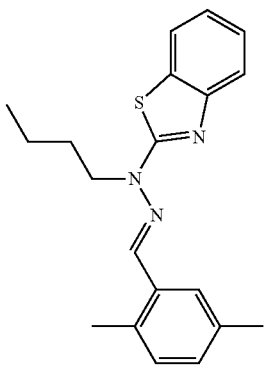
(G-11-3)
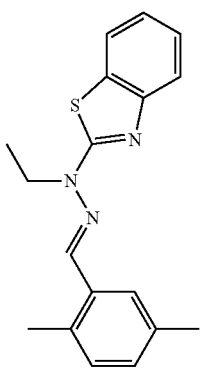
(G-11-4)

(G-11-5)
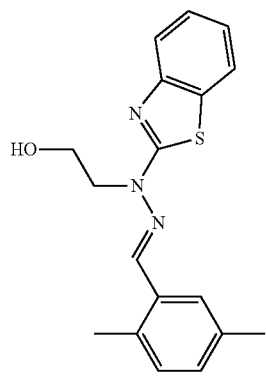
(G-11-6)
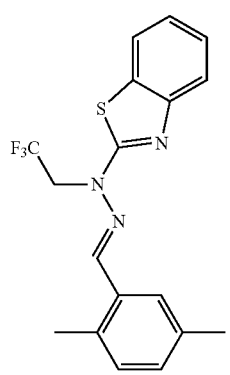
(G-11-7)
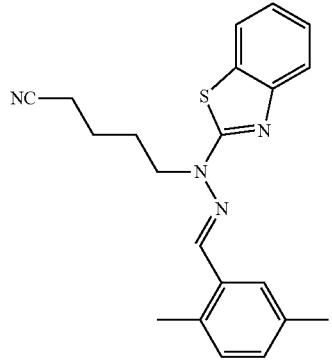
(G-11-8)
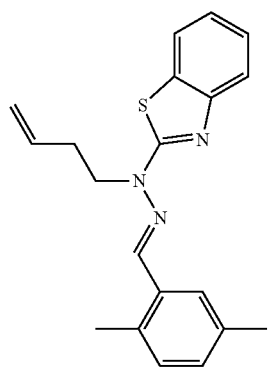
(G-11-9)
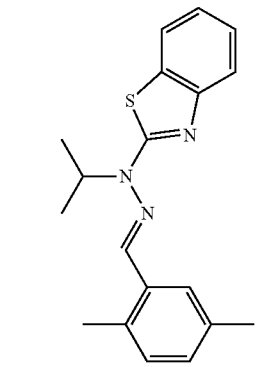
(G-11-10)
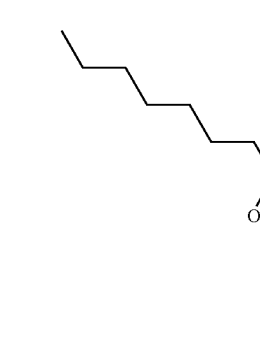
(G-11-11)
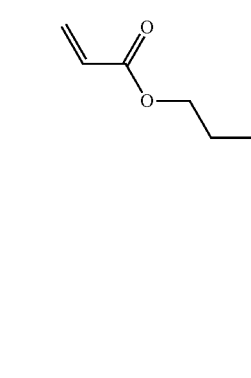
(G-11-12)
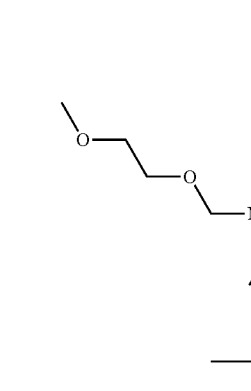

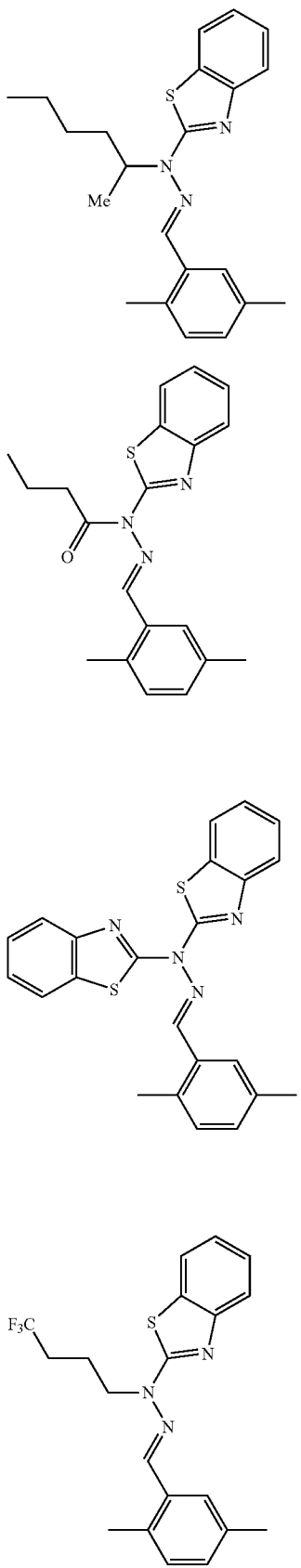
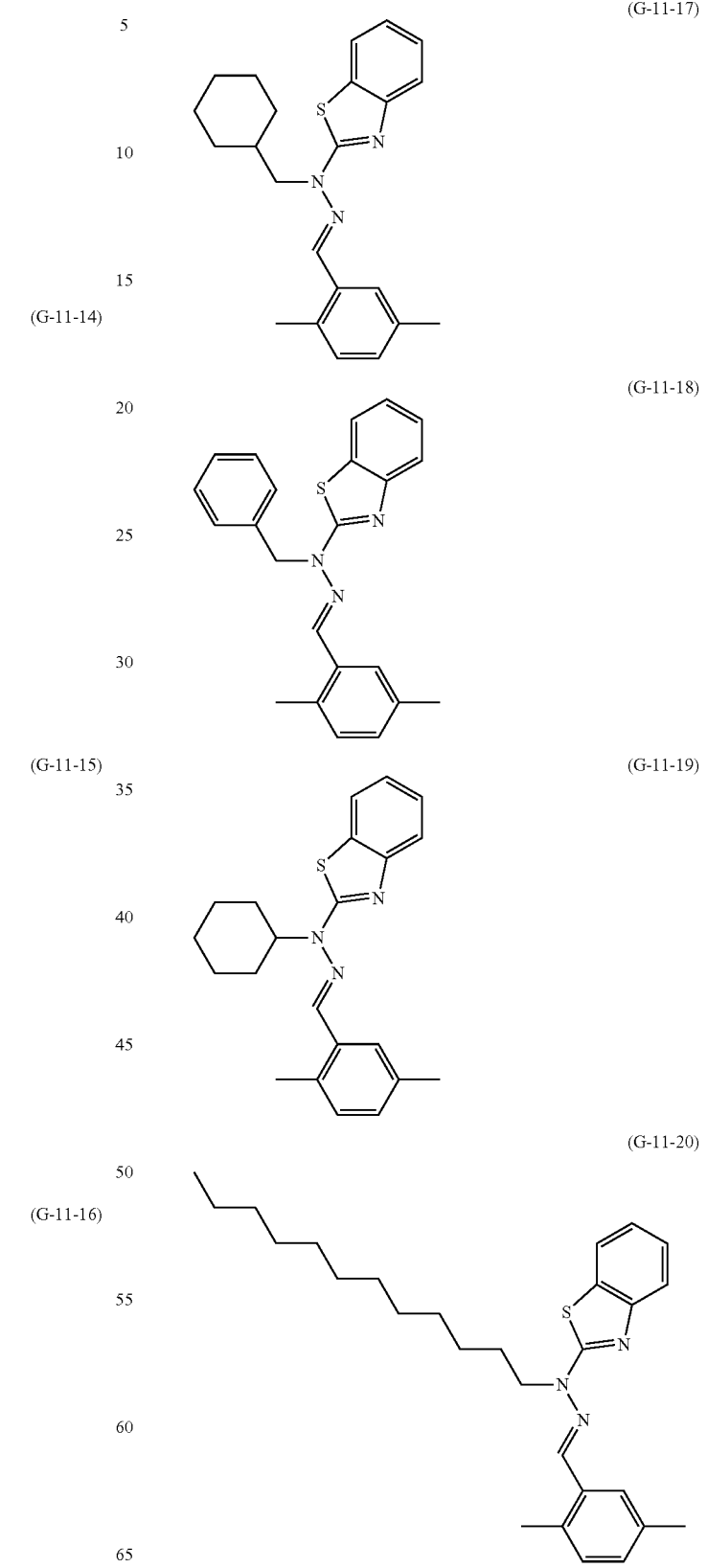

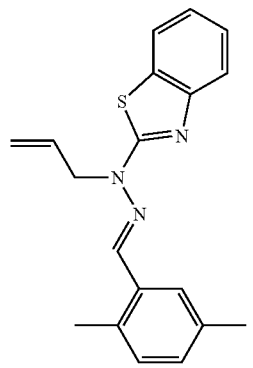 (G-11-21)
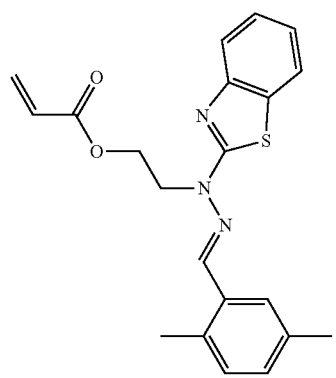 (G-11-22)
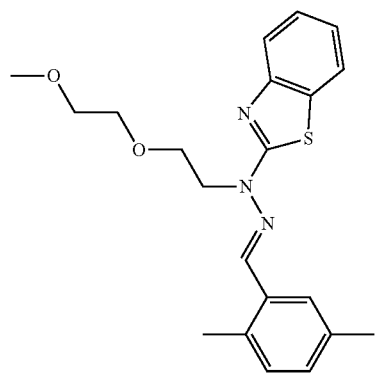 (G-11-23)
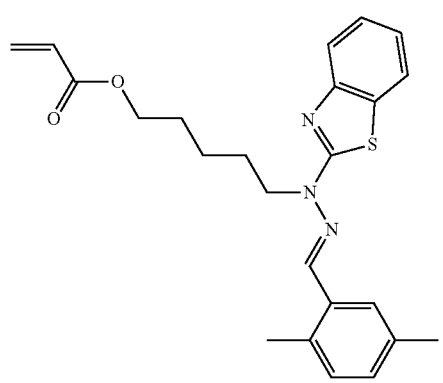 (G-11-24)
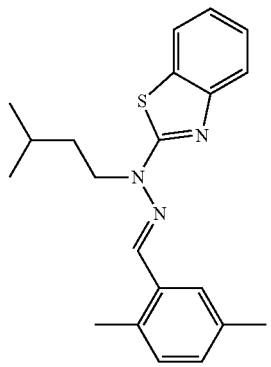 (G-11-25)
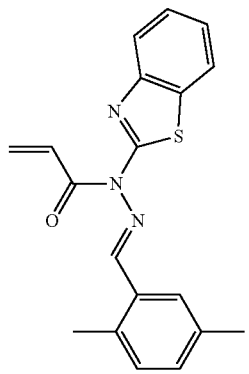 (G-11-26)
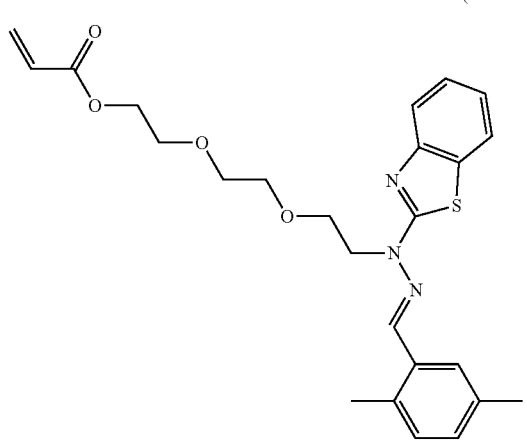 (G-11-27)
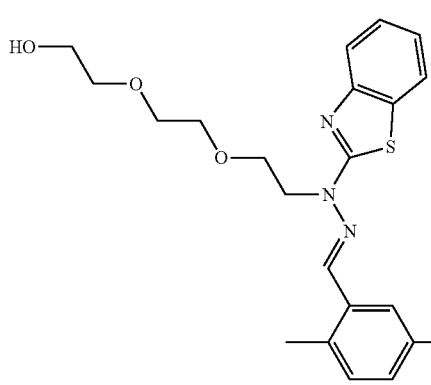 (G-11-28)

-continued (G-15-1)
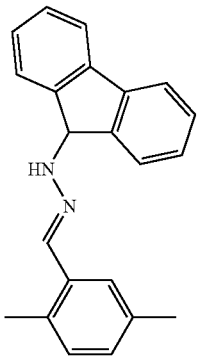

(G-16-1)
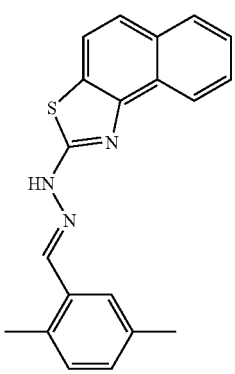

(G-17-1)
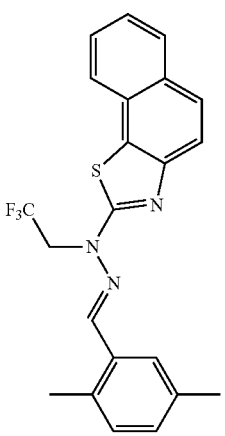

(G-20-1)
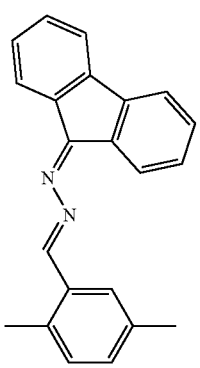

is particularly preferable.

In general formula (I), G1 may be a group represented by $A^G$. $A^G$ represents a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, a tetrahydropyran-2,5-diyl group, or a 1,3-dioxane-2,5-diyl group, and each of these groups is substituted by at least one substituent $L^{AG}$. From the viewpoint of ease of synthesis, solubility in a solvent, and liquid crystallinity, $A^G$ is preferably one of a 1,4-phenylene group, a 1,4-cyclohexylene group, and a naphthalene-2,6-diyl group that are substituted by at least one substituent $L^{AG}$, more preferably represents a group selected from the following formula (AG-1) to formula (AG-8):

[Chem. 29]

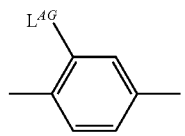 (AG-1)

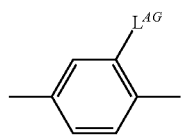 (AG-2)

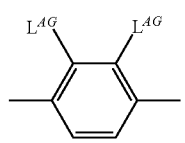 (AG-3)

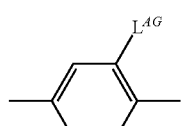 (AG-4)

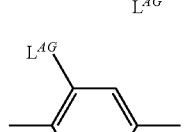 (AG-5)

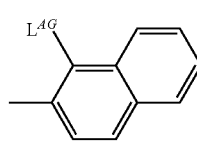 (AG-6)

 (AG-7)

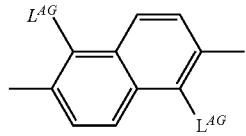 (AG-8)

still more preferably represents a group selected from formula (AG-1), formula (AG-2), formula (AG-6), and formula (AG-7), and particularly preferably represents a group selected from formula (AG-1) and formula (AG-2).

$L^{AG}$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group which has 1 to 20 carbon atoms and in which one —$CH_2$— group or two or more non-adjacent —$CH_2$— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom in the alkyl group being optionally replaced with a fluorine atom. Alternatively, $L^{AG}$ may represent a group represented by $P^{LAG}$-($Sp^{LAG}$-$X^{LAG}$)$_{kLAG}$—. Here, $P^{LAG}$ represents a polymerizable group and preferably represents a group polymerizable through radical polymerization, radical addition polymerization, cationic polymerization, or anionic polymerization, and $Sp^{LAG}$ represents a spacer group or a single bond. When a plurality of $Sp^{LAG}$s are present, they may be the same or different. $X^{LAG}$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond. When a plurality of $X^{LAG}$s are present, they may be the same or different (provided that $P^{LAG}$-($Sp^{LAG}$-$X^{LAG}$)$_{kLAG}$— contains no —O—O— bond). kLAG represents an integer from 0 to 10. When a plurality of $L^{AG}$s are present in the compound, they may be the same or different, and at least one $L^{AG}$ present in the compound represents a linear or branched alkyl group which has 1 to 20 carbon atoms, in which one —$CH_2$— group or two or more non-adjacent —$CH_2$— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and in which at least one —$CH_2$— group in the alkyl group is replaced with —CO—. From the viewpoint of ease of synthesis and availability of raw materials, $L^{AG}$ preferably represents a linear or branched alkyl group which has 1 to 20 carbon atoms, in which any hydrogen atom in the alkyl group is optionally replaced with a fluorine atom, in which one —$CH_2$— group or two or more non-adjacent —$CH_2$— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and in which at least one —$CH_2$— group in the alkyl group is replaced with —CO—. More preferably, LAG represents a linear alkyl group which has 1 to 20 carbon atoms, in which any hydrogen atom in the alkyl group is optionally replaced with a fluorine atom, in which one —$CH_2$— group or two or more non-adjacent —$CH_2$— groups are each independently optionally replaced with —O—, —S—, —CO—, —COO—, —OCO—, —CH=CH—, —CF=CF—, or —C≡C—, and in which at least one —$CH_2$— group in the alkyl group is replaced with —CO—. Still more preferably, LAG represents a linear alkyl group which has 1 to 20 carbon atoms, in which any hydrogen atom in the alkyl group is optionally replaced with a fluorine atom, in which one —$CH_2$— group or two or more non-adjacent —$CH_2$— groups are each independently optionally replaced with —O—, —S—, —CO—, —COO—, —OCO—, —CH=CH—, —CF=CF—, or —C≡C—, and in which a —$CH_2$— group at a terminal end is replaced with —CO—. Yet more preferably, $L^{AG}$ represents a linear alkyl group which has 1 to 20 carbon atoms and in which a —$CH_2$— group at a terminal end is replaced with —CO—. Yet still more preferably, $L^{AG}$ represents a linear alkyl group which has 1 to 10 carbon atoms and in which a —$CH_2$— group at a terminal end is replaced with —CO—. Particularly preferably, LAG represents a formyl group. The —$CH_2$— group at the terminal end is a —$CH_2$— group among the —$CH_2$— groups in $L^{AG}$ that is bonded directly to $A^G$.

In general formula (I), when $G^1$ is a group represented by $C^G$, the group represented by $C^G$ is a group which has a chiral structure and may be unsubstituted or substituted by at least one substituent $L^{CG}$. $C^G$ preferably represents a group selected from the following formula (C-1) to formula (C-4):

[Chem. 30]

(C-1)

(C-2)

(C-3)

(C-4)

(wherein each of these groups may have a bond at any position; each —$CH_2$— is independently optionally replaced with —O—, —S—, —$NR^T$— (wherein $R^T$ represents a hydrogen atom or an alkyl group having 1 to 20 carbon atoms), —CS— or —CO—; and each of these groups may be unsubstituted or substituted by at least one substituent $L^G$) or represents a group selected from the following formula (C-5) to formula (C-12):

[Chem. 31]

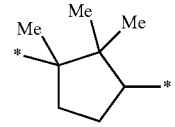
(C-5)

-continued

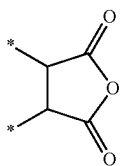
(C-6)

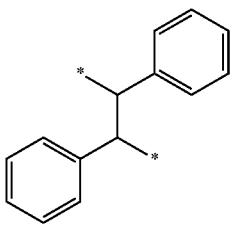
(C-7)

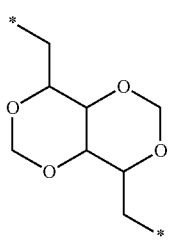
(C-8)

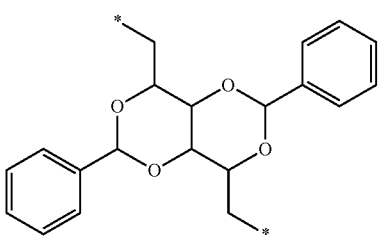
(C-9)

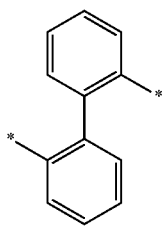
(C-10)

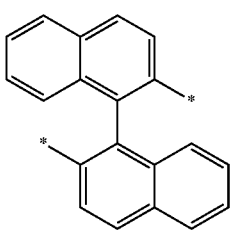
(C-11)

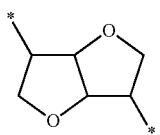
(C-12)

(wherein each of these groups is bonded to groups represented by $Z^1$ and $Z^2$ at respective positions indicated by *, and each of these groups may be unsubstituted or substituted by at least one substituent $L^{CG}$). From the viewpoint of yield and quality, $C^G$ more preferably represents a group selected from formula (C-1) to formula (C-4), formula (C-10), formula (C-11), and formula (C-12) which may be unsubstituted or substituted by at least one substituent $L^{CG}$, still more preferably a group selected from formula (C-10) which may be unsubstituted or substituted by at least one substituent $L^{CG}$, and particularly preferably a group represented by formula (C-12) above.

From the viewpoint of ease of synthesis, availability of raw materials, and liquid crystallinity, $L^{CG}$ preferably represents a fluorine atom, a chlorine atom, a pentafluorosulfuranyl group, a nitro group, a cyano group, a methylamino group, a dimethylamino group, a diethylamino group, a diisopropylamino group, or a linear or branched alkyl group which has 1 to 20 carbon atoms, in which any hydrogen atom is optionally replaced with a fluorine atom, and in which one —$CH_2$— group or non-adjacent two or more —$CH_2$— groups are each independently optionally replaced with a group selected from —O—, —S—, —CO—, —COO—, —OCO—, —O—CO—O—, —CH=CH—, —CF=CF—, and —C≡C—. More preferably, $L^{CG}$ represents a fluorine atom, a chlorine atom, or a linear or branched alkyl group which has 1 to 12 carbon atoms, in which any hydrogen atom is optionally replaced with a fluorine atom, and in which one —$CH_2$— group or non-adjacent two or more —$CH_2$— groups are each independently optionally replaced with a group selected from —O—, —COO—, and —OCO—. Still more preferably, $L^{CG}$ represents a fluorine atom, a chlorine atom, or a linear or branched alkyl or alkoxy group which has 1 to 12 carbon atoms and in which any hydrogen atom is optionally replaced with a fluorine atom. Particularly preferably, $L^{CG}$ represents a fluorine atom, a chlorine atom, or a linear alkyl or alkoxy group having 1 to 8 carbon atoms.

In general formula (I), m1 and m2 each independently represent an integer from 0 to 8. From the viewpoint of liquid crystallinity, solubility, ease of synthesis, and availability of raw materials, m1 and m2 each independently preferably represent an integer from 0 to 6, each independently more preferably represent an integer from 0 to 4, each independently still more preferably represent an integer from 1 to 3, and each independently particularly preferably represent an integer of 1 or 2.

In the esterification step, the same conditions as the well-known reaction conditions when a condensing agent is used can be used. Specifically, the reaction solvent is preferably an aprotic solvent. Examples of the aprotic solvent include chloroform, dichloromethane, 1,2-dichloroethane, acetone, acetonitrile, N,N-dimethylformamide, N,N-dimethylacetamide, dimethyl sulfoxide, diethyl ether, xylene, ethyl acetate, butyl acetate, propyl acetate, methyl acetate, cyclohexanone, 1,4-dioxane, dichloromethane, styrene, tetrahydrofuran, pyridine, 1-methyl-2-pyrrolidinone, toluene, hexane, cyclohexane, heptane, benzene, methyl isobutyl ketone, tert-butyl methyl ether, and methyl ethyl ketone. When the content of water in the reaction system is high, it is preferable to use a solvent with low solubility in water in order to prevent deactivation of the condensing agent by water. Example of the solvent in this case include chloroform, dichloromethane, 1,2-dichloroethane, xylene, ethyl acetate, butyl acetate, propyl acetate, methyl acetate, cyclohexanone, dichloromethane, styrene, toluene, hexane, cyclohexane, heptane, and benzene. The reaction temperature in the esterification step is preferably −80° C. to 200° C., more preferably −50° C. to 150° C., sill more preferably −20° C. to 120° C., yet more preferably 0° C. to 60° C., and particularly preferably room temperature.

It is preferable from the viewpoint of stability of the condensing agent to remove water from the reaction system as much as possible. More preferably, the reaction is performed in dry air. Particularly preferably, the reaction is performed in an inert gas atmosphere such as nitrogen or argon.

After the esterification step, purification may be performed as needed. Examples of the purification method include chromatography, recrystallization, distillation, sublimation, reprecipitation, adsorption, filtration, and liquid separation treatment. When a purification agent is used, the purification agent may be silica gel, alumina, activated carbon, activated clay, celite, zeolite, mesoporous silica, carbon nanotubes, carbon nanohorns, bincho charcoal, charcoal, graphene, ion-exchanged resins, Japanese acid clay, silicon dioxide, diatomaceous earth, perlite, cellulose, organic polymers, porous gel, etc.

In the esterification step, the same conditions as the well-known reaction conditions when a condensing agent is used can be used. Specifically, the reaction solvent is preferably an aprotic solvent. Examples of the aprotic solvent include chloroform, dichloromethane, 1,2-dichloroethane, acetone, acetonitrile, N,N-dimethylformamide, N,N-dimethylacetamide, dimethyl sulfoxide, diethyl ether, xylene, ethyl acetate, butyl acetate, propyl acetate, methyl acetate, cyclohexanone, 1,4-dioxane, dichloromethane, styrene, tetrahydrofuran, pyridine, 1-methyl-2-pyrrolidinone, toluene, hexane, cyclohexane, heptane, benzene, methyl isobutyl ketone, tert-butyl methyl ether, and methyl ethyl ketone. When the content of water in the reaction system is high, it is preferable to use a solvent with low solubility in water in order to prevent deactivation of the condensing agent by water. Example of the solvent in this case include chloroform, dichloromethane, 1,2-dichloroethane, xylene, ethyl acetate, butyl acetate, propyl acetate, methyl acetate, cyclohexanone, dichloromethane, styrene, toluene, hexane, cyclohexane, heptane, and benzene. The reaction temperature in the esterification step is preferably −80° C. to 200° C., more preferably −50° C. to 150° C., sill more preferably −20° C. to 120° C., yet more preferably 0° C. to 60° C., and particularly preferably room temperature.

It is preferable from the viewpoint of stability of the condensing agent to remove water from the reaction system as much as possible. More preferably, the reaction is performed in dry air. Particularly preferably, the reaction is performed in an inert gas atmosphere such as nitrogen or argon.

After the esterification step, purification may be performed as needed. Examples of the purification method include chromatography, recrystallization, distillation, sublimation, reprecipitation, adsorption, filtration, and liquid separation treatment. When a purification agent is used, the purification agent may be silica gel, alumina, activated carbon, activated clay, celite, zeolite, mesoporous silica, carbon nanotubes, carbon nanohorns, bincho charcoal, charcoal, graphene, ion-exchanged resins, Japanese acid clay, silicon dioxide, diatomaceous earth, perlite, cellulose, organic polymers, porous gel, etc.

In the production method of the present invention, the reaction mixture obtained in the mixing step is used to perform the esterification step. Therefore, the amount of by-product derived from the condensing agent can be smaller than that formed when a conventional production method is used. In particular, when a compound having a carbodiimide structure is used as the condensing agent, the amount of N-acylurea formed as a by-product can be significantly smaller than that when a conventional production method is used. In this case, no particular limitation is imposed on the amount of the N-acylurea formed, and the amount varies depending on the reaction system. The upper limit of the amount of the N-acylurea formed relative to the theoretical yield of the ester group-containing compound, which is the product, is 5.0% or less, preferably 2.0% or less, and more preferably 1.5% or less, and the lower limit is 0.1% or more.

With the production method of the present invention, since the formation of the by-product can be reduced as described above, the yield of the ester group-containing compound can be improved. In this case, the lower limit of the yield of the ester group-containing compound with respect to the theoretical yield may be 75% or more, preferably 80% or more, more preferably 85% or more, and still more preferably 90% or more, and the upper limit may be 99.9% or less.

The present invention encompasses the ester group-containing compound produced by the production method of the present invention and a derivative produced using the compound as a synthetic intermediate.

The ester group-containing compound or the derivative thereof is preferably the compound represented by general formula (I) above. No particular limitation is imposed on the derivative of the ester group-containing compound, so long as it is produced by using, as the synthetic intermediate, the ester group-containing compound obtained through the esterification step. Preferably, the derivative is the compound represented by general formula (I) above, as is the ester group-containing compound.

It is preferable that the ester group-containing compound or the derivative thereof has a polymerizable group, in order that a polymerizable composition can be easily formed. The polymerizable group is preferably the group represented by $P^1$ above.

It is preferable that the ester group-containing compound or the derivative thereof has liquid crystallinity, in order that a liquid crystal composition can be easily formed.

When the ester group-containing compound or the derivative thereof is used as a raw material of a polymer, the heat resistance and lightfastness of the polymer can be improved. The reason for this is unclear. However, this may be because, in the ester group-containing compound of the present invention or the derivative thereof, the content of impurities formed during the esterification step is low. Examples of the impurities include an N-acylurea produced as a by-product when a compound having a carbodiimide structure is used as the condensing agent. Examples of the N-acylurea include compounds represented by the following formula (a-4-1) and formula (a-4-2):

[Chem. 32]

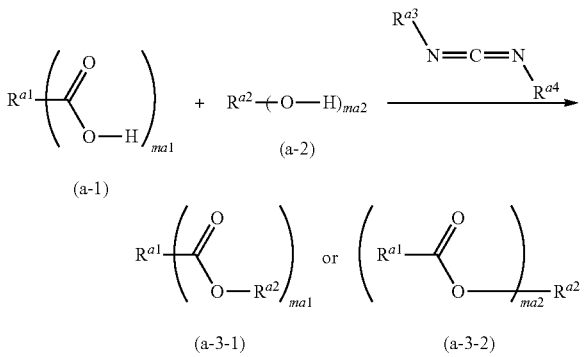

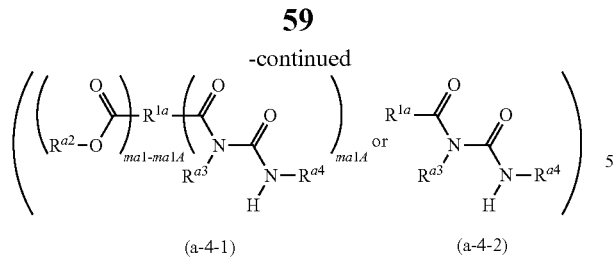

(a-4-1)  (a-4-2)

(wherein $R^{a1}$ and $R^{a2}$ have the same meanings as $R^{a1}$ in general formula (a-1) and $R^{a2}$ in general formula (a-2), respectively; ma1 and ma2 have the same meanings as ma1 in general formula (a-1) and ma2 in general formula (a-2), respectively; $R^{a3}$ and $R^{a4}$ represent substituents in carbodiimide; in formula (a-4-1) and formula (a-4-2), $R^{a3}$ and $R^{a4}$ may be exchanged with each other; and ma1A represents an integer from 1 to 20). $R^{a3}$ and $R^{a4}$ may each be a hydrogen atom or an organic group having 1 to 100 carbon atoms.

A preferred embodiment of the present invention is production of a derivative of an ester group-containing compound that is suitable for a raw material of a polymerizable liquid crystal composition. Specifically, the present invention encompasses a method for producing a derivative of an ester group-containing compound, the method including: a first production step of mixing a condensing agent, a Bronsted acid, a carboxylic acid, and a phenol or an alcohol to prepare a reaction mixture and then subjecting the carboxylic acid and the phenol or alcohol to a condensation reaction in the reaction mixture to thereby obtain a synthetic intermediate that is a compound represented by general formula (I-i):

[Chem. 33]

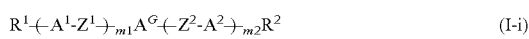
(I-i)

(wherein $R^1$, $R^2$, $A^1$, $A^2$, $Z^1$, $Z^2$, m1, and m2 have the same meanings as $R^1$, $R^2$, $A^1$, $A^2$, $Z^1$, $Z^2$, m1, and m2, respectively, in general formula (I), and $A^G$ has the same meaning as $A^G$ in general formula (I)); and a second production step of obtaining, from the synthetic intermediate, a compound represented by general formula (I-ii):

[Chem. 34]

(I-ii)

(wherein $R^1$, $R^2$, $A^1$, $A^2$, $Z^1$, $Z^2$, m1, and m2 have the same meanings as $R^1$, $R^2$, $A^1$, $A^2$, $Z^1$, $Z^2$, m1, and m2, respectively, in general formula (I), and M is a group selected from the following formula (M-1) to formula (M-6):

[Chem. 35]

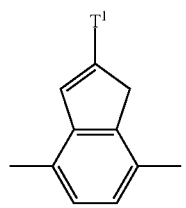
(M-1)

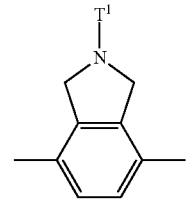
(M-2)

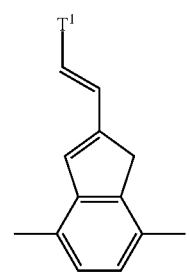
(M-3)

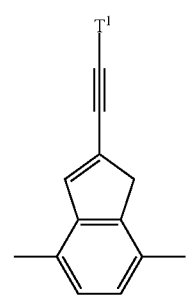
(M-4)

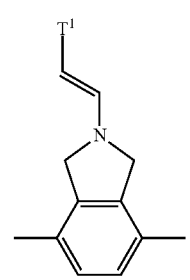
(M-5)

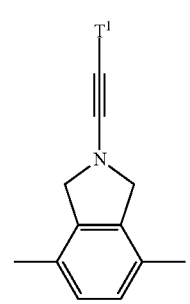
(M-6)

(wherein each of these groups may be unsubstituted or substituted by at least one substituent $L^{G1}$ described above; each —CH= is independently optionally replaced with —N=; each —CH$_2$— is independently optionally replaced with —O—, —S—, —NR$^T$— (wherein $R^T$ represents a hydrogen atom or an alkyl group having 1 to 20 carbon atoms), —CS—, or —CO—; and $T^1$ represents a group selected from the following formula (T1-1) to formula (T1-6):

[Chem. 36]

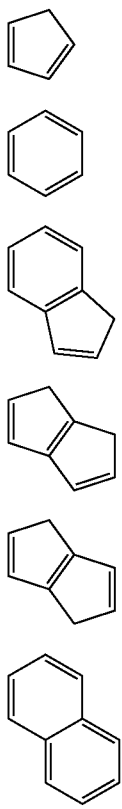

(T1-1)

(T1-2)

(T1-3)

(T1-4)

(T1-5)

(T1-6)

(wherein each of these groups may have a bond at any position; each —CH= is independently optionally replaced with —N=; each —CH$_2$— is independently optionally replaced with —O—, —S—, —NR$^T$— (wherein R$^T$ represents a hydrogen atom or an alkyl group having 1 to 20 carbon atoms), —CS—, or —CO—; the phrase "each of these groups may have a bond at any position" means that, when, for example, formula (T1-1) is bonded to T$^1$ of one of formula (M-1) to formula (M-6), formula (T1-1) may have one bond at any position (as for the phrase "each of these groups may have a bond at any position" in the following description of the present invention, the same meaning applies); and each of these groups may be unsubstituted or substituted by at least one substituent L$^{G1}$ described above)) or the following formula (M-7) to formula (M-14):

[Chem. 37]

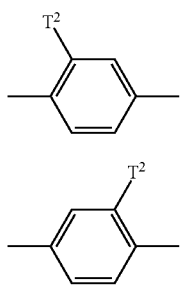

(M-7)

(M-8)

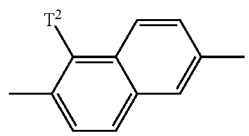

(M-9)

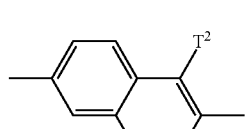

(M-10)

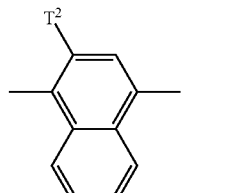

(M-11)

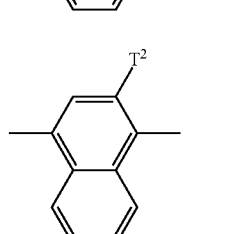

(M-12)

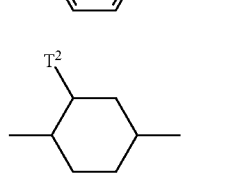

(M-13)

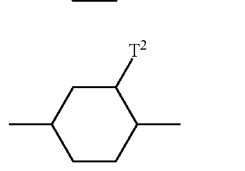

(M-14)

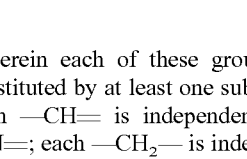

(wherein each of these groups may be unsubstituted or substituted by at least one substituent L$^{G1}$ described above; each —CH= is independently optionally replaced with —N=; each —CH$_2$— is independently optionally replaced with —O—, —S—, —NR$^T$— (wherein R$^T$ represents a hydrogen atom or an alkyl group having 1 to 20 carbon atoms), —CS—, or —CO—; and T$^2$ represents a group selected from the following formula (T2-1) and formula (T2-2):

[Chem. 38]

(T2-1)

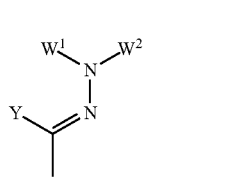

-continued (T2-2)

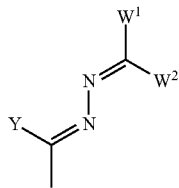

(wherein $W^1$ represents a group containing an optionally substituted aromatic group having 1 to 40 carbon atoms and/or an optionally substituted non-aromatic group having 1 to 40 carbon atoms; the aromatic group may be a hydrocarbon ring or a heterocycle; the non-aromatic group may be a hydrocarbon group or a hydrocarbon group in which any carbon atom in the group is replaced with a heteroatom (provided that no oxygen atoms are bonded directly to each other), wherein $W^2$ represents a hydrogen atom or a linear or branched alkyl group which has 1 to 20 carbon atoms and in which one —$CH_2$— group or two or more non-adjacent —$CH_2$— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom in the alkyl group being optionally replaced with a fluorine atom, wherein, alternatively, $W^2$ may represent a group having at least one aromatic group and having 2 to 30 carbon atoms (excluding carbon atoms in the aromatic group), and the group may be unsubstituted or substituted by at least one substituent $L^W$, wherein, alternatively, $W^2$ may represent a group represented by $P^W$-($Sp^W$-$X^W$)$_{kW}$— wherein $P^W$ represents a polymerizable group; preferred polymerizable groups are as defined above for $P^1$; $Sp^W$ represents a spacer group or a single bond; preferred spacer groups are as defined above for $Sp^1$; when a plurality of $Sp^W$s are present, they may be the same or different; $X^W$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond; when a plurality of $X^W$s are present, they may be the same or different (provided that $P^W$-($Sp^W$-$X^W$)$_{kW}$— contains no —O—O— bond); and kW represents an integer from 0 to 10, wherein $L^W$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group which has 1 to 20 carbon atoms and in which one —$CH_2$— group or two or more non-adjacent —$CH_2$— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom in the alkyl group being optionally replaced with a fluorine atom, wherein, alternatively, $L^W$ may represent a group represented by $P^{LW}$-($Sp^{LW}$-$X^{LW}$)$_{kLW}$— wherein $P^{LW}$ represents a polymerizable group and preferably represents a group polymerizable through radical polymerization, radical addition polymerization, cationic polymerization, or anionic polymerization; $Sp^{LW}$ represents a spacer group or a single bond; when a plurality of $Sp^{LW}$s are present, they may be the same or different; $X^{LW}$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond; when a plurality of $X^{LW}$s are present, they may be the same or different (provided that $P^{LW}$-($Sp^{LW}$-$X^{LW}$)$_{kLW}$— contains no —O—O— bond); kLW represents an integer from 0 to 10; and, when a plurality of $L^W$s are present in the compound, they may be the same or different, wherein Y represents a hydrogen atom, a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group which has 1 to 20 carbon atoms and in which one —$CH_2$— group or two or more non-adjacent —$CH_2$— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom in the alkyl group being optionally replaced with a fluorine atom, and wherein, alternatively, Y may represent a group represented by $P^Y$-($Sp^Y$-$X^Y$)$_{kY}$— wherein $P^Y$ represents a polymerizable group and preferably represents a group polymerizable through radical polymerization, radical addition polymerization, cationic polymerization, or anionic polymerization; preferred polymerizable groups are as defined above for $P^1$; $Sp^Y$ represents a spacer group or a single bond; preferred spacer groups are as defined above for $Sp^1$; when a plurality of $Sp^Y$s are present, they may be the same or different; $X^Y$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond; when a plurality of $X^Y$s are present, they may be the same or different (provided that $P^Y$-($Sp^Y$-$X^Y$)$_{kY}$— contains no —O—O— bond); kY represents an integer from 0 to 10; and $W^1$ and $W^2$ may together form a ring structure)).

The compound represented by general formula (I-i):

[Chem. 39]

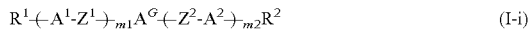

(I-i)

(wherein $R^1$, $R^2$, $A^1$, $A^2$, $Z^1$, $Z^2$, m1, and m2 have the same meanings as $R^1$, $R^2$, $A^1$, $A^2$, $Z^1$, $Z^2$, m1, and m2, respectively, in general formula (I), and $A^G$ has the same meaning as $A^G$ in general formula (I)) is preferably a compound represented by the following general formula (I-i-1):

[Chem. 40]

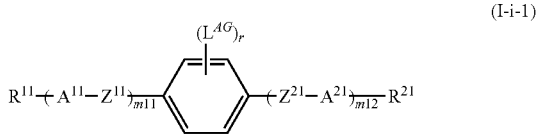

(I-i-1)

(wherein $R^{11}$, $R^{21}$, $A^{11}$, $A^{21}$, $Z^{11}$, $Z^{21}$, and $L^{AG}$ have the same meanings as $R^1$, $R^2$, $A^1$, $A^2$, $Z^1$, $Z^2$, and $L^{AG}$, respectively, in general formula (I); m11 and m21 each independently represent an integer from 0 to 4; and r represents an integer from 0 to 4), is more preferably a compound represented by the following general formula (I-i-1-1):

[Chem. 41]

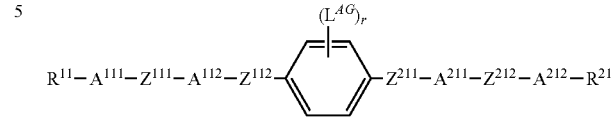

(I-i-1-1)

(wherein $R^{11}$, $R^{21}$, and $L^{AG}$ have the same meanings as $R^1$, $R^2$, and $L^{AG}$, respectively, in general formula (I); r represents an integer from 0 to 4; $A^{111}$ and $A^{212}$ each independently represent a 1,4-cyclohexylene group optionally substituted by a substituent L or a 1,4-phenylene group optionally substituted by a substituent L; $A^{112}$ and $A^{211}$ each independently represent a 1,4-cyclohexylene group optionally substituted by a substituent L; $Z^{111}$ and $Z^{212}$ each independently represent —OCH$_2$—, —CH$_2$O—, —COO—, —OCO—, or a single bond; $Z^{112}$ and $Z^{211}$ each independently represent —OCH$_2$—, —CH$_2$O—, —COO—, or —OCO—; and at least one of $Z^{111}$, $Z^{212}$, $Z^{112}$, and $Z^{211}$ represents a group selected from —COO— and —OCO—), is still more preferably a compound represented by the following general formula (I-i-1-1-1):

[Chem. 42]

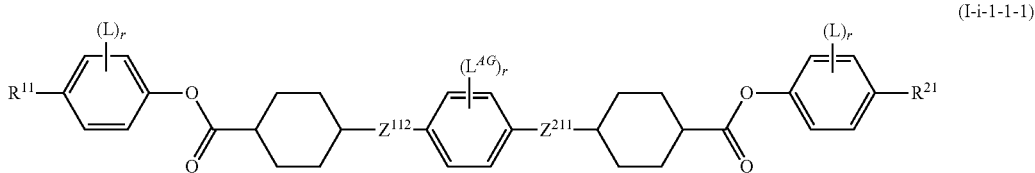

(I-i-1-1-1)

(wherein $R^{11}$, $R^{21}$, L, and $L^{AG}$ have the same meanings as $R^1$, $R^2$, L, and $L^{AG}$, respectively, in general formula (I); each r independently represents an integer from 0 to 4; and $Z^{112}$ and $Z^{211}$ each independently represent —OCH$_2$—, —CH$_2$O—, —COO—, or —OCO—), is yet more preferably a compound represented by the following general formula (I-i-1-1-1-1):

[Chem. 43]

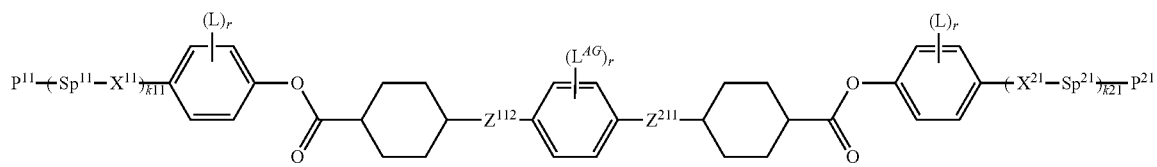

(I-i-1-1-1-1)

(wherein $P^{11}$ and $P^{21}$ have the same meanings as $P^1$ and $P^2$, respectively; $Sp^{11}$ and $Sp^{21}$ have the same meanings as $Sp^1$ and $Sp^2$, respectively; $X^{11}$ and $X^{21}$ have the same meanings as $X^1$ and $X^2$, respectively; k11 and k21 have the same meanings as k1 and k2, respectively; L has the same meaning as L in general formula (I); $L^{AG}$ has the same meaning as $L^{AG}$ in general formula (I); each r independently represents an integer from 0 to 4; and $Z^{112}$ and $Z^{211}$ each independently represent —OCH$_2$—, —CH$_2$O—, —COO—, or —OCO—), and is particularly preferably a group represented by the following general formula (I-i-1-1-1-1-1):

[Chem. 44]

(I-i-1-1-1-1-1)

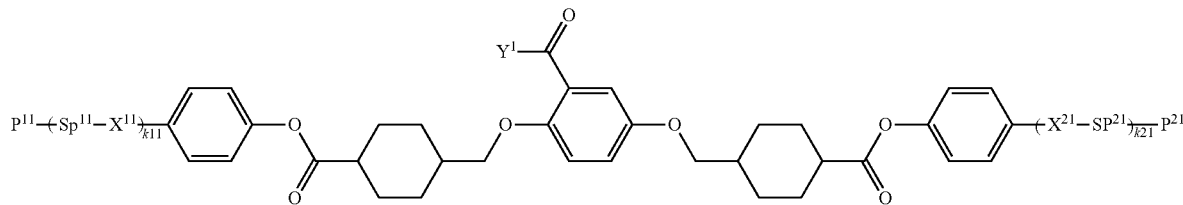

(wherein $P^{11}$ and $P^{21}$ have the same meanings as $P^1$ and $P^2$, respectively; $Sp^{11}$ and $Sp^{21}$ have the same meanings as $Sp^1$ and $Sp^2$, respectively; $X^{11}$ and $X^{21}$ have the same meanings as $X^1$ and $X^2$, respectively; k11 and k21 have the same meanings as k1 and k2, respectively; and $Y^1$ represents a hydrogen atom). In formulas (I-i) to (I-i-1-1-1-1) above, a preferred structure of $L^{AG}$ is as described above.

Specifically, the compound represented by general formula (I-ii)

[Chem. 45]

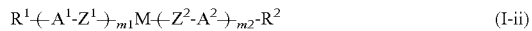 (I-ii)

(wherein $R^1$, $R^2$, $A^1$, $A^2$, $Z^1$, $Z^2$, m1, and m2 have the same meanings as $R^1$, $R^2$, $A^1$, $A^2$, $Z^1$, $Z^2$, m1, and m2, respectively, in general formula (I), and M represents a group selected from formula (M-1) to formula (M-14) above) is preferably a compound represented by the following general formula (I-ii-1):

[Chem. 46]

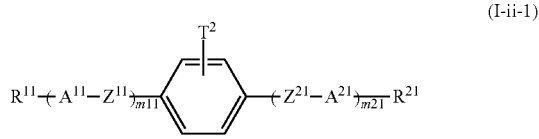 (I-ii-1)

(wherein $R^{11}$, $R^{21}$, $A^{11}$, $A^{21}$, $Z^{11}$, and $Z^{21}$ have the same meanings as $R^1$, $R^2$, $A^1$, $A^2$, $Z^1$ and $Z^2$, respectively, in general formula (I); m11 and m21 each independently represent an integer from 0 to 4; and $T^2$ has the same meaning as formula (T2-1) or formula (T2-2) above), is more preferably a compound represented by the following general formula (I-ii-1-1):

[Chem. 47]

(I-ii-1-1)

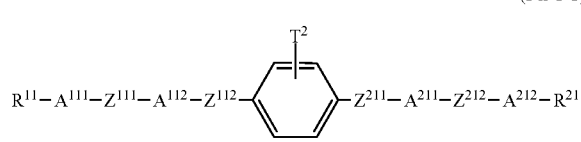

(wherein $R^{11}$ and $R^{21}$ have the same meanings as $R^1$ and $R^2$, respectively, in general formula (I); $T^2$ has the same meaning as formula (T2-1) or formula (T2-2) above; $A^{111}$ and $A^{212}$ each independently represent a 1,4-cyclohexylene group optionally substituted by a substituent L or a 1,4-phenylene group optionally substituted by a substituent L; $A^{112}$ and $A^{211}$ each independently represent a 1,4-cyclohexylene group optionally substituted by a substituent L; $Z^{111}$ and $Z^{212}$ each independently represent —OCH$_2$—, —CH$_2$O—, —COO—, —OCO—, or a single bond; $Z^{112}$ and $Z^{211}$ each independently represent —OCH$_2$—, —CH$_2$O—, —COO—, or —OCO—; and at least one of $Z^{111}$, $Z^{212}$, $Z^{112}$, and $Z^{211}$ represents a group selected from —COO— and —OCO—), is still more preferably a compound represented by the following general formula (I-ii-1-1-1):

[Chem. 48]

(I-ii-1-1-1)

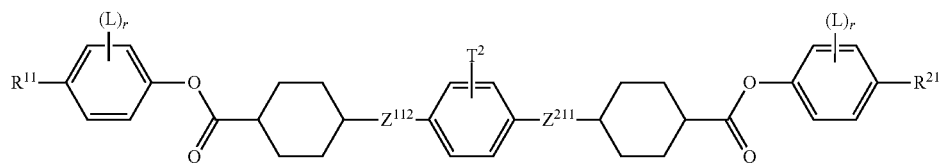

(wherein $R^{11}$, $R^{21}$, and L have the same meanings as $R^1$, $R^2$, and L, respectively, in general formula (I); $T^2$ has the same meaning as formula (T2-1) or formula (T2-2) above; each r independently represents an integer from 0 to 4; and $Z^{112}$ and $Z^{211}$ each independently represent —OCH$_2$—, —CH$_2$O—, —COO—, or —OCO—), is yet more preferably a compound represented by the following general formula (I-ii-1-1-1):

[Chem. 49]

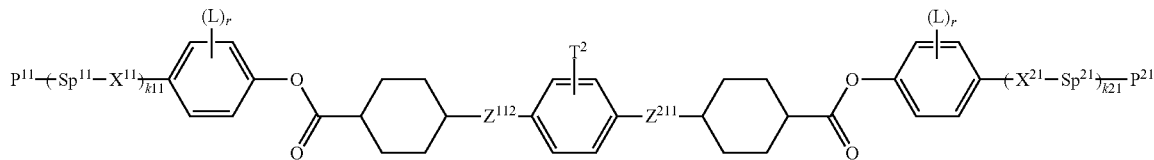

(I-ii-1-1-1-1)

(wherein $P^{11}$ and $P^{21}$ have the same meanings as $P^1$ and $P^2$, respectively; $Sp^{11}$ and $Sp^{21}$ have the same meanings as $Sp^1$ and $Sp^2$, respectively; $X^{11}$ and $X^{21}$ have the same meanings as $X^1$ and $X^2$, respectively; k11 and k21 have the same meanings as k1 and k2, respectively; L has the same meaning as L in general formula (I); each r independently represents an integer from 0 to 4; $T^2$ has the same meaning as formula (T2-1) or formula (T2-2) above; and $Z^{112}$ and $Z^{211}$ each independently represent —OCH$_2$—, —CH$_2$O—, —COO—, or —OCO—), is still yet more preferably a group represented by the following general formula (I-ii-1-1-1-2):

[Chem. 50]

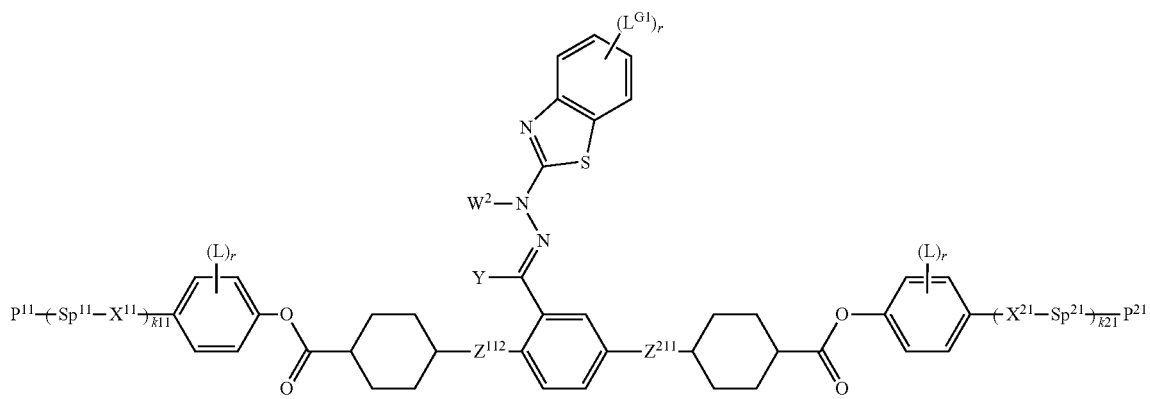

(I-ii-1-1-1-2)

(wherein $P^{11}$ and $P^{21}$ have the same meanings as $P^1$ and $P^2$, respectively; $Sp^{11}$ and $Sp^{21}$ have the same meanings as $Sp^1$ and $Sp^2$, respectively; $X^{11}$ and $X^{21}$ have the same meanings as $X^1$ and $X^2$, respectively; k11 and k21 have the same meanings as k1 and k2, respectively; L has the same meaning as L in general formula (I); $L^{G1}$ has the same meaning as $L^{G1}$ in general formula (I); each r independently represents an integer from 0 to 4; Y and $W^2$ have the same meanings as Y and $W^2$, respectively, in formula (T2-1) or formula (T2-2); and $Z^{112}$ and $Z^{211}$ each independently represent —OCH$_2$—, —CH$_2$O—, —COO—, or —OCO—), and is particularly preferably a compound represented by the following general formula (I-ii-1-1-1-2-1):

[Chem. 51]

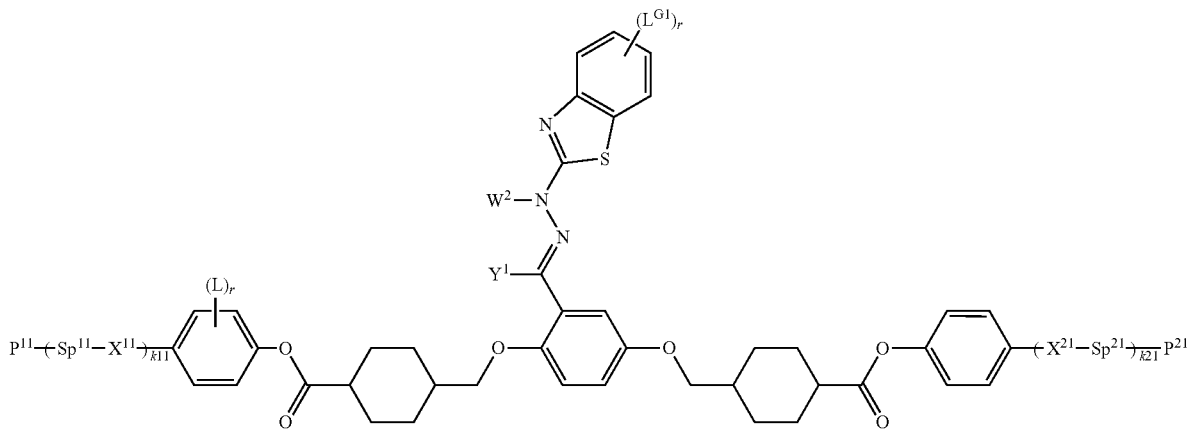

(I-ii-1-1-1-2-1)

(wherein $P^{11}$ and $P^{21}$ have the same meanings as $P^1$ and $P^2$, respectively; $Sp^{11}$ and $Sp^{21}$ have the same meanings as $Sp^1$ and $Sp^2$, respectively; $X^{11}$ and $X^{21}$ have the same meanings as $X^1$ and $X^2$, respectively; k11 and k21 have the same meanings as k1 and k2, respectively: $L^{G1}$ has the same meaning as $L^{G1}$ in general formula (I); each r independently represents an integer from 0 to 4; $W^2$ has the same meaning as $W^2$ in formula (T2-1) or formula (T2-2); and $Y^1$ represents a hydrogen atom).

It is preferable that the compound represented by general formula (I-ii-1) is produced from the synthetic intermediate represented by general formula (I-i-1) above, and it is preferable that the compound represented by general formula (I-ii-1-1) above is produced from the synthetic intermediate represented by general formula (I-i-1-1) above. It is preferable that the compound represented by general formula (I-ii-1-1-1) above is produced from the synthetic intermediate represented by general formula (I-i-1-1-1) above, and it is preferable that the compound represented by general formula (I-ii-1-1-1-1) above is produced from the synthetic intermediate represented by general formula (I-i-1-1-1-1) above. It is preferable that the compound represented by general formula (I-ii-1-1-1-2) above is produced from the synthetic intermediate represented by general formula (I-i-1-1-1-1) above, and it is preferable that the compound represented by general formula (I-ii-1-1-1-2-1) above is produced from the synthetic intermediate represented by general formula (I-i-1-1-1-1-1) above.

The compound represented by general formula (I-ii-1) above is preferably a compound which itself has liquid crystallinity or a compound which itself has no liquid crystallinity but exhibits liquid crystallinity when mixed with another component to form a composition.

In the first production step, it is more preferable to produce the compounds represented by general formula (I-ii-1), general formula (I-ii-1-1), general formula (I-ii-1-1-1), general formula (I-ii-1-1-1-1), general formula (I-ii-1-1-1-2), and general formula (I-ii-1-1-1-2-1) above by reacting the compounds represented by general formula (I-i-1), general formula (I-i-1-1), general formula (I-i-1-1-1), general formula (I-i-1-1-1-1), general formula (I-i-1-1-1-1), and general formula (I-i-1-1-1-1-1), respectively, with a compound represented by the following formula (I-iii-1) or formula (I-iii-2):

[Chem. 52]

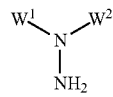

(I-iii-1)

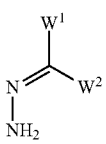

(I-iii-2)

(wherein $W^1$ and $W^2$ have the same meanings as $W^1$ and $W^2$, respectively, in formula (T2-1) and formula (T2-2)). The compound represented by formula (I-iii-1) or formula (I-iii-2) is more preferably a group in which $W^1$ and $W^2$ are each selected from the above-described preferred structures and is still more preferably a compound selected from the following formula (I-iii-1-1) to formula (I-iii-2-5):

[Chem. 53]

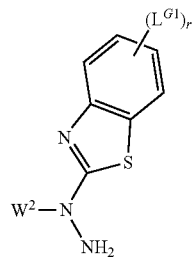

(I-iii-1-1)

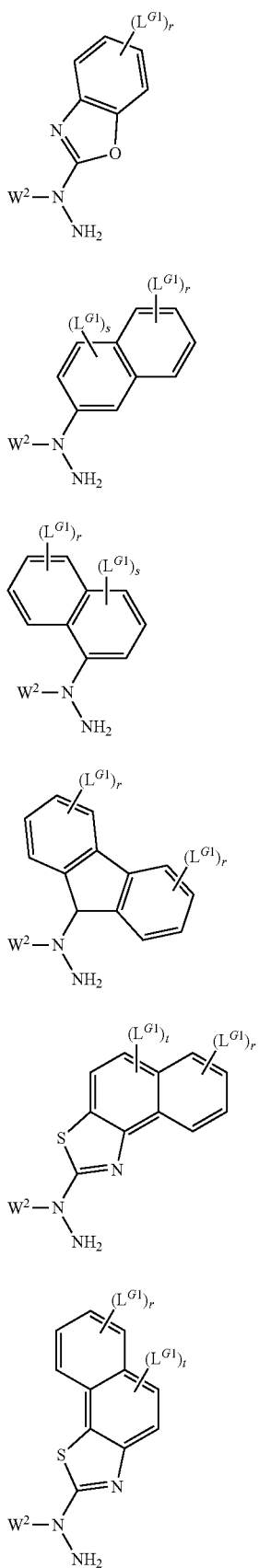
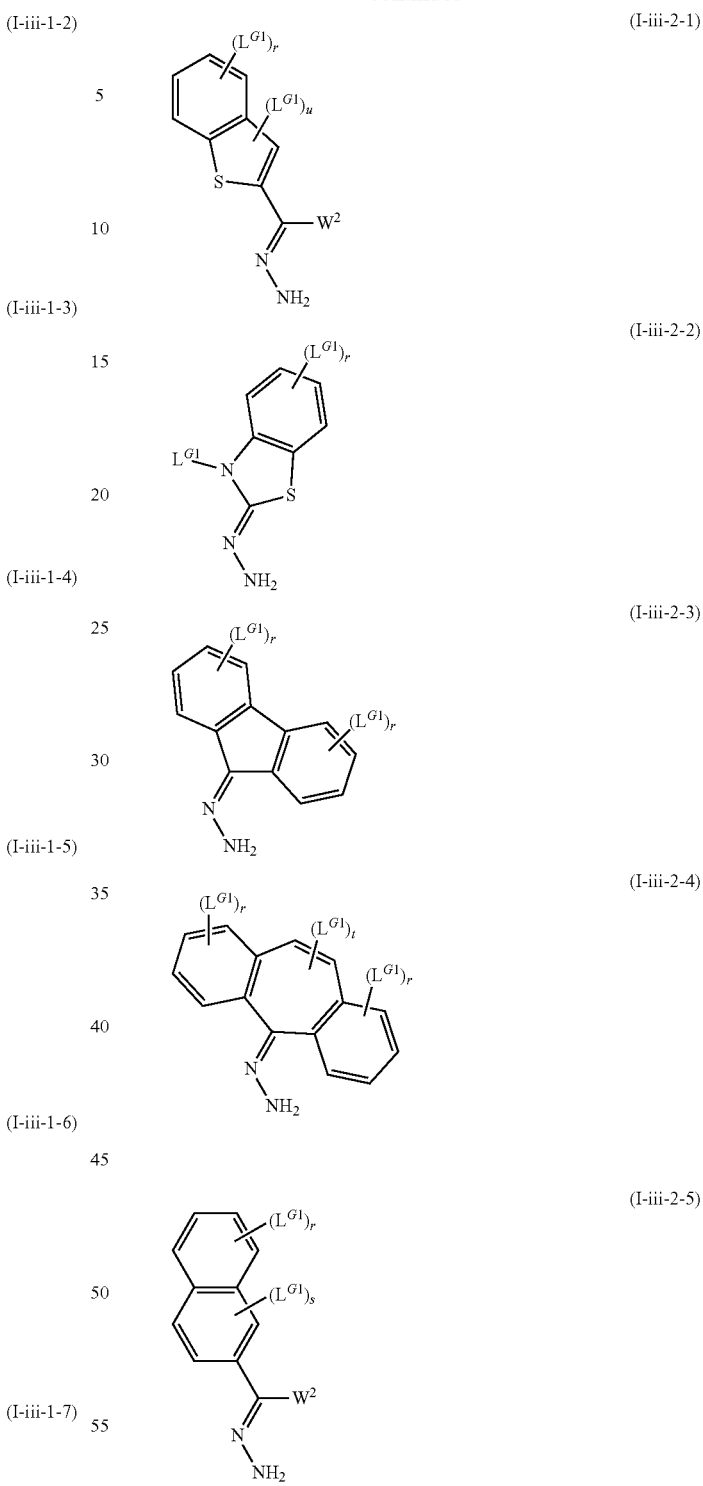

P (wherein $L^{G1}$ and $W^2$ have the same meanings as above; q represents an integer from 0 to 5; r represents an integer from 0 to 4; s represents an integer from 0 to 3; t represents an integer from 0 to 2; and u represents 0 or 1). In formula (I-iii-1-1) to formula (I-iii-2-5) above, r, s, t, and u each represent more preferably 0. More specific examples include compounds represented by the following formula (I-iii-1-1-1) to formula (I-iii-2-3-1):

[Chem. 54]
(I-iii-1-1-1)
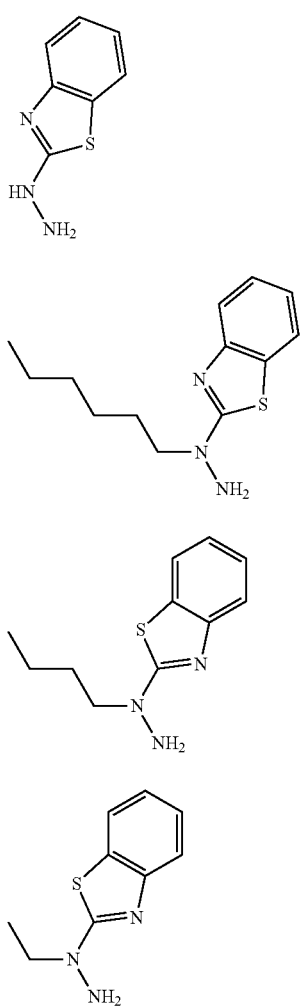
(I-iii-1-1-2)
(I-iii-1-1-3)
(I-iii-1-1-4)
(I-iii-1-1-5)
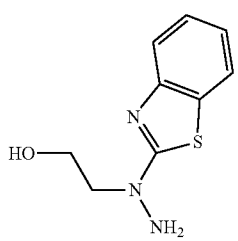
(I-iii-1-1-6)
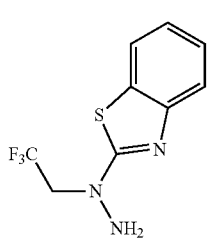
(I-iii-1-1-7)
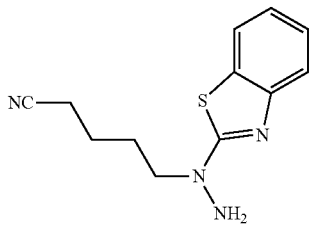
(I-iii-1-1-8)
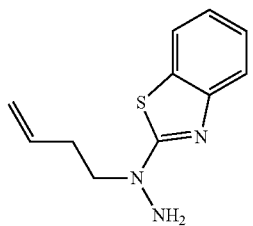
(I-iii-1-1-9)
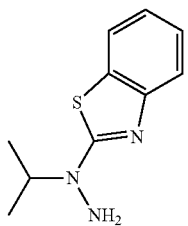
(I-iii-1-1-10)
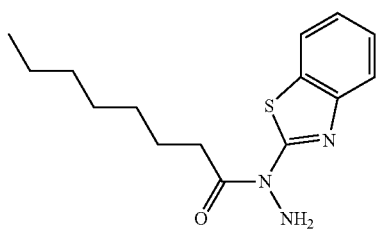
(I-iii-1-1-11)
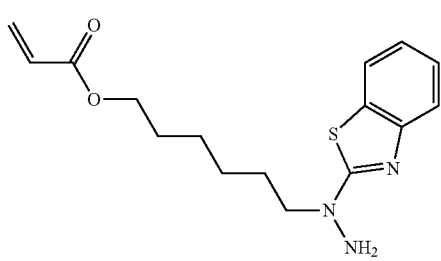
(I-iii-1-1-12)
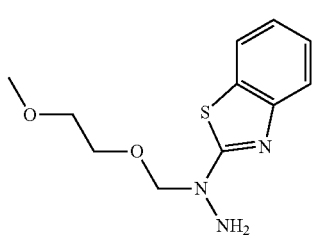

-continued (I-iii-1-1-13)
(I-iii-1-1-14)
(I-iii-1-1-15)
(I-iii-1-1-16)

[Chem. 55]

(I-iii-1-1-17)
(I-iii-1-1-18)

-continued (I-iii-1-1-19)
(I-iii-1-1-20)
(I-iii-1-1-21)
(I-iii-1-1-22)
(I-iii-1-1-23)
(I-iii-1-1-24)

(I-iii-1-1-25) 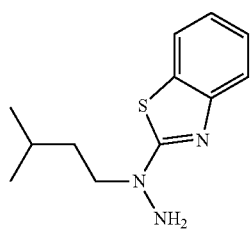

(I-iii-1-1-26) 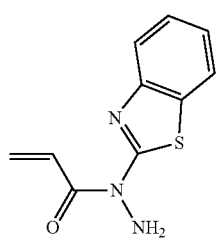

(I-iii-1-1-27) 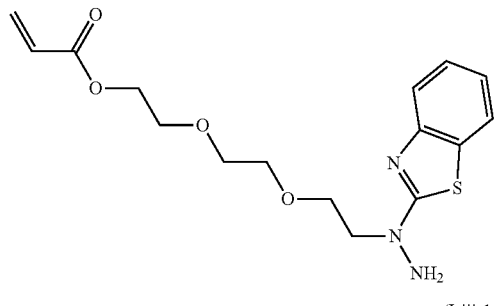

(I-iii-1-1-28) 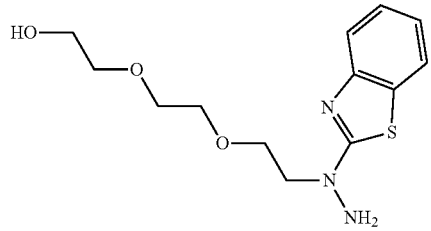

(I-iii-1-5-1) 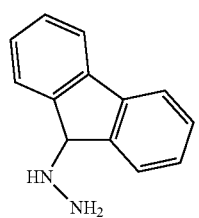

(I-iii-1-6-1) 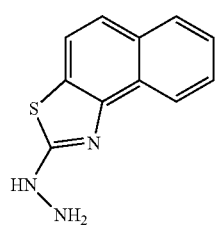

(I-iii-1-7-1) 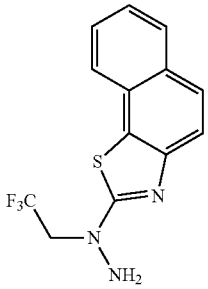

(I-iii-2-3-1) 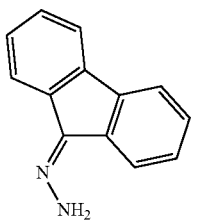

In the above method of producing the derivative of the ester group-containing compound, since the purity of the synthetic intermediate obtained in the first production step is high, the step of removing impurities can be simplified or omitted, so that the efficiency of the production of the derivative of the ester group-containing compound can be improved. When the derivative of the ester group-containing compound obtained by the above production method is used for a material of a polymer, the heat resistance and light-fastness of the polymer obtained can be improved.

Preferably, the ester group-containing compound and its derivative are used for a polymerizable liquid crystal composition. Preferably, the polymerizable liquid crystal composition is a nematic liquid crystal composition, a smectic liquid crystal composition, a chiral smectic liquid crystal composition, or a cholesteric liquid crystal composition.

A known compound may be added to the polymerizable liquid crystal composition. A compound with no liquid crystallinity can be added to the polymerizable liquid crystal composition so long as the liquid crystallinity of the composition is not significantly impaired. The polymerizable liquid crystal composition in the present invention may contain a photopolymerization initiator. The photopolymerization initiator used may be any known photopolymerization initiator, and examples include benzoin ethers, benzophenones, acetophenones, benzil ketals, and acylphosphine oxides. Specific examples of the photopolymerization initiator include 2-methyl-1-(4-methylthiophenyl)-2-morpholinopropan-1-one (IRGACURE 907) and benzoic acid [1-[4-(phenylthio)benzoyl]heptylidene]amino ester (IRGACURE OXE 01). Examples of a thermal polymerization initiator include azo compounds and peroxides. Specific examples of the thermal polymerization initiator include 2,2'-azobis(4-methoxy-2,4-dimethylvaleronitrile) and 2,2'-azobis(isobutyronitrile). One polymerization initiator may be used, or a combination of two or more polymerization initiators may be used.

Since the polymerizable liquid crystal composition contains the ester group-containing compound obtained by the production method of the present invention or the derivative thereof, the polymer obtained by polymerizing the polymerizable liquid crystal composition can have good heat resistance and good lightfastness.

To evaluate the heat resistance, the following method can be used. The polymer is formed into, for example, a film-shaped sample, and the sample is heated under prescribed conditions. Then the degree of deterioration of the sample is observed. For example, heating conditions of 90° C. and 200 hours may be used.

To evaluate the lightfastness, the following method can be used. The polymer is formed into, for example, a film-shaped sample. The sample is subjected to a sun test under prescribed conditions, and then the degree of deterioration of the sample is observed. The sun test conditions used are as follows. For example, a xenon lamp irradiation tester is used under the irradiation conditions of 60 mW/cm², 28° C., and 120 J.

To obtain a film-shaped polymer from the polymerizable liquid crystal composition, the polymerizable liquid crystal composition is applied to a substrate to form a coating supported on the substrate, and then the coating is polymerized. To apply the polymerizable liquid crystal composition to the substrate, spin coating, die coating, extrusion coating, roll coating, wire bar coating, gravure coating, spray coating, dipping, a printing method, etc. may be used. When the coating is formed, an organic solvent may be added to the polymerizable liquid crystal composition. The organic solvent used may be a hydrocarbon-based solvent, a halogenated hydrocarbon-based solvent, an ether-based solvent, an alcohol-based solvent, a ketone-based solvent, an ester-based solvent, an aprotic solvent, etc. Examples of the hydrocarbon-based solvent include toluene and hexane, and examples of the halogenated hydrocarbon-based solvent include methylene chloride. Examples of the ether-based solvent include tetrahydrofuran, acetoxy-2-ethoxyethane, and propylene glycol monomethyl ether acetate, and examples of the alcohol-based solvent include methanol, ethanol, and isopropanol. Examples of the ketone-based solvent include acetone, methyl ethyl ketone, cyclohexanone, γ-butyllactone, and N-methylpyrrolidinone, and examples of the ester-based solvent include ethyl acetate and Cellosolve. Examples of the aprotic solvent include dimethylformamide and acetonitrile. These may be used alone or in combination, and a suitable solvent is selected in consideration of its vapor pressure and the solubility of the polymerizable liquid crystal composition. To volatilize the organic solvent added, air drying, drying by heating, drying under reduced pressure, or drying by heating under reduced pressure may be used. To further improve the spreadability of the polymerizable liquid crystal material, it is effective to provide an intermediate layer such as a polyimide thin film on the substrate or adding a leveling agent to the polymerizable liquid crystal material. Providing an intermediate layer such as a polyimide thin film on the substrate is effective in improving adhesion between the substrate and the polymer obtained by polymerizing the polymerizable liquid crystal material.

Alignment treatment may be used in addition to those described above, and examples of the alignment treatment include utilization of flow-induced alignment of the liquid crystal material and utilization of an electric field or a magnetic field. These alignment means may be used alone or in combination. As an alternative to a rubbing alignment treatment method, an optical alignment method may be used. The substrate may have a flat plate shape and may have a curved surface as its component. As the material forming the substrate, organic materials and also inorganic materials can be used. Examples of the organic material used as the material of the substrate include polyethylene terephthalate, polycarbonate, polyimide, polyamide, polymethyl methacrylate, polystyrene, polyvinyl chloride, polytetrafluoroethylene, polychlorotrifluoroethylene, polyarylate, polysulfone, triacetylcellulose, cellulose, and polyether ether ketone. Examples of the inorganic material include silicon, glass, and calcite.

When the polymerizable liquid crystal composition is polymerized, it is preferable to allow the polymerization to proceed rapidly. Therefore, it is preferable to use a polymerization method including irradiation with active energy rays such as ultraviolet rays or electron beams. When ultraviolet rays are used, a polarized light source may be used, or a non-polarized light source may be used. When the liquid crystal composition sandwiched between two substrates is polymerized, at least the irradiation-side substrate must have appropriate transparency to the active energy rays. Alternatively, the following means may be used. A mask is used during irradiation with light to polymerize only specific portions. Then the alignment state of non-polymerized portions is changed by changing electric field conditions, magnetic field conditions, temperature conditions, etc., and the non-polymerized portions are polymerized by irradiating them with active energy rays. Preferably, the temperature during the irradiation is in the temperature range in which the liquid crystal state of the polymerizable liquid crystal composition of the present invention is maintained. In particular, when an optically anisotropic body is produced by photopolymerization, it is preferable to perform polymerization at a temperature as close as possible to room temperature, i.e., typically 25° C., in order to avoid induction of unintended thermal polymerization. Preferably, the intensity of the active energy rays is 0.1 mW/cm² to 2 W/cm². If the intensity is 0.1 mW/cm² or less, a very long time is required to complete the photopolymerization, and this causes deterioration in productivity. If the intensity is 2 W/cm² or more, there is a risk of deterioration of a polymerizable liquid crystal compound or the polymerizable liquid crystal composition.

The present invention encompasses an N-acylurea composition containing the ester group-containing compound obtained by the production method of the present invention and represented by the following general formula (a-5):

(a-5)

(wherein $R^{a5}$ and $R^{a6}$ each represent an organic group having 1 to 1,000 carbon atoms) and an N-acylurea represented by the following general formula (a-6):

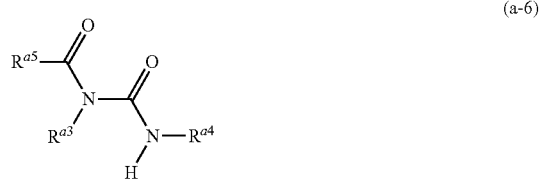

(a-6)

(wherein $R^{a5}$ has the same meaning as above, and $R^{a3}$ and $R^{a4}$ each represent an organic group having 1 to 100 carbon atoms), wherein the ratio of the molar amount of the N-acylurea to the molar amount of the ester group-containing compound is from 0.003 to 0.05 inclusive. From the viewpoint of productivity, the ratio of the molar amount of the N-acylurea is preferably from 0.004 to 0.005 inclusive. From the viewpoint that the composition can be used as a suitable raw material of an optically anisotropic body, the ratio of the molar amount of the N-acylurea is preferably 0.03 or less, more preferably 0.02 or less, and still more preferably 0.01 or less.

The N-acylurea composition may contain a compound having a carbodiimide structure. The ratio of the molar amount of the compound having a carbodiimide structure to the molar amount of the ester group-containing compound is preferably from 0.001 to 0.5 or less inclusive.

Eluting solvent: 0.1% formic acid-acetonitrile/water (90:10) or acetonitrile/water (90:10)

Flow rate: 0.5 mL/min

Detector: UV

Column oven: 40° C.

(Example 1) Production of Compound Represented by Formula (I-1)

[Chem. 56]

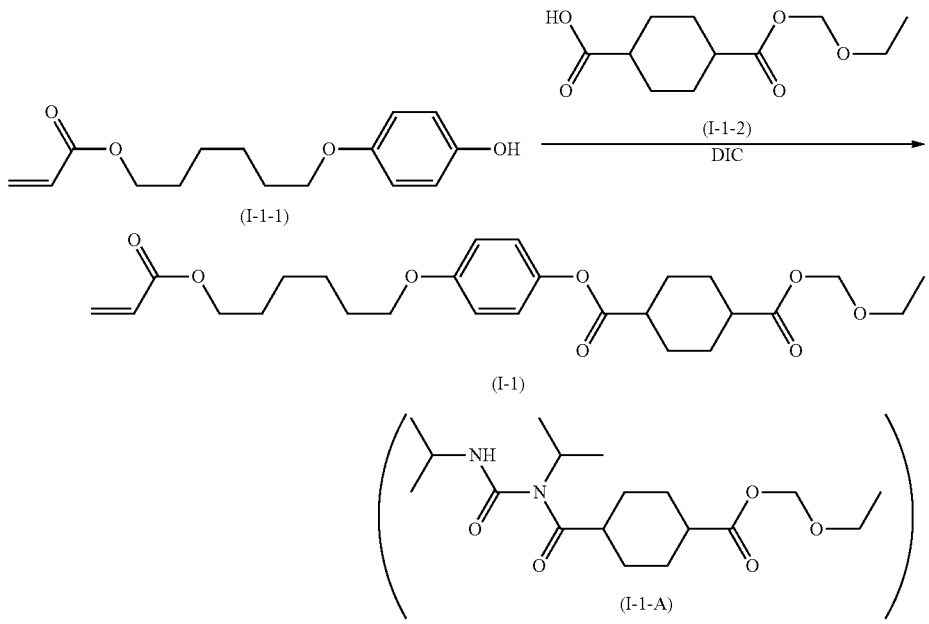

EXAMPLES

The present invention will be further described by way of Examples. However, the present invention is not limited to these Examples. In each of the following Examples and Comparative Examples, "%" means "% by mass," and the yield was computed based on the theoretical yield of the product, i.e., the ester group-containing compound. When a material unstable toward oxygen and/or water was used in a process, its operation was performed in an inert gas such as nitrogen gas or argon gas.

(Gas Chromatography Analysis Conditions)

Column: Agilent Technologies, J & W Column DB-1HT, 15 m×0.25 mm×0.10 μm

Temperature program: 100° C. (held for 1 minute)—(temperature rise rate: 20° C./minute)—250° C.—(temperature rise rate: 10° C./minute)—380° C.—(temperature rise rate: 7° C./minute)—400° C. (held for 2.64 minutes)

Inlet temperature: 350° C.

Detector temperature: 400° C.

(Liquid Chromatography Analysis Conditions)

Column: Waters ACQUITY UPLC BEH $C_{18}$, 2.1×100 mm, 1.7 μm

A reaction vessel was charged with 5.0 g of a compound represented by formula (I-1-1), 4.4 g of a compound represented by formula (I-1-2), 0.69 g of 4-dimethylaminopyridine, 50 mL of dichloromethane, and 0.73 g of methanesulfonic acid in a nitrogen atmosphere. While the reaction vessel was cooled with ice, 2.9 g of diisopropylcarbodiimide was added dropwise, and the mixture was stirred at room temperature for 5 hours. After the resulting precipitate was removed by filtration, the solvent was removed by evaporation, and the product was dispersed in methanol and washed. The product was purified by column chromatography (alumina, dichloromethane) and reprecipitation (dichloromethane/methanol) to thereby obtain 8.5 g of a compound represented by formula (I-1). The yield of the compound represented by formula (I-1) was 95%. After the reaction, an N-acylurea represented by formula (I-1-A) was found to be formed, and its amount was 1.1%. After the purification, the N-acylurea represented by formula (I-1-A) was not detected in the compound represented by formula (I-1).

LC-MS: 477 [M+1]

(Comparative Example 1) Production of Compound Represented by Formula (I-1R)

[Chem. 57]

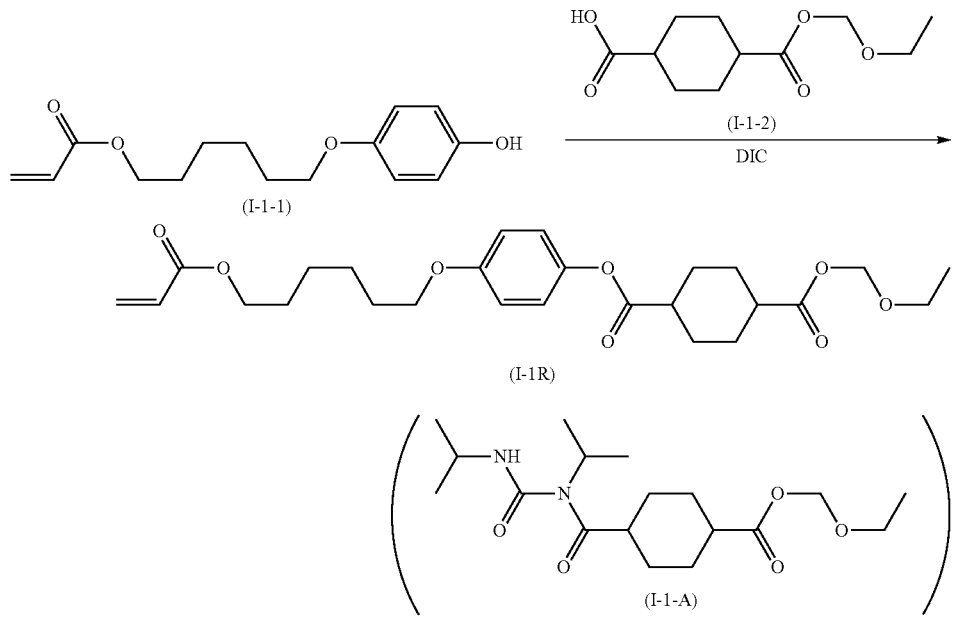

A reaction vessel was charged with 5.0 g of the compound represented by formula (I-1-1), 4.4 g of the compound represented by formula (I-1-2), 0.69 g of 4-dimethylaminopyridine, and 50 mL of dichloromethane in a nitrogen atmosphere. While the reaction vessel was cooled with ice, 2.9 g of diisopropylcarbodiimide was added dropwise, and the mixture was stirred at room temperature for 5 hours. After the resulting precipitate was removed by filtration, the solvent was removed by evaporation, and the product was dispersed in methanol and washed. The product was purified by column chromatography (alumina, dichloromethane) and reprecipitation (dichloromethane/methanol) to thereby obtain 7.8 g of a compound represented by formula (I-1R). The yield of the compound represented by formula (I-1R) was 86%. After the reaction, the N-acylurea represented by formula (I-1-A) was found to be formed, and its amount was 5.2%. After the purification, the N-acylurea represented by formula (I-1-A) was not detected in the compound represented by formula (I-1R).

LC-MS: 477 [M+1]

(Example 2) Production of Compound Represented by Formula (I-2)

[Chem. 58]

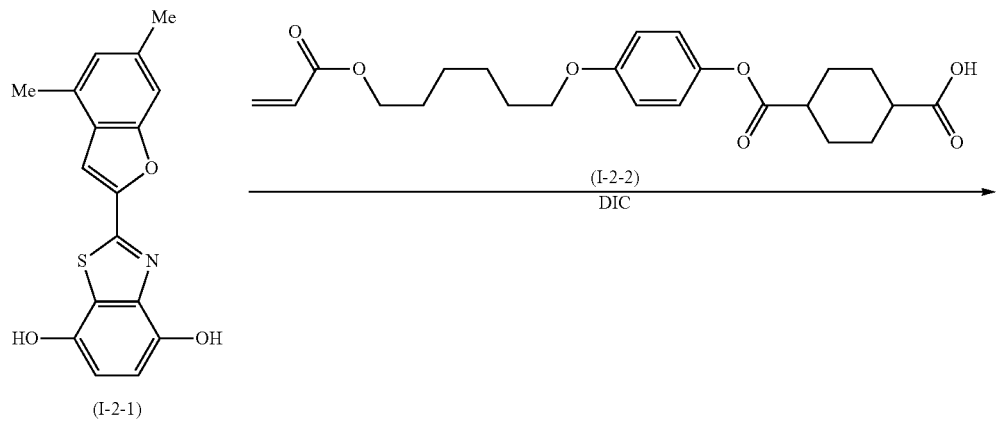

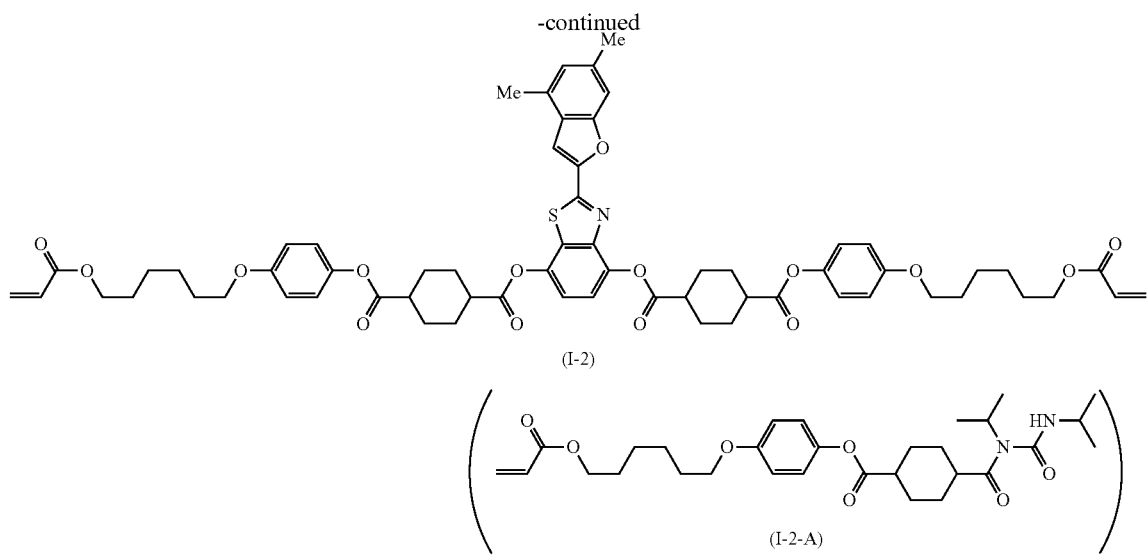

(I-2)

(I-2-A)

A compound represented by formula (I-2-1) was produced by a method described in Japanese Unexamined Patent Application Publication No. 2011-207765.

A reaction vessel was charged with 3.0 g of the compound represented by formula (I-2-1), 8.1 g of a compound represented by formula (I-2-2), 0.35 g of 4-dimethylaminopyridine, 80 mL of dichloromethane, and 0.37 g of methanesulfonic acid in a nitrogen atmosphere. While the reaction vessel was cooled with ice, 3.0 g of diisopropylcarbodiimide was added dropwise, and the mixture was stirred at room temperature for 5 hours. After the resulting precipitate was removed by filtration, the solvent was removed by evaporation, and the product was dispersed in methanol and washed. The product was purified by column chromatography (alumina, dichloromethane) and reprecipitation (dichloromethane/methanol) to thereby obtain 9.6 g of a compound represented by formula (I-2). The yield of the compound represented by formula (I-2) was 90%. After the reaction, an N-acylurea represented by formula (I-2-A) was found to be formed, and its amount was 1.0%. After the purification, the N-acylurea represented by formula (I-2-A) was not detected in the compound represented by formula (I-2).

LC-MS: 1112 [M+1]

(Comparative Example 2) Production of Compound Represented by Formula (I-2R)

[Chem. 59]

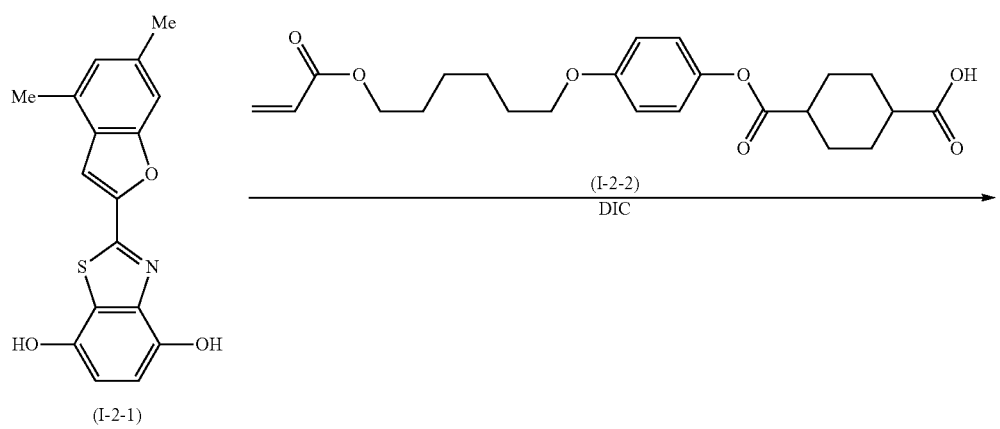

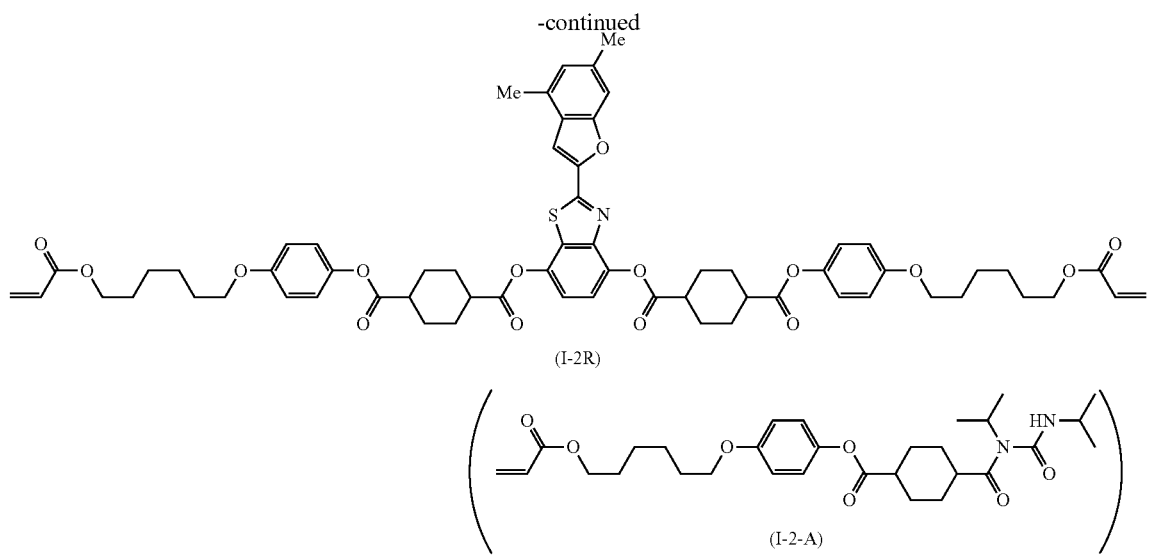

A reaction vessel was charged with 3.0 g of the compound represented by formula (I-2-1), 8.1 g of the compound represented by formula (I-2-2), 0.35 g of 4-dimethylaminopyridine, and 80 mL of dichloromethane in a nitrogen atmosphere. While the reaction vessel was cooled with ice, 3.0 g of diisopropylcarbodiimide was added dropwise, and the mixture was stirred at room temperature for 5 hours. After the resulting precipitate was removed by filtration, the solvent was removed by evaporation, and the product was dispersed in methanol and washed. The product was purified by column chromatography (alumina, dichloromethane) and reprecipitation (dichloromethane/methanol) to thereby obtain 8.7 g of a compound represented by formula (I-2R). The yield of the compound represented by formula (I-2R) was 81%. After the reaction, the N-acylurea represented by formula (I-2-A) was found to be formed, and its amount was 6.1%. After the purification, the compound represented by formula (I-2R) was found to contain 0.1% of the N-acylurea represented by formula (I-2-A).

LC-MS: 1112 [M+1]

(Example 3) Production of Compound Represented by Formula (I-3)

[Chem. 60]

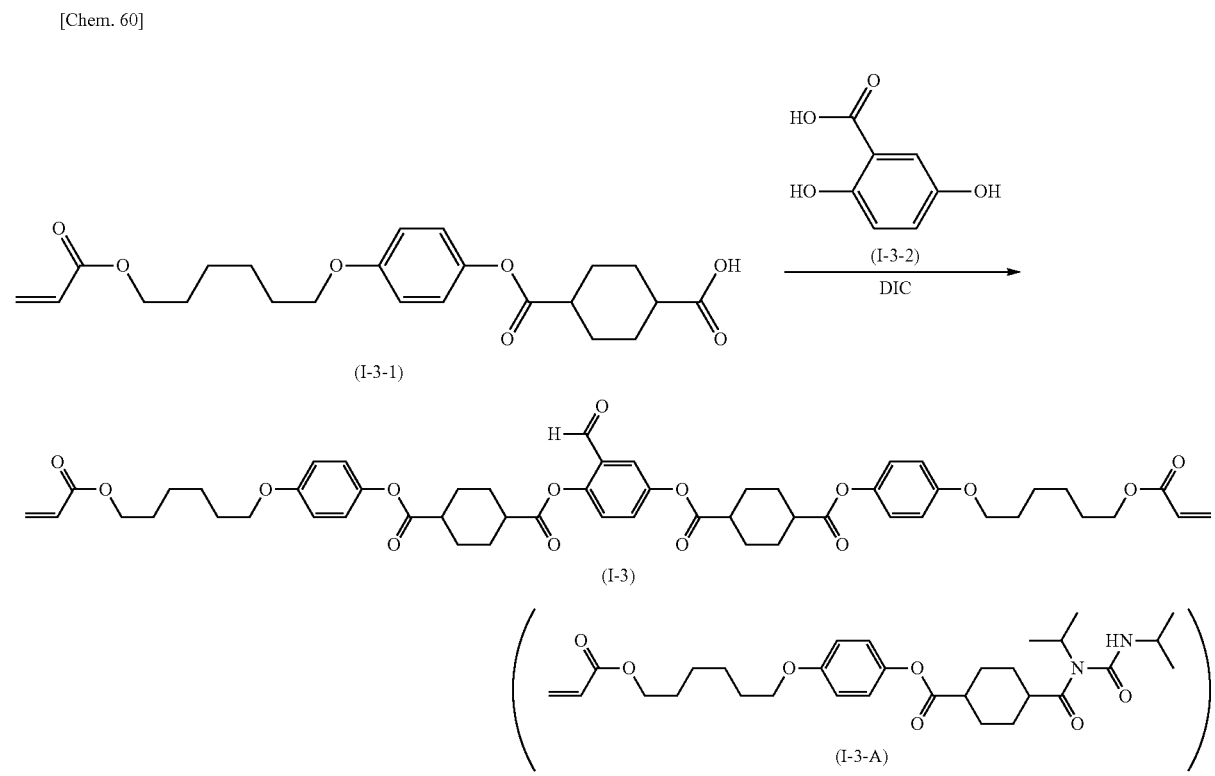

A reaction vessel was charged with 8.0 g of a compound represented by formula (I-3-1), 1.3 g of a compound represented by formula (I-3-2), 0.58 g of 4-dimethylaminopyridine, 80 mL of dichloromethane, and 0.47 g of concentrated sulfuric acid in a nitrogen atmosphere. While the reaction vessel was cooled with ice, 2.7 g of diisopropylcarbodiimide was added dropwise, and the mixture was stirred at room temperature for 5 hours. After the resulting precipitate was removed by filtration, the solvent was removed by evaporation, and the product was dispersed in methanol and washed. The product was purified by column chromatography (alumina, dichloromethane) and reprecipitation (dichloromethane/methanol) to thereby obtain 8.2 g of a compound represented by formula (I-3). The yield of the compound represented by formula (I-3) was 91%. After the reaction, an N-acylurea represented by formula (I-3-A) was found to be formed, and its amount was 1.6%. After the purification, the N-acylurea represented by formula (I-3-A) was not detected in the compound represented by formula (I-3).

LC-MS: 939 [M+1]

(Comparative Example 3) Production of Compound Represented by Formula (I-3R)

[Chem. 61]

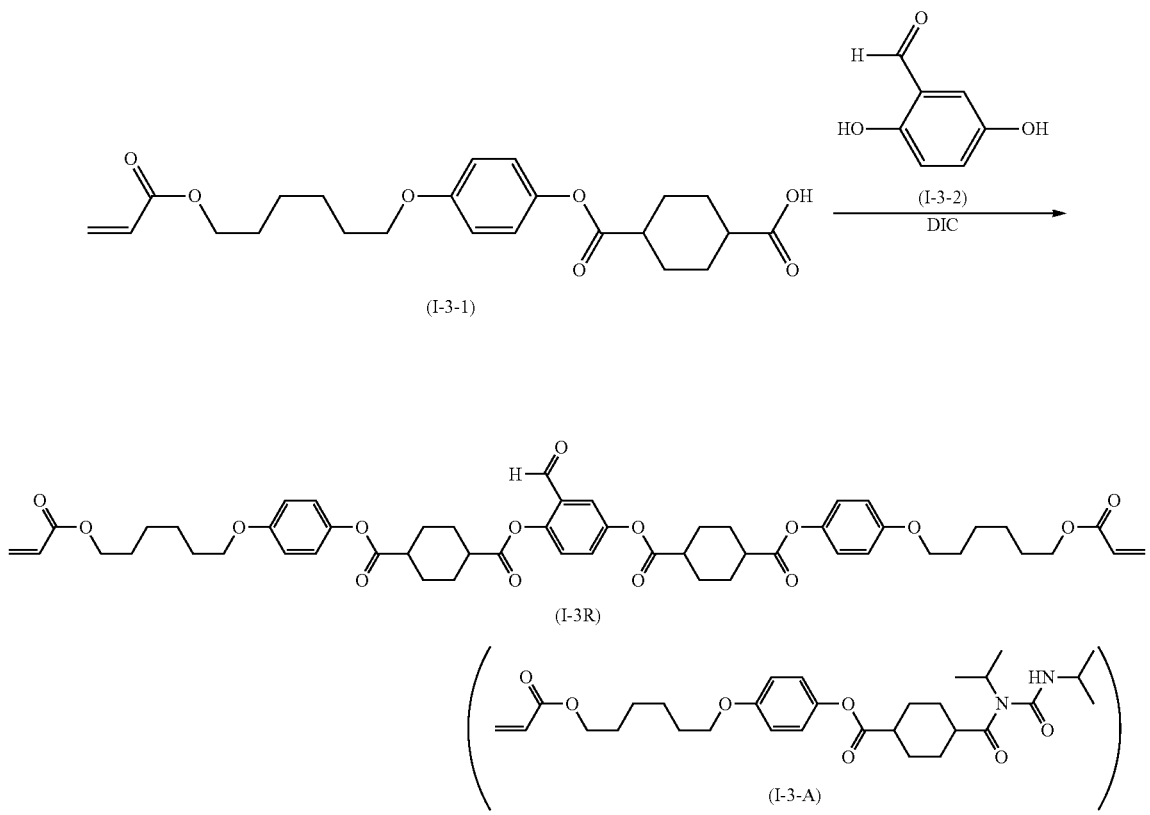

A reaction vessel was charged with 8.0 g of the compound represented by formula (I-3-1), 1.3 g of the compound represented by formula (I-3-2), 0.58 g of 4-dimethylaminopyridine, and 80 mL of dichloromethane in a nitrogen atmosphere. While the reaction vessel was cooled with ice, 2.7 g of diisopropylcarbodiimide was added dropwise, and the mixture was stirred at room temperature for 5 hours. After the resulting precipitate was removed by filtration, the solvent was removed by evaporation, and the product was dispersed in methanol and washed. The product was purified by column chromatography (alumina, dichloromethane) and reprecipitation (dichloromethane/methanol) to thereby obtain 7.4 g of a compound represented by formula (I-3R). The yield of the compound represented by formula (I-3R) was 82%. After the reaction, the N-acylurea represented by formula (I-3-A) was found to be formed, and its amount was 6.9%. After the purification, the N-acylurea represented by formula (I-3-A) was not detected in the compound represented by formula (I-3R).

LC-MS: 939 [M+1]

(Example 4) Production of Compound Represented by Formula (I-4)

[Chem. 62]

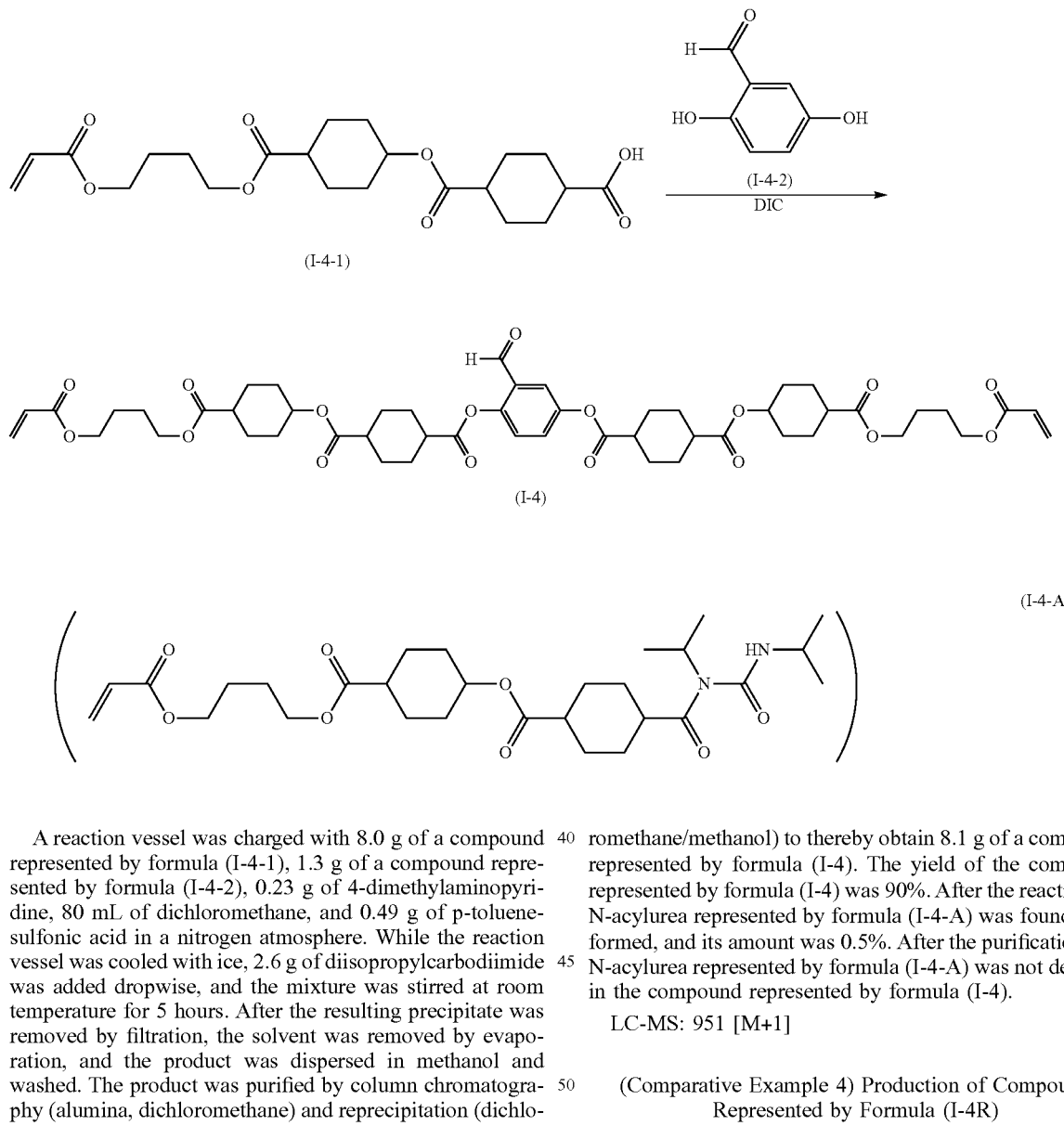

A reaction vessel was charged with 8.0 g of a compound represented by formula (I-4-1), 1.3 g of a compound represented by formula (I-4-2), 0.23 g of 4-dimethylaminopyridine, 80 mL of dichloromethane, and 0.49 g of p-toluenesulfonic acid in a nitrogen atmosphere. While the reaction vessel was cooled with ice, 2.6 g of diisopropylcarbodiimide was added dropwise, and the mixture was stirred at room temperature for 5 hours. After the resulting precipitate was removed by filtration, the solvent was removed by evaporation, and the product was dispersed in methanol and washed. The product was purified by column chromatography (alumina, dichloromethane) and reprecipitation (dichloromethane/methanol) to thereby obtain 8.1 g of a compound represented by formula (I-4). The yield of the compound represented by formula (I-4) was 90%. After the reaction, an N-acylurea represented by formula (I-4-A) was found to be formed, and its amount was 0.5%. After the purification, the N-acylurea represented by formula (I-4-A) was not detected in the compound represented by formula (I-4).

LC-MS: 951 [M+1]

(Comparative Example 4) Production of Compound Represented by Formula (I-4R)

[Chem. 63]

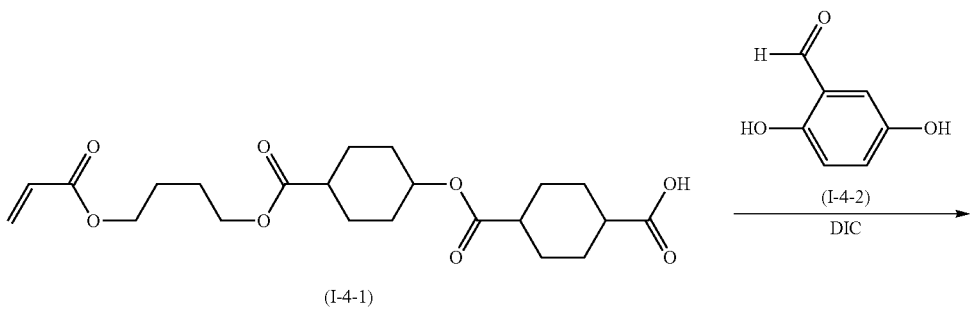

-continued

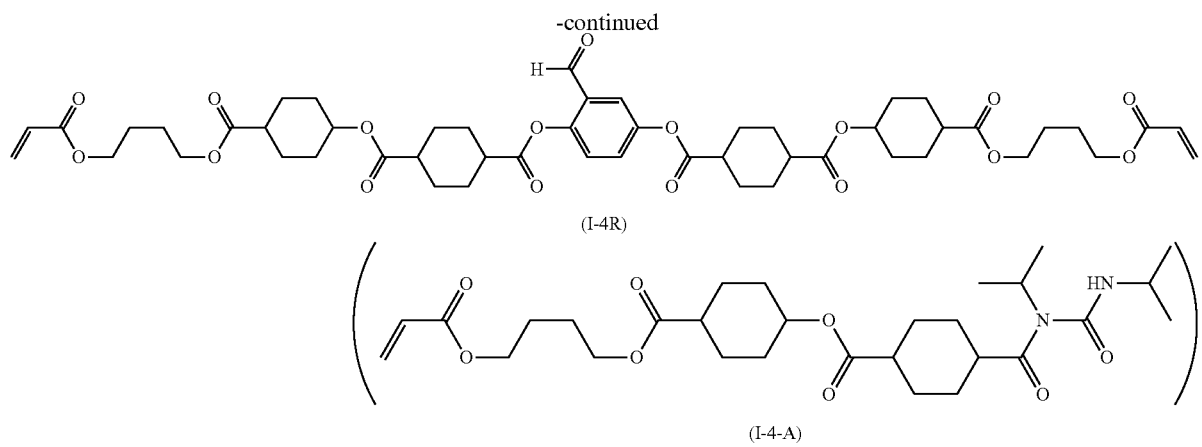

(I-4R)

(I-4-A)

A reaction vessel was charged with 8.0 g of the compound represented by formula (I-4-1), 1.3 g of the compound represented by formula (I-4-2), 0.23 g of 4-dimethylaminopyridine, and 80 mL of dichloromethane in a nitrogen atmosphere. While the reaction vessel was cooled with ice, 2.6 g of diisopropylcarbodiimide was added dropwise, and the mixture was stirred at room temperature for 5 hours. After the resulting precipitate was removed by filtration, the solvent was removed by evaporation, and the product was dispersed in methanol and washed. The product was purified by column chromatography (alumina, dichloromethane) and reprecipitation (dichloromethane/methanol) to thereby obtain 7.1 g of a compound represented by formula (I-4R). The yield of the compound represented by formula (I-4R) was 79%. After the reaction, the N-acylurea represented by formula (I-4-A) was found to be formed, and its amount was 8.4%. After the purification, the compound represented by formula (I-4R) was found to contain 0.1% of the N-acylurea represented by formula (I-4-A).

LC-MS: 951 [M+1]

(Example 5) Production of Compound Represented by Formula (I-5)

[Chem. 64]

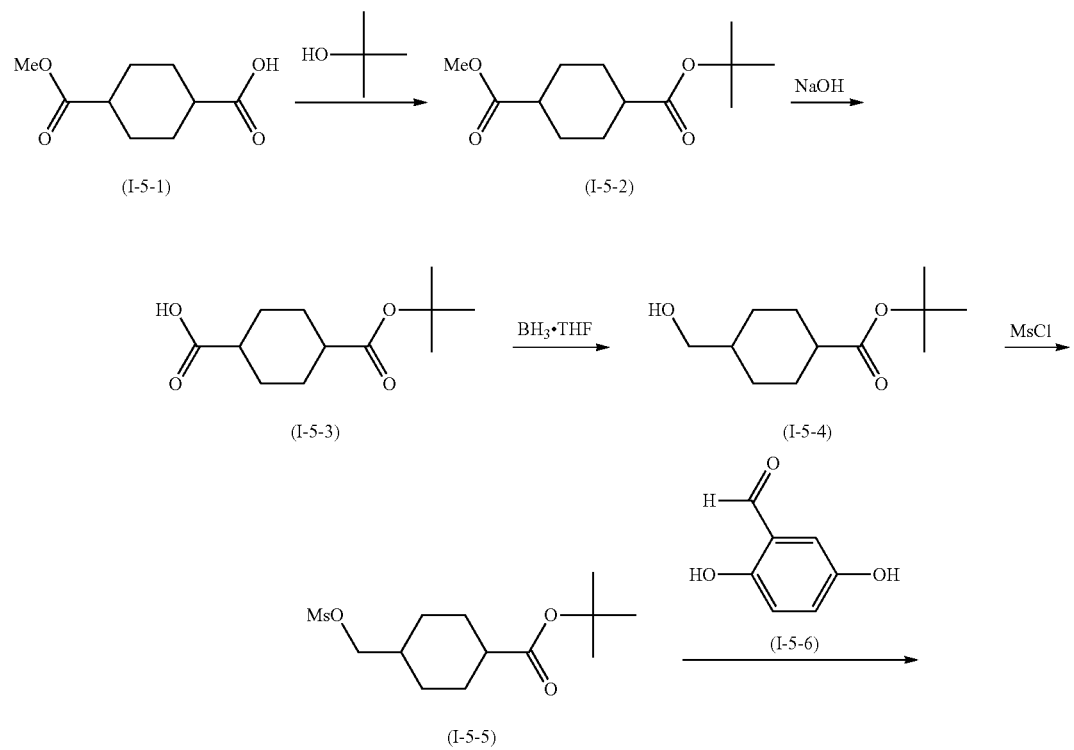

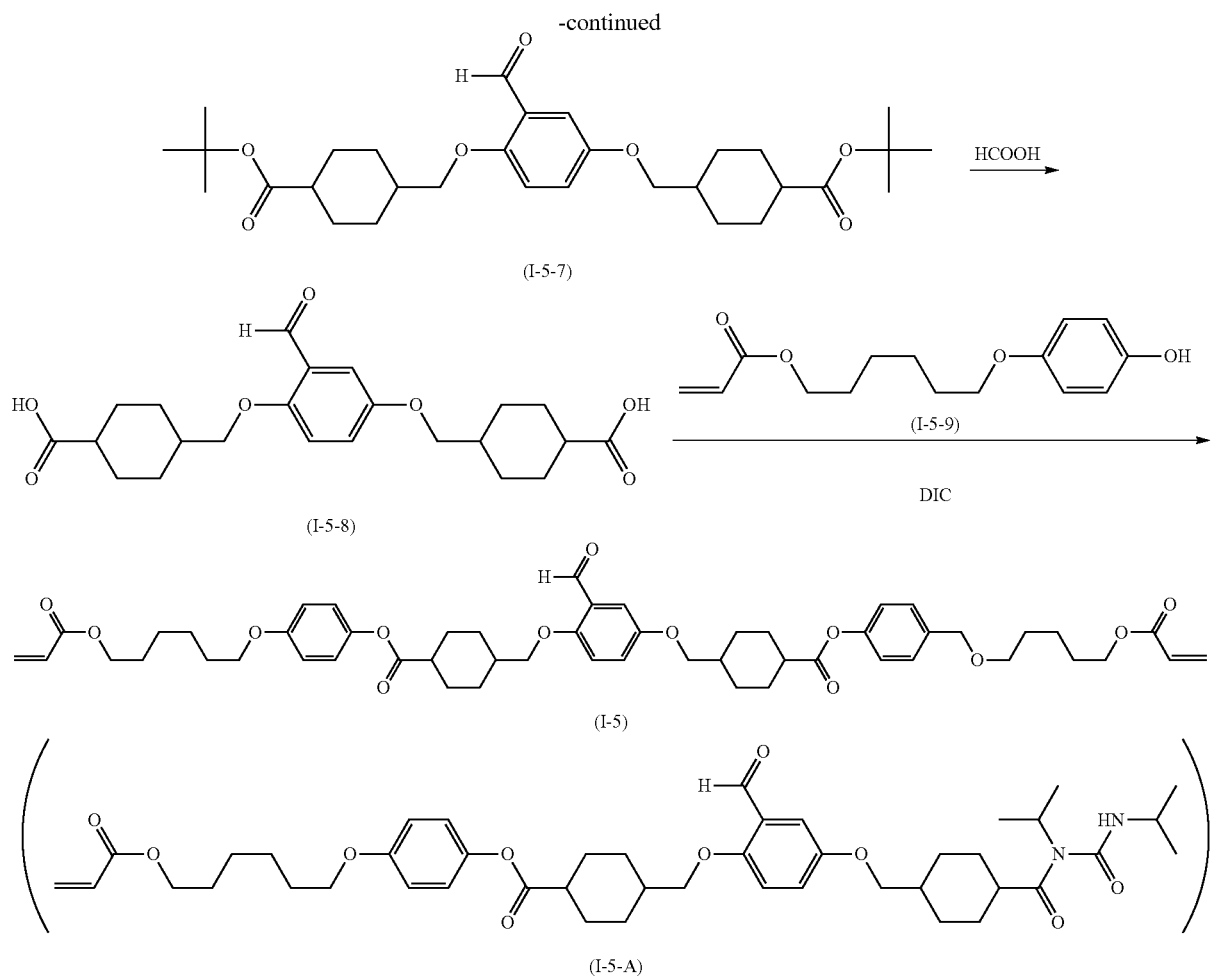

A reaction vessel was charged with 20.0 g of a compound represented by formula (I-5-1), 8.8 g of tert-butyl alcohol, 1.3 g of 4-dimethylaminopyridine, and 100 mL of dichloromethane in a nitrogen atmosphere. While the reaction vessel was cooled with ice, 16.3 g of diisopropylcarbodiimide was added dropwise, and the mixture was stirred at room temperature for 8 hours. The resulting precipitate was removed by filtration, and the filtrate was washed with 5% hydrochloric acid and then brine. The product was purified by column chromatography (silica gel, dichloromethane) to thereby obtain 20.8 g of a compound represented by formula (I-5-2).

A reaction vessel was charged with 20.8 g of the compound represented by formula (I-5-2), 200 mL of methanol, and 30 mL of a 25% aqueous sodium hydroxide solution, and the mixture was heated to 60° C. and stirred. The resulting mixture was cooled, and chloroform was added. 10% Hydrochloric acid was added to adjust the pH of the aqueous layer to 4 to 5, and the mixture was subjected to liquid separation treatment. The organic layer was washed with brine and dried over sodium sulfate. The insoluble matter was filtered off using celite. Then the solvent was removed by evaporation, and the product was dried to thereby obtain 17.7 g of a compound represented by formula (I-5-3).

A reaction vessel was charged with 17.7 g of the compound represented by formula (I-5-3) and 100 mL of tetrahydrofuran in a nitrogen atmosphere. While the reaction vessel was cooled with ice, 103 mL of a 0.9 mol/L borane-tetrahydrofuran complex was added dropwise, and the mixture was stirred for 1 hour. After 5% hydrochloric acid was added dropwise, the mixture was extracted with ethyl acetate and washed with brine. The resulting mixture was dried over sodium sulfate, and the solvent was removed by evaporation to thereby obtain 14.9 g of a compound represented by formula (I-5-4).

A reaction vessel was charged with 14.9 g of the compound represented by formula (I-5-4), 7.2 g of pyridine, and 150 mL of dichloromethane in a nitrogen atmosphere. While the reaction vessel was cooled with ice, 8.8 g of methanesulfonyl chloride was added dropwise, and the mixture was stirred at room temperature for 3 hours. The resulting mixture was poured into water and washed with 5% hydrochloric acid and then brine. The product was purified by column chromatography (silica gel, hexane/ethyl acetate) and recrystallization (acetone/hexane) to thereby obtain 16.3 g of a compound represented by formula (I-5-5).

A reaction vessel was charged with 25.0 g of 2,5-dimethoxybenzaldehyde and 200 mL of dichloromethane in a nitrogen atmosphere. While the reaction vessel was cooled with ice, 113.1 g of boron tribromide was added dropwise, and the mixture was stirred for 2 hours. After the mixture was poured into iced water, the resulting mixture was extracted with ethyl acetate and washed with water and then brine. The product was purified by column chromatography (alumina, ethyl acetate) to thereby obtain 18.7 g of a compound represented by formula (I-5-6).

A reaction vessel was charged with 2.5 g of the compound represented by formula (I-5-6), 10.6 g of the compound represented by formula (I-5-5), 11.5 g of potassium phosphate, and 70 mL of N,N-dimethylformamide in a nitrogen atmosphere, and the mixture was heated to 90° C. and stirred for 12 hours. The resulting mixture was poured into water, extracted with dichloromethane, and washed with brine. The product was purified by column chromatography (silica gel, dichloromethane) and recrystallization (dichloromethane/methanol) to thereby obtain 7.7 g of a compound represented by formula (I-5-7).

A reaction vessel was charged with 7.7 g of the compound represented by formula (I-5-7), 150 mL of dichloromethane, and 100 mL of formic acid in a nitrogen atmosphere, and the mixture was heated and refluxed for 8 hours. After the solvent was removed by evaporation, diisopropyl ether was added, and the resulting mixture was dispersed, washed, and dried to thereby obtain 5.5 g of a compound represented by formula (I-5-8).

A reaction vessel was charged with 3.0 g of the compound represented by formula (I-5-8), 3.8 g of a compound represented by formula (I-5-9), 0.26 g of 4-dimethylaminopyridine, 50 mL of dichloromethane, and 0.28 g of methanesulfonic acid in a nitrogen atmosphere. While the reaction vessel was cooled with ice, 2.1 g of diisopropylcarbodiimide was added dropwise, and the mixture was stirred at 40° C. for 5 hours. After the resulting precipitate was removed by filtration, the solvent was removed by evaporation, and the product was dispersed in methanol and washed. The product was purified by column chromatography (silica gel, dichloromethane) and reprecipitation (dichloromethane/methanol) to thereby obtain 5.9 g of a compound represented by formula (I-5). The yield of the compound represented by formula (I-5) was 90%. After the reaction, an N-acylurea represented by formula (I-5-A) was found to be formed, and its amount was 1.5%. After the purification, the N-acylurea represented by formula (I-5-A) was not detected in the compound represented by formula (I-5).

LC-MS: 911 [M+1]

(Comparative Example 5) Production of Compound Represented by Formula (I-5R)

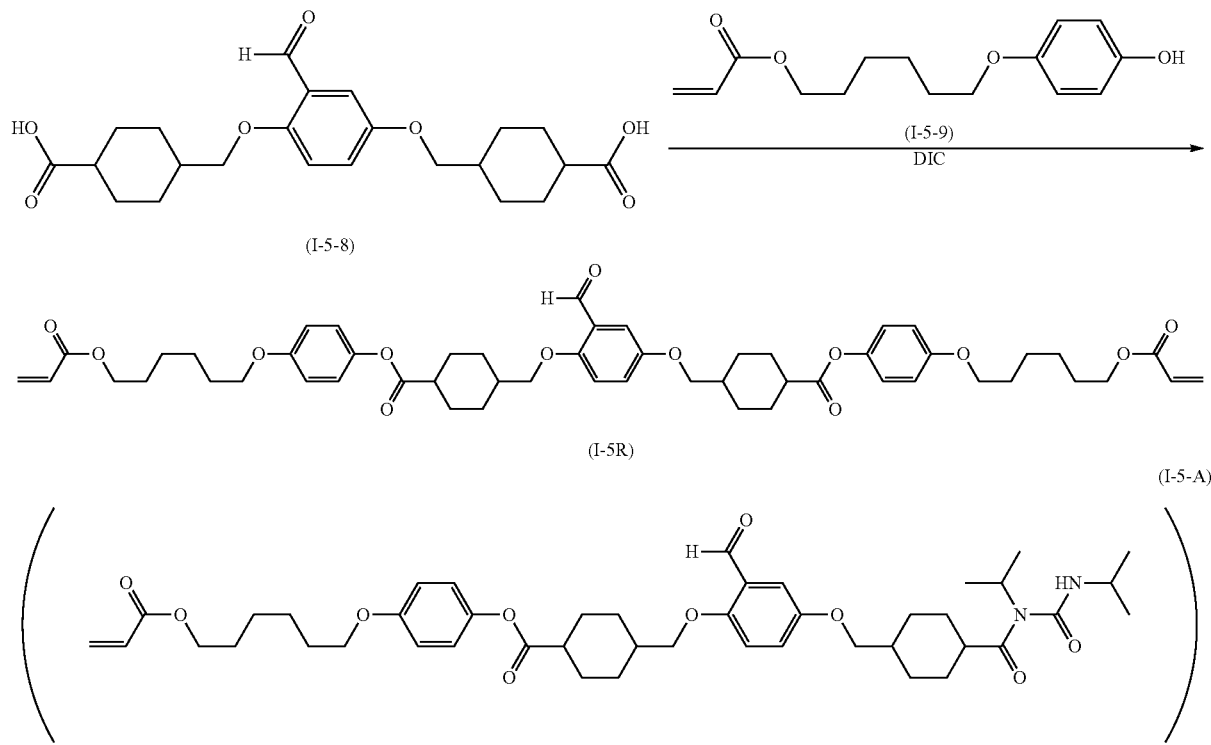

[Chem. 65]

A reaction vessel was charged with 3.0 g of the compound represented by formula (I-5-8), 3.8 g of the compound represented by formula (I-5-9), 0.26 g of 4-dimethylaminopyridine, and 50 mL of dichloromethane in a nitrogen atmosphere. While the reaction vessel was cooled with ice, 2.1 g of diisopropylcarbodiimide was added dropwise, and the mixture was stirred at 40° C. for 5 hours. After the resulting precipitate was removed by filtration, the solvent was removed by evaporation, and the product was dispersed in methanol and washed. The product was purified by column chromatography (silica gel, dichloromethane) and reprecipitation (dichloromethane/methanol) to thereby obtain 3.6 g of a compound represented by formula (I-5R). The yield of the compound represented by formula (I-5R) was %. After the reaction, the N-acylurea represented by formula (I-5-A) was found to be formed, and its amount was 31.1%. After the purification, the N-acylurea represented by formula (I-5-A) was not detected in the compound represented by formula (I-5R).

LC-MS: 911 [M+1]

(Example 6) Production of Compound Represented by Formula (I-6)

[Chem. 66]

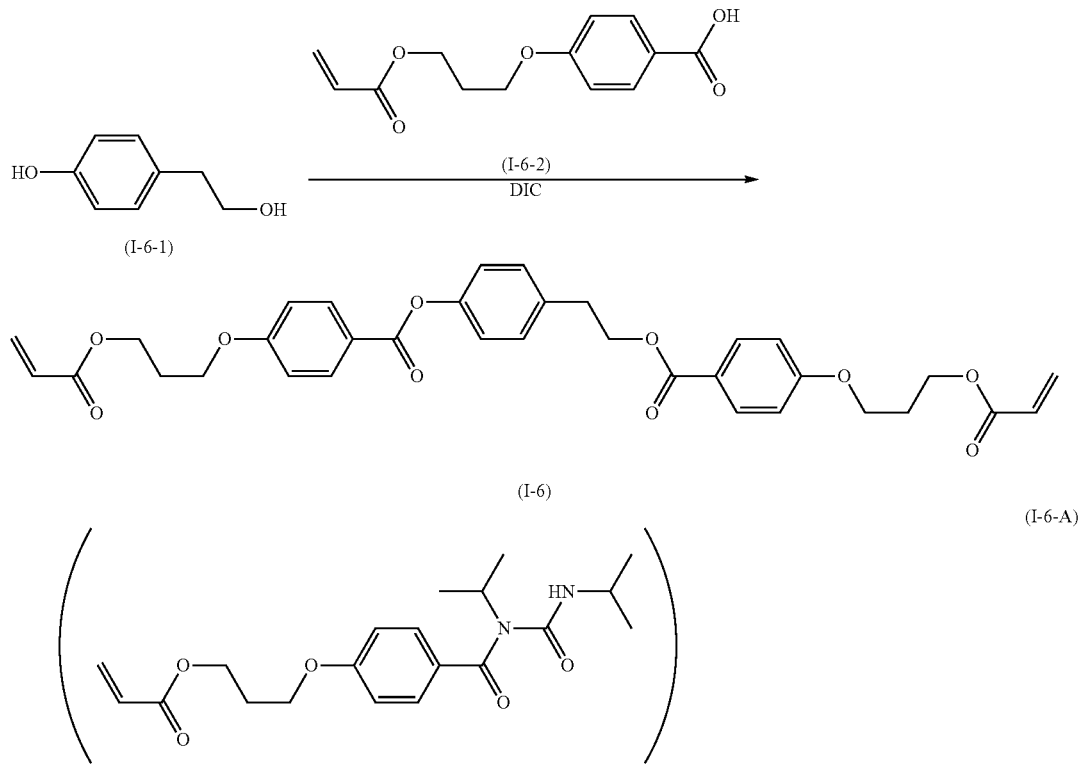

A reaction vessel was charged with 2.0 g of a compound represented by formula (I-6-1), 7.2 g of a compound represented by formula (I-6-2), 0.35 g of 4-dimethylaminopyridine, 40 mL of dichloromethane, and 0.90 g of benzenesulfinic acid in a nitrogen atmosphere. While the reaction vessel was cooled with ice, 4.0 g of diisopropylcarbodiimide was added dropwise, and the mixture was stirred at room temperature for 7 hours. After the resulting precipitate was removed by filtration, the solvent was removed by evaporation, and the product was dispersed in methanol and washed. The product was purified by column chromatography (silica gel, dichloromethane) and reprecipitation (dichloromethane/methanol) to thereby obtain 7.9 g of a compound represented by formula (I-6). The yield of the compound represented by formula (I-6) was 91%. After the reaction, an N-acylurea represented by formula (I-6-A) was found to be formed, and its amount was 1.6%. After the purification, the N-acylurea represented by formula (I-6-A) was not detected in the compound represented by formula (I-6).

LC-MS: 603 [M+1]

(Comparative Example 6) Production of Compound Represented by Formula (I-6R)

[Chem. 67]

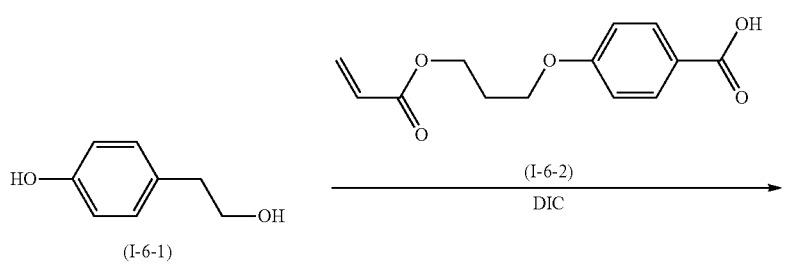

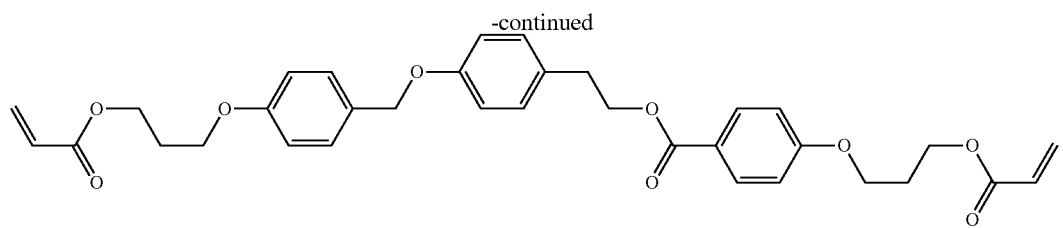

(I-6R)

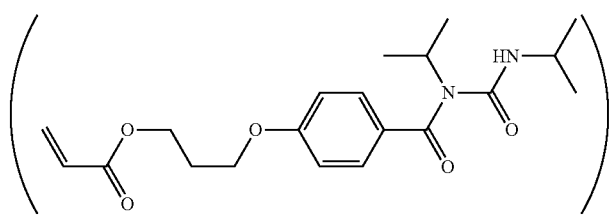

(I-6-A)

A reaction vessel was charged with 2.0 g of the compound represented by formula (I-6-1), 7.2 g of the compound represented by formula (I-6-2), 0.35 g of 4-dimethylaminopyridine, and 40 mL of dichloromethane in a nitrogen atmosphere. While the reaction vessel was cooled with ice, 4.0 g of diisopropylcarbodiimide was added dropwise, and the mixture was stirred at room temperature for 7 hours. After the resulting precipitate was removed by filtration, the solvent was removed by evaporation, and the product was dispersed in methanol and washed. The product was purified by column chromatography (silica gel, dichloromethane) and reprecipitation (dichloromethane/methanol) to thereby obtain 6.9 g of a compound represented by formula (I-6R). The yield of the compound represented by formula (I-6R) was 79%. After the reaction, the N-acylurea represented by formula (I-6-A) was found to be formed, and its amount was 8.6%. After the purification, the compound represented by formula (I-6R) was found to contain 0.2% of the N-acylurea represented by formula (I-6-A).

LC-MS: 603 [M+1]

(Example 7) Production of Compound Represented by Formula (I-7)

[Chem. 68]

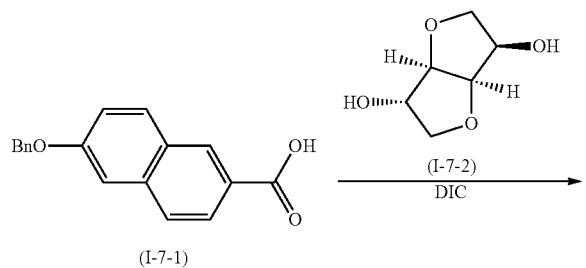

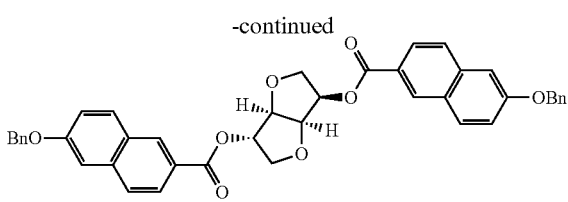

(I-7-A)

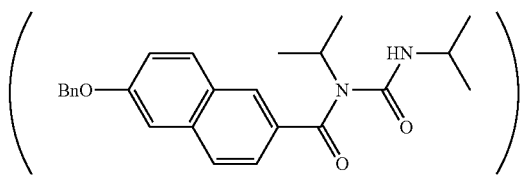

A reaction vessel was charged with 8.0 g of a compound represented by formula (I-7-1), 2.1 g of a compound represented by formula (I-7-2), 0.53 g of 4-dimethylaminopyridine, 100 mL of dichloromethane, and 5.7 mL of 1M hydrogen chloride/diethyl ether in a nitrogen atmosphere. While the reaction vessel was cooled with ice, 6.8 g of dicyclohexylcarbodiimide was added, and the mixture was stirred at room temperature for 7 hours. After the resulting precipitate was removed by filtration, the solvent was removed by evaporation, and the product was dispersed in methanol and washed. The product was purified by column chromatography (silica gel, dichloromethane) and reprecipitation (dichloromethane/methanol) to thereby obtain 8.0 g of a compound represented by formula (I-7). The yield of the compound represented by formula (I-7) was 84%. After the reaction, an N-acylurea represented by formula (I-7-A) was found to be formed, and its amount was 5.3%. After the purification, the N-acylurea represented by formula (I-7-A) was not detected in the compound represented by formula (I-7).

LC-MS: 667 [M+1]

105
(Comparative Example 7) Production of Compound Represented by Formula (I-7R)

[Chem. 69]

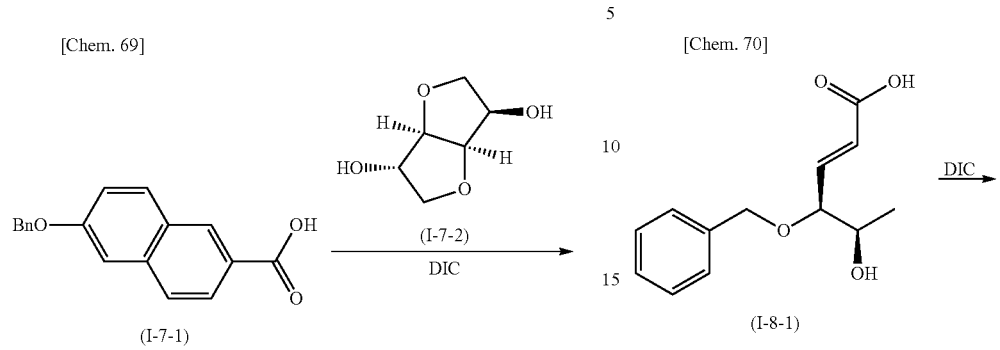

A reaction vessel was charged with 8.0 g of the compound represented by formula (I-7-1), 2.1 g of the compound represented by formula (I-7-2), 0.53 g of 4-dimethylaminopyridine, and 100 mL of dichloromethane in a nitrogen atmosphere. While the reaction vessel was cooled with ice, 6.8 g of dicyclohexylcarbodiimide was added, and the mixture was stirred at room temperature for 7 hours. After the resulting precipitate was removed by filtration, the solvent was removed by evaporation, and the product was dispersed in methanol and washed. The product was purified by column chromatography (silica gel, dichloromethane) and reprecipitation (dichloromethane/methanol) to thereby obtain 6.2 g of a compound represented by formula (I-7R). The yield of the compound represented by formula (I-7R) was 65%. After the reaction, the N-acylurea represented by formula (I-7-A) was found to be formed, and its amount was 18.7%. After the purification, the N-acylurea represented by formula (I-7-A) was detected in the compound represented by formula (I-7R).

LC-MS: 667 [M+1]

106
(Example 8) Production of Compound Represented by Formula (I-8)

[Chem. 70]

A reaction vessel was charged with 5.0 g of a compound represented by formula (I-8-1), 0.50 g of pyridine, 70 mL of dichloromethane, and 0.64 g of trifluoromethanesulfonic acid in a nitrogen atmosphere. While the reaction vessel was cooled with ice, 2.9 g of diisopropylcarbodiimide was added, and the mixture was stirred at room temperature for 20 hours. After the resulting precipitate was removed by filtration, the filtrate was washed with 1% hydrochloric acid, then water, and brine. The product was purified by column chromatography (silica gel, hexane/ethyl acetate) to thereby obtain 3.7 g of a compound represented by formula (I-8). The yield of the compound represented by formula (I-8) was 80%. After the reaction, an N-acylurea represented by formula (I-8-A) was found to be formed, and its amount was 1.3%. After the purification, the N-acylurea represented by formula (I-8-A) was not detected in the compound represented by formula (I-8).

LC-MS: 219 [M+1]

(Comparative Example 8) Production of Compound Represented by Formula (I-8R)

[Chem. 71]

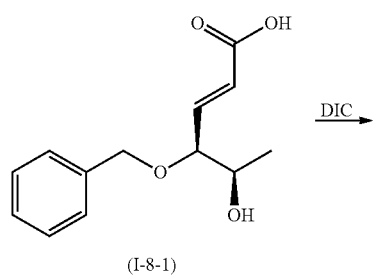

(I-8-1)

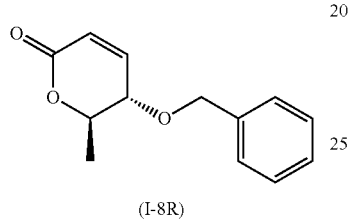

(I-8R)

(I-8-A)

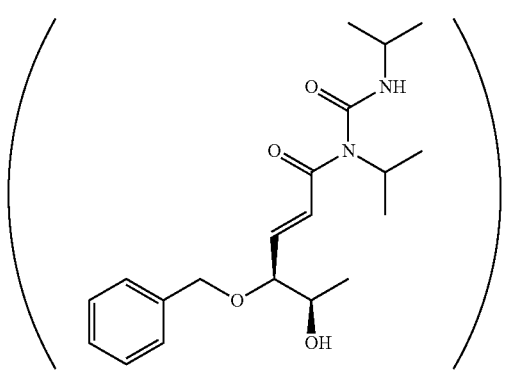

A reaction vessel was charged with 5.0 g of the compound represented by formula (I-8-1), 0.50 g of pyridine, and 70 mL of dichloromethane in a nitrogen atmosphere. While the reaction vessel was cooled with ice, 2.9 g of diisopropylcarbodiimide was added, and the mixture was stirred at room temperature for 20 hours. After the resulting precipitate was removed by filtration, the filtrate was washed with 1% hydrochloric acid, then water, and brine. The product was purified by column chromatography (silica gel, hexane/ethyl acetate) to thereby obtain 2.1 g of a compound represented by formula (I-8R). The yield of the compound represented by formula (I-8R) was 45%. After the reaction, the N-acylurea represented by formula (I-8-A) was found to be formed, and its amount was 13.8%. After the purification, the N-acylurea represented by formula (I-8-A) was not detected in the compound represented by formula (I-8R).

LC-MS: 219 [M+1]

(Example 9) Production of Compound Represented by Formula (I-9)

[Chem. 72]

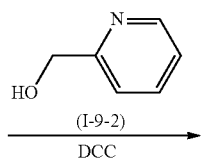

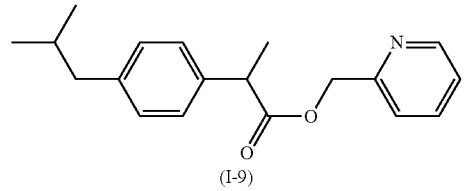

(I-9-1)

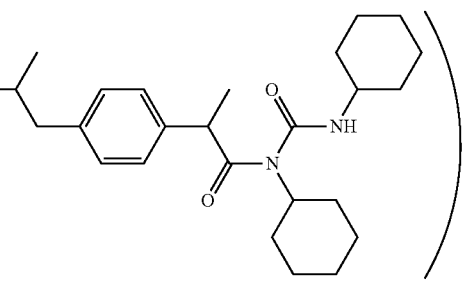

(I-9)

(I-9-A)

A reaction vessel was charged with 10.0 g of a compound represented by formula (I-9-1), 5.3 g of a compound represented by formula (I-9-2), 80 mL of dichloromethane, and 5.6 g of (±)-10-camphorsulfonic acid in a nitrogen atmosphere. While the reaction vessel was cooled with ice, 12.0 g of dicyclohexylcarbodiimide was added, and the mixture was stirred at room temperature for 20 hours. The product was purified by column chromatography (silica gel, hexane/ethyl acetate) to thereby obtain 8.8 g of a compound represented by formula (I-9). The yield of the compound represented by formula (I-9) was 61%. After the reaction, an N-acylurea represented by formula (I-9-A) was found to be formed, and its amount was 14.2%. After the purification, the N-acylurea represented by formula (I-9-A) was not detected in the compound represented by formula (I-9).

LC-MS: 298 [M+1]

(Comparative Example 9) Production of Compound Represented by Formula (I-9R)

[Chem. 73]

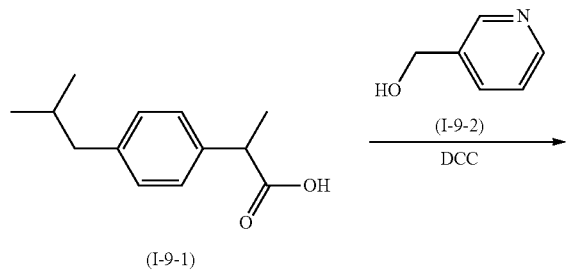

(I-9-1)

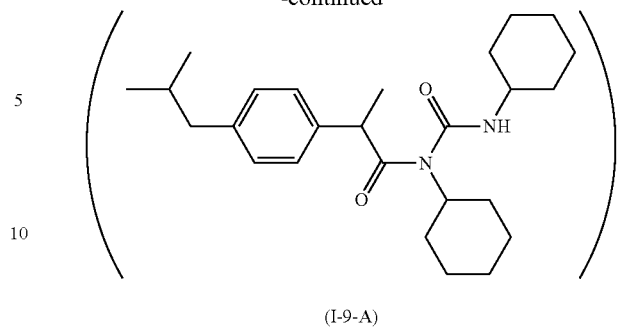

(I-9-A)

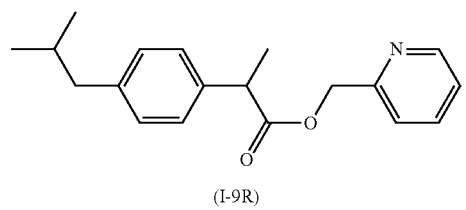

(I-9R)

A reaction vessel was charged with 10.0 g of the compound represented by formula (I-9-1), 5.3 g of the compound represented by formula (I-9-2), and 80 mL of dichloromethane in a nitrogen atmosphere. While the reaction vessel was cooled with ice, 12.0 g of dicyclohexylcarbodiimide was added, and the mixture was stirred at room temperature for 20 hours. The product was purified by column chromatography (silica gel, hexane/ethyl acetate) to thereby obtain 1.4 g of a compound represented by formula (I-9R). The yield of the compound represented by formula (I-9R) was 10%. After the reaction, the N-acylurea represented by formula (I-9-A) was found to be formed, and its amount was 52.6%. After the purification, the N-acylurea represented by formula (I-9-A) was not detected in the compound represented by formula (I-9R).

LC-MS: 298 [M+1]

(Example 10) Production of Compound Represented by Formula (I-10)

[Chem. 74]

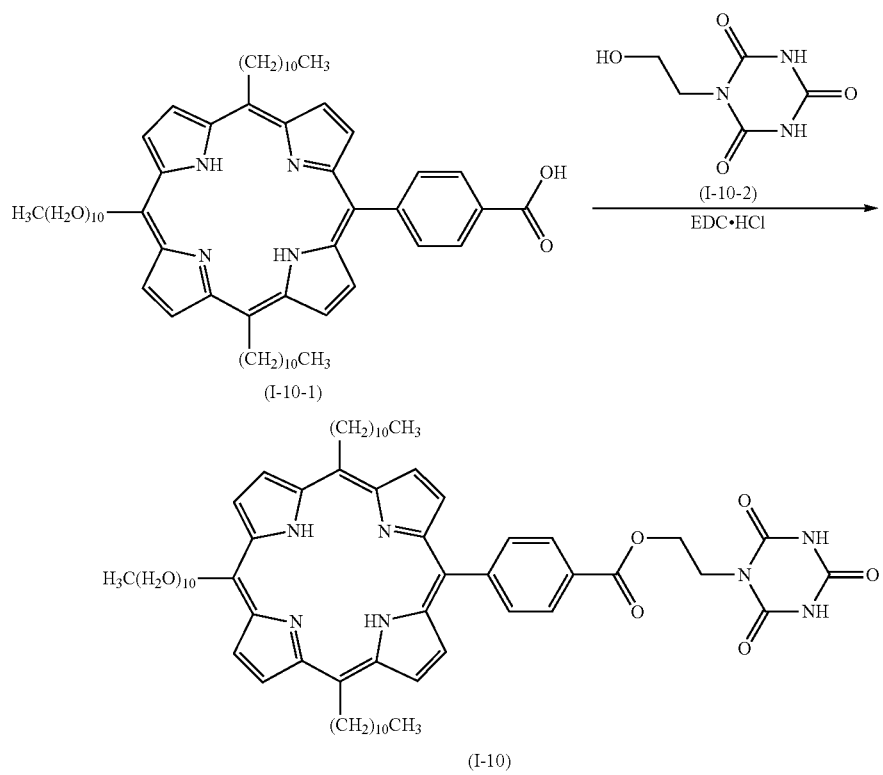

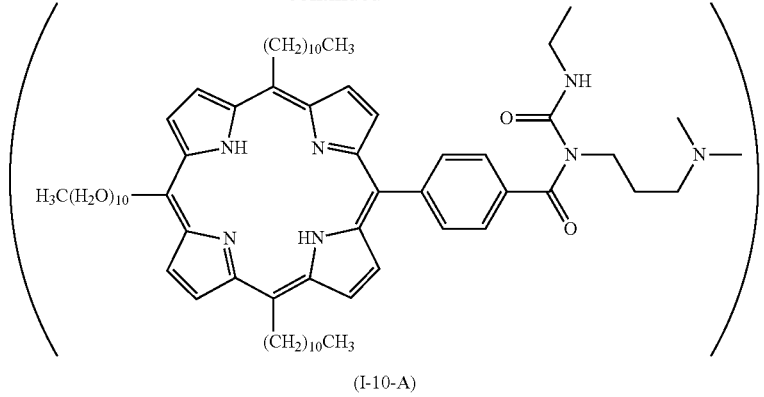

(I-10-A)

A reaction vessel was charged with 6.0 g of a compound represented by formula (I-10-1), 1.2 g of a compound represented by formula (I-10-2), 0.25 g of 4-dimethylaminopyridine, 600 mL of dichloromethane, and 0.26 g of methanesulfonic acid in a nitrogen atmosphere. While the reaction vessel was cooled with ice, 1.5 g of 1-(3-dimethylaminopropyl)-3-ethylcarbodiimide hydrochloride was added, and the mixture was stirred at room temperature for 48 hours. The product was purified by column chromatography (silica gel, dichloromethane/methanol) to thereby obtain 5.3 g of a compound represented by formula (I-10).

The yield of the compound represented by formula (I-10) was 75%. After the reaction, an N-acylurea represented by formula (I-10-A) was found to be formed, and its amount was 5.8%. After the purification, the N-acylurea represented by formula (I-10-A) was not detected in the compound represented by formula (I-10).

LC-MS: 1048 [M+1]

(Comparative Example 10) Production of Compound Represented by Formula (I-10R)

[Chem. 75]

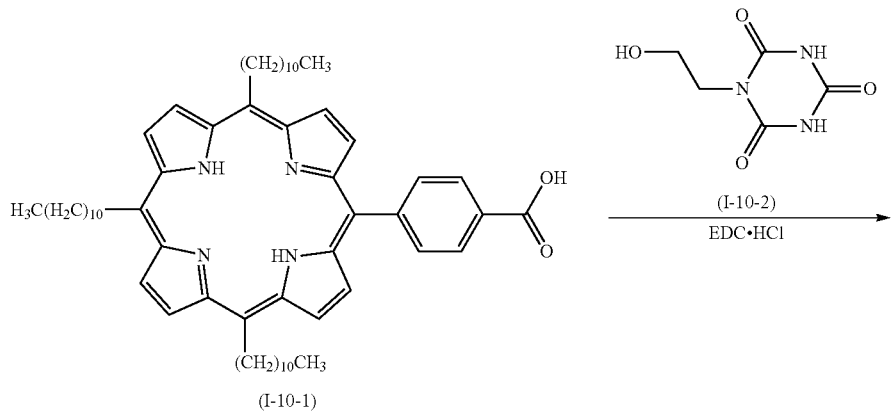

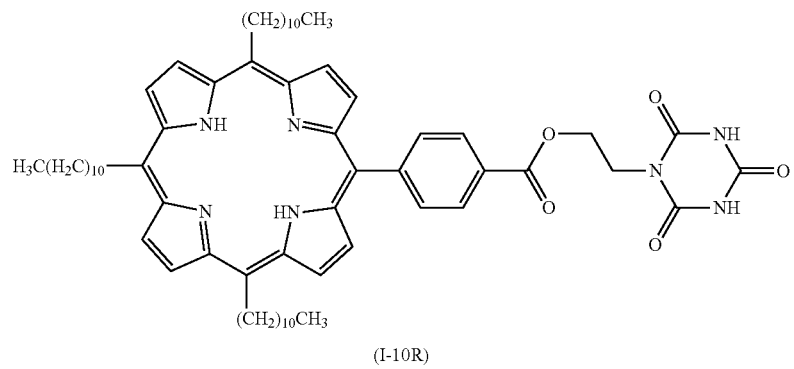

(I-10R)

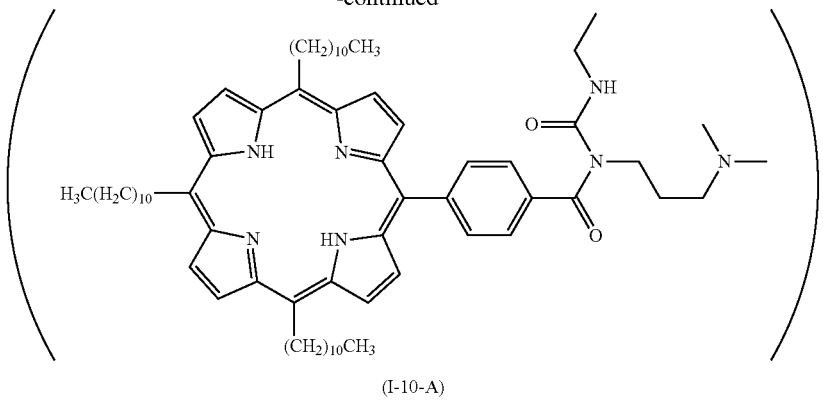

(I-10-A)

A reaction vessel was charged with 6.0 g of the compound represented by formula (I-10-1), 1.2 g of the compound represented by formula (I-10-2), 0.25 g of 4-dimethylaminopyridine, and 600 mL of dichloromethane in a nitrogen atmosphere. While the reaction vessel was cooled with ice, 1.5 g of 1-(3-dimethylaminopropyl)-3-ethylcarbodiimide hydrochloride was added, and the mixture was stirred at room temperature for 48 hours. The product was purified by column chromatography (silica gel, dichloromethane/methanol) to thereby obtain 3.2 g of a compound represented by formula (I-10R). The yield of the compound represented by formula (I-10R) was 46%. After the reaction, the N-acylurea represented by formula (I-10-A) was found to be formed, and its amount was 38.1%. After the purification, the N-acylurea represented by formula (I-10-A) was not detected in the compound represented by formula (I-10R).

LC-MS: 1048 [M+1]

(Example 11) Production of Compound Represented by Formula (I-11)

[Chem. 76]

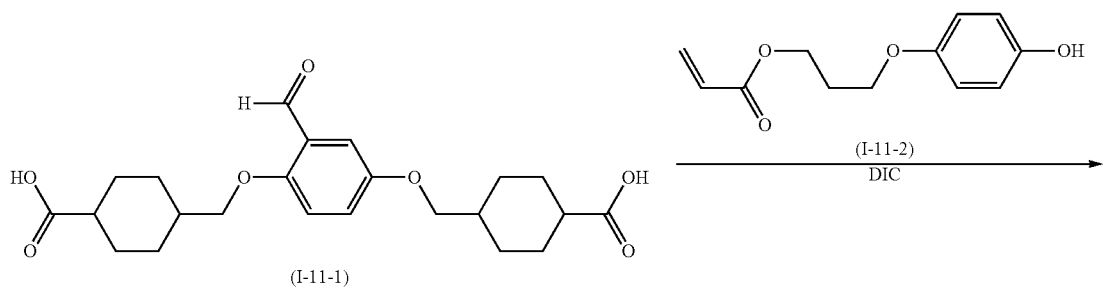

(I-11-1)

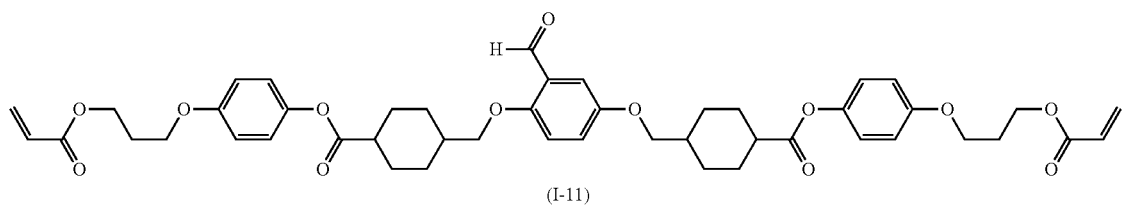

(I-11)

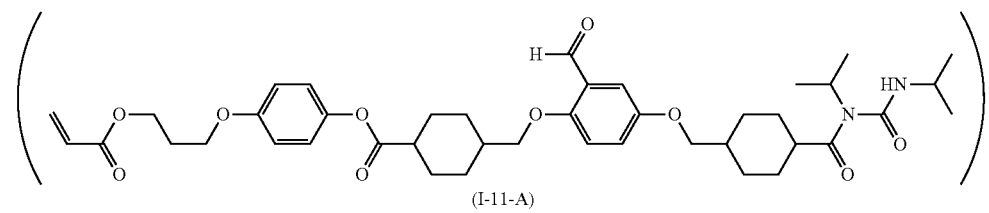

(I-11-A)

A reaction vessel was charged with 3.0 g of a compound represented by formula (I-11-1), 3.2 g of a compound represented by formula (I-11-2), 0.26 g of 4-dimethylaminopyridine, 50 mL of dichloromethane, and 0.28 g of methanesulfonic acid in a nitrogen atmosphere. While the reaction vessel was cooled with ice, 2.1 g of diisopropylcarbodiimide was added dropwise, and the mixture was stirred at 40° C. for 5 hours. After the resulting precipitate was removed by filtration, the solvent was removed by evaporation, and the product was dispersed in methanol and washed. The product was purified by column chromatography (silica gel, dichloromethane) and reprecipitation (dichloromethane/methanol) to thereby obtain 5.3 g of a compound represented by formula (I-11). The yield of the compound represented by formula (I-11) was 90%. After the reaction, an N-acylurea represented by formula (I-11-A) was found to be formed, and its amount was 1.4%. After the purification, the N-acylurea represented by formula (I-11-A) was not detected in the compound represented by formula (I-11).

LC-MS: 827 [M+1]

(Comparative Example 11) Production of Compound Represented by Formula (I-11R)

[Chem. 77]

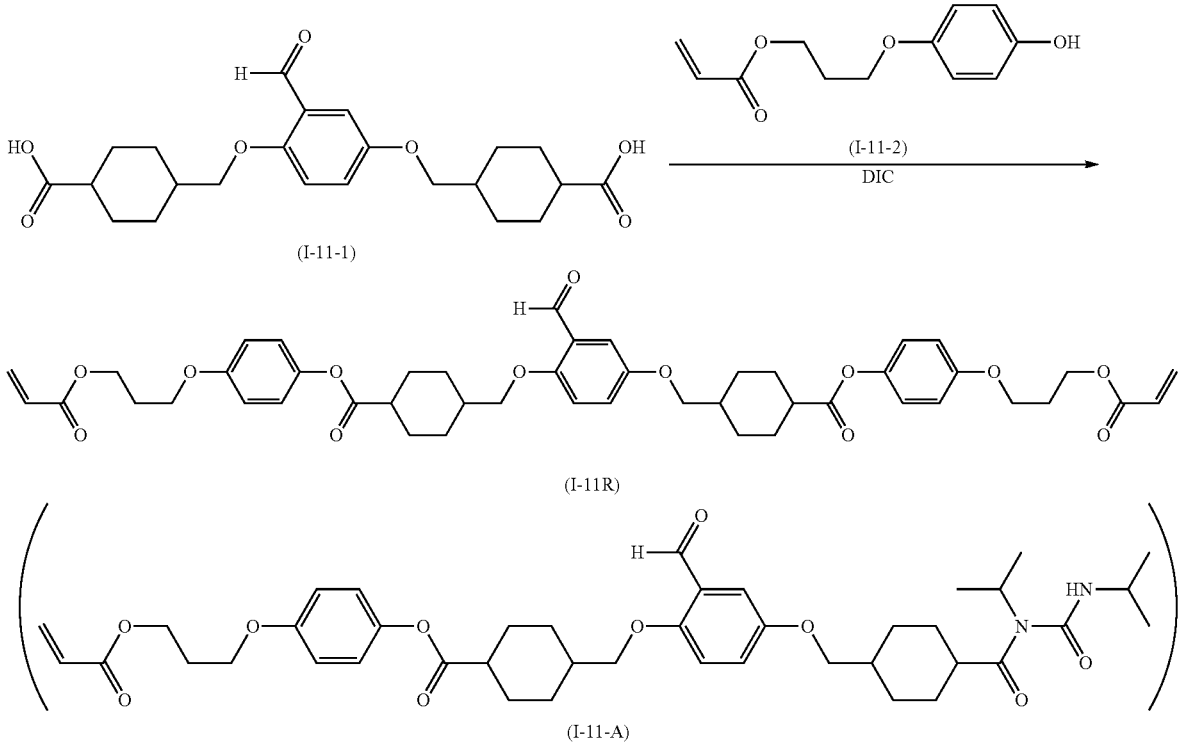

A reaction vessel was charged with 3.0 g of the compound represented by formula (I-11-1), 3.2 g of the compound represented by formula (I-11-2), 0.26 g of 4-dimethylaminopyridine, 50 mL of dichloromethane, and 0.28 g of methanesulfonic acid in a nitrogen atmosphere. While the reaction vessel was cooled with ice, 2.1 g of diisopropylcarbodiimide was added dropwise, and the mixture was stirred at 40° C. for 5 hours. After the resulting precipitate was removed by filtration, the solvent was removed by evaporation, and the product was dispersed in methanol and washed. The product was purified by column chromatography (silica gel, dichloromethane) and reprecipitation (dichloromethane/methanol) to thereby obtain 3.3 g of a compound represented by formula (I-11R). The yield of the compound represented by formula (I-11R) was 56%. After the reaction, the N-acylurea represented by formula (I-11-A) was found to be formed, and its amount was 29.5%. After the purification, the N-acylurea represented by formula (I-11-A) was not detected in the compound represented by formula (I-11R).

LC-MS: 827 [M+1]

(Example 12) Production of Compound Represented by Formula (I-12)

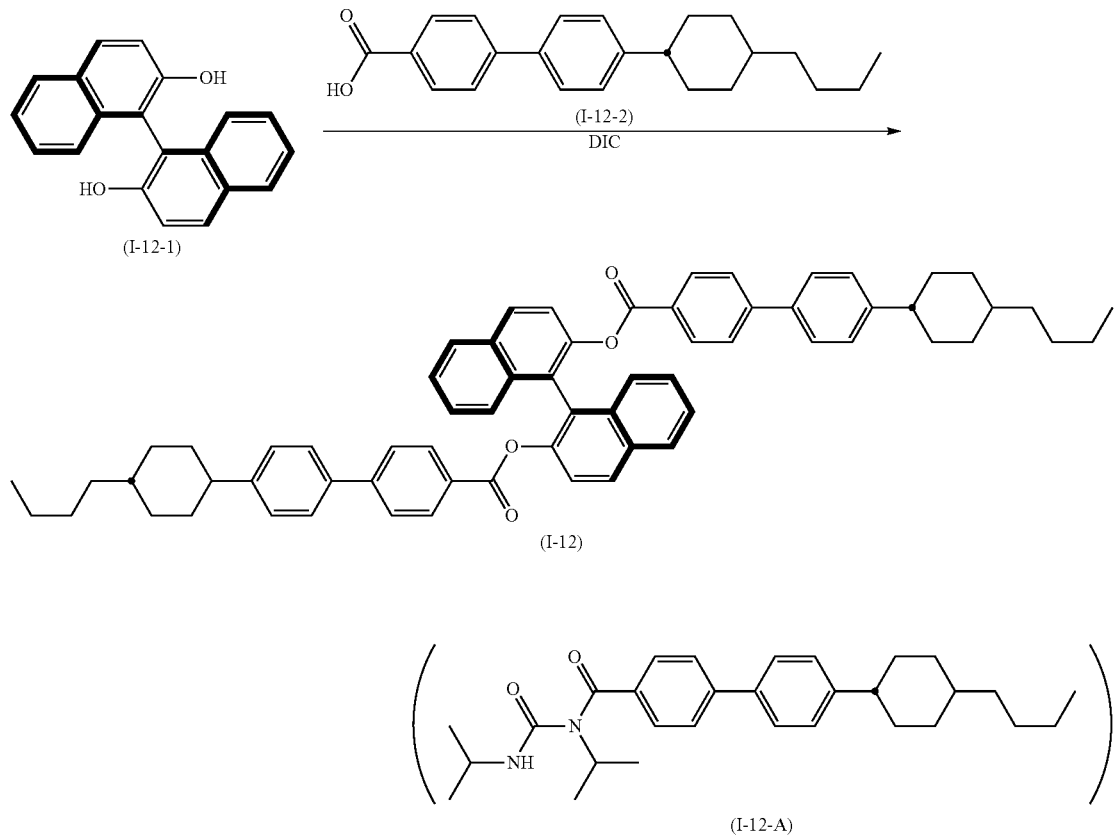

A reaction vessel was charged with 3.0 g of a compound represented by formula (I-12-1), 7.05 g of a compound represented by formula (I-12-2), 0.13 g of 4-dimethylaminopyridine, 50 mL of dichloromethane, and 0.40 g of methanesulfonic acid in a nitrogen atmosphere. While the reaction vessel was cooled with ice, 2.8 g of diisopropylcarbodiimide was added dropwise, and the mixture was stirred at room temperature for 5 hours. After the resulting precipitate was removed by filtration, the solvent was removed by evaporation. The product was purified by column chromatography (silica gel, dichloromethane) and reprecipitation (dichloromethane/methanol) to thereby obtain 7.7 g of a compound represented by formula (I-12). The yield of the compound represented by formula (I-12) was 80%. After the reaction, an N-acylurea represented by formula (I-12-A) was found to be formed, and its amount was 1.2%. After the purification, the N-acylurea represented by formula (I-12-A) was not detected in the compound represented by formula (I-12).

LC-MS: 923 [M+1]

(Comparative Example 12) Production of Compound Represented by Formula (I-12R)

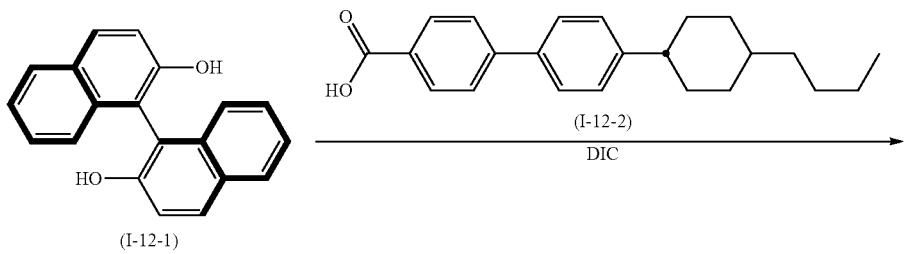

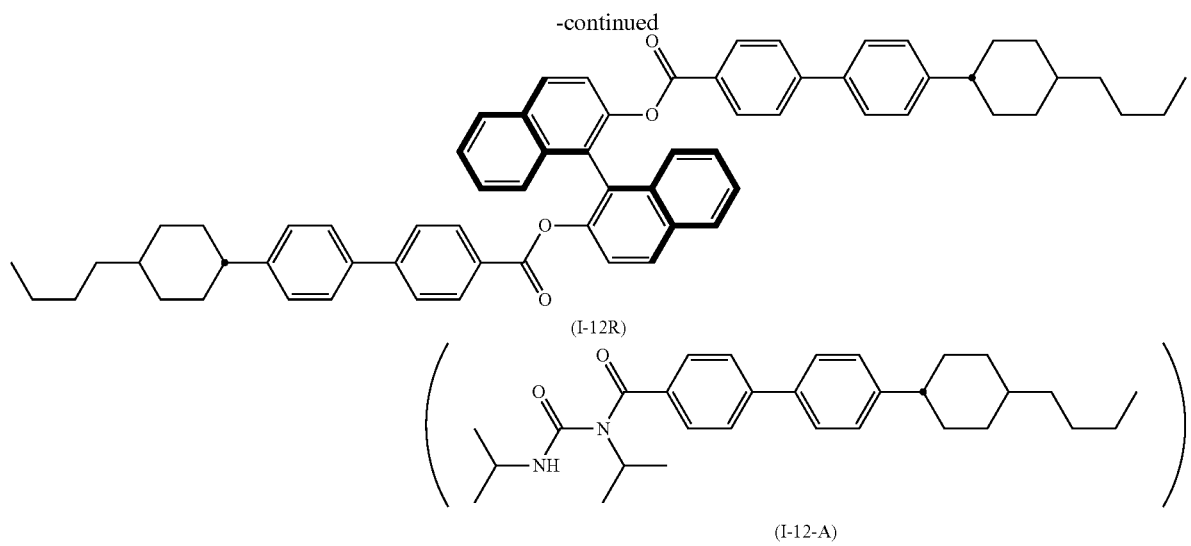

(I-12R)

(I-12-A)

A reaction vessel was charged with 3.0 g of the compound represented by formula (I-12-1), 7.05 g of the compound represented by formula (I-12-2), 0.13 g of 4-dimethylaminopyridine, and 50 mL of dichloromethane in a nitrogen atmosphere. While the reaction vessel was cooled with ice, 2.8 g of diisopropylcarbodiimide was added dropwise, and the mixture was stirred at room temperature for 5 hours. After the resulting precipitate was removed by filtration, the solvent was removed by evaporation. The product was purified by column chromatography (silica gel, dichloromethane) and reprecipitation (dichloromethane/methanol) to thereby obtain 7.8 g of a compound represented by formula (I-12). The yield of the compound represented by formula (I-12R) was 81%. After the reaction, the N-acylurea represented by formula (I-12-A) was found to be formed, and its amount was 5.3%. After the purification, the compound represented by formula (I-12) was found to contain 0.026% of the N-acylurea represented by formula (I-12-A).

LC-MS: 923 [M+1]

As can be seen from the above results, with the production method of the present invention, an N-acylurea is less likely to be produced as a by-product. Therefore, the production method of the present invention is useful as a method for producing an ester group-containing compound.

(Example 13) Production of Compound Represented by Formula (II-1) Using Compound Represented by Formula (I-3) and Produced by Production Method of Invention

[Chem. 80]

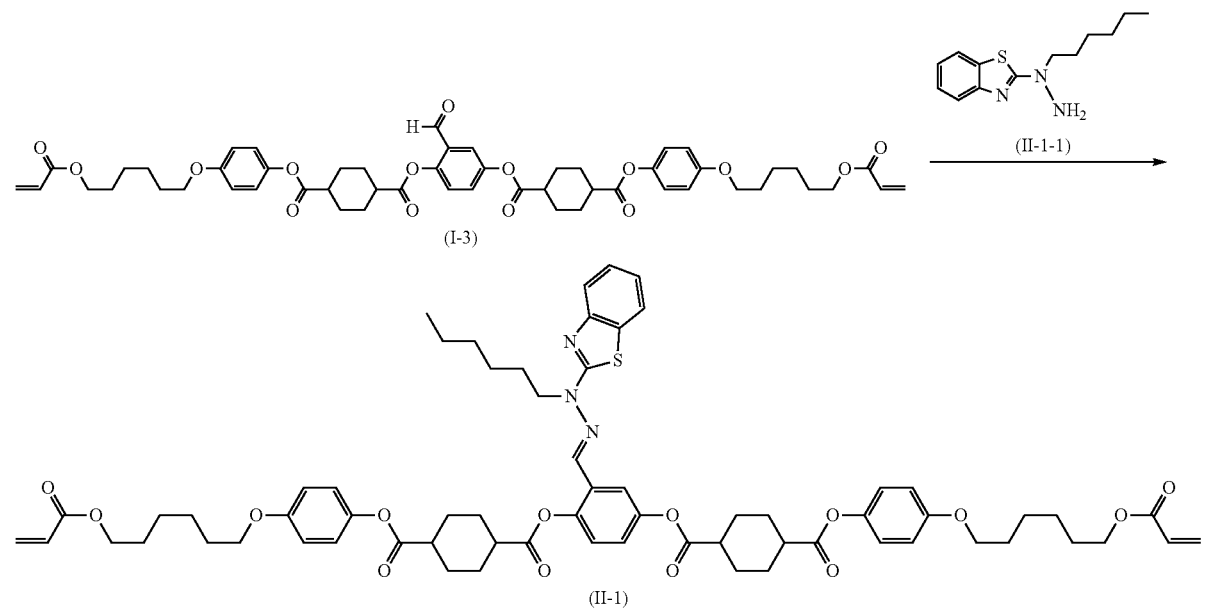

A reaction vessel was charged with 3.0 g of the compound represented by formula (I-3), 0.80 g of a compound represented by formula (II-1-1), 0.15 g of (±)-10-camphorsulfonic acid, 10 mL of tetrahydrofuran, and 5 mL of ethanol in a nitrogen atmosphere, and the mixture was heated to 50° C. and stirred for 6 hours. The solvent was removed by evaporation, and the solid obtained was dispersed in methanol and washed. The product was purified by column chromatography (silica gel, dichloromethane) and recrystallization (dichloromethane/methanol) to thereby obtain 2.8 g of a compound represented by formula (II-1).

$^1$H NMR (CDCl$_3$) δ 0.90 (t, 3H), 1.31-1.54 (m, 14H), 1.66-1.82 (m, 18H), 2.31-2.35 (m, 8H), 2.58-2.70 (m, 4H), 3.95 (t, 4H), 4.18 (t, 4H), 4.30 (t, 2H), 5.82 (t, 2H), 6.13 (dd, 2H), 6.40 (dd, 2H), 6.88 (d, 4H), 6.98 (d, 2H), 6.99 (d, 2H), 7.10 (dd, 1H), 7.12 (d, 1H), 7.17 (ddd, 1H), 7.34 (ddd, 1H), 7.67-7.70 (m, 3H), 7.75 (d, 1H) ppm.

LC-MS: 1170 [M+1]

(Comparative Example 13) Production of Compound Represented by Formula (II-1R) Using Compound Represented by Formula (I-3R) and Produced by Known Production Method

[Chem. 81]
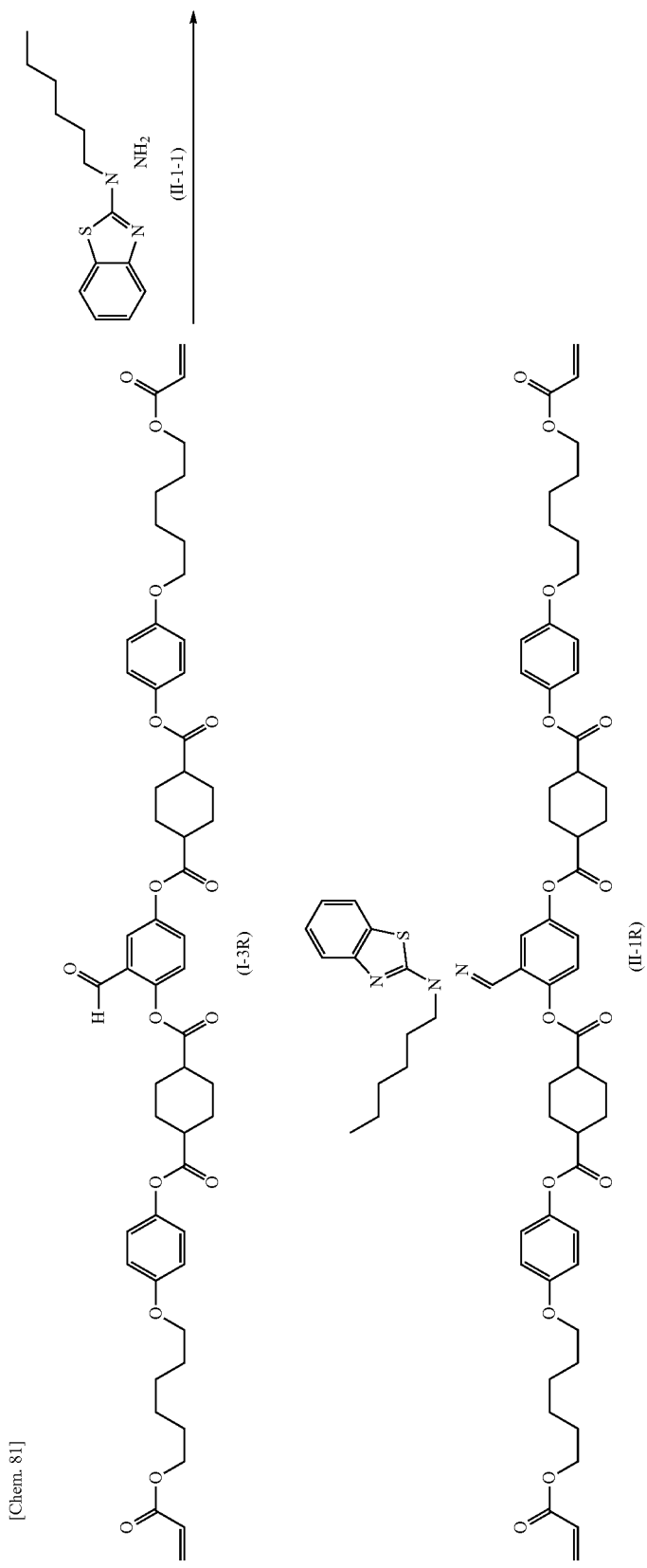

A compound represented by formula (II-1R) was produced in the same manner as in Example 13 except that the compound represented by formula (I-3) was replaced with the compound represented by formula (I-3R).

(Example 14) Production of Compound Represented by Formula (II-2) Using Compound Represented by Formula (I-4) and Produced by Production Method of Invention

[Chem. 82]
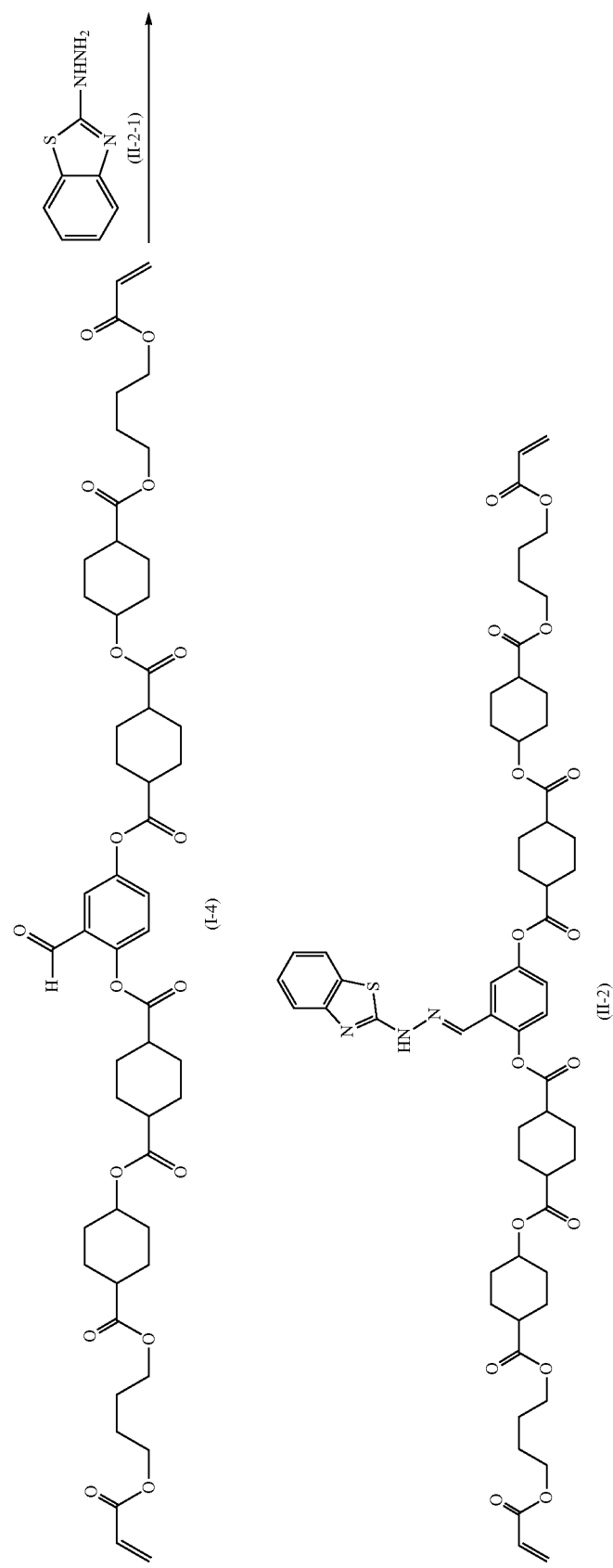

A reaction vessel was charged with 3.0 g of the compound represented by formula (I-4), 0.52 g of a compound represented by formula (II-2-1), 0.15 g of (±)-10-camphorsulfonic acid, 10 mL of tetrahydrofuran, and 5 mL of ethanol in a nitrogen atmosphere, and the mixture was stirred at room temperature for 8 hours. The solvent was removed by evaporation, and the solid obtained was dispersed in methanol and washed. The product was purified by column chromatography (silica gel, dichloromethane) and recrystallization (dichloromethane/methanol) to thereby obtain 2.6 g of a compound represented by formula (II-2).

LC-MS: 1098 [M+1]

(Comparative Example 14) Production of Compound Represented by Formula (II-2R) Using Compound Represented by Formula (I-4R) and Produced by Known Production Method

[Chem. 83]
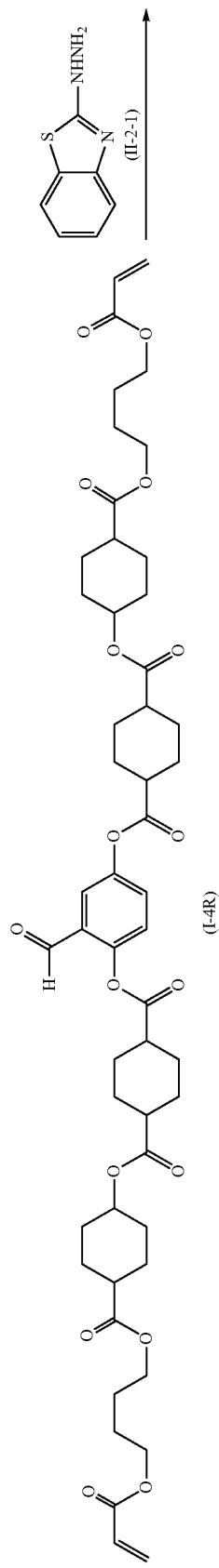
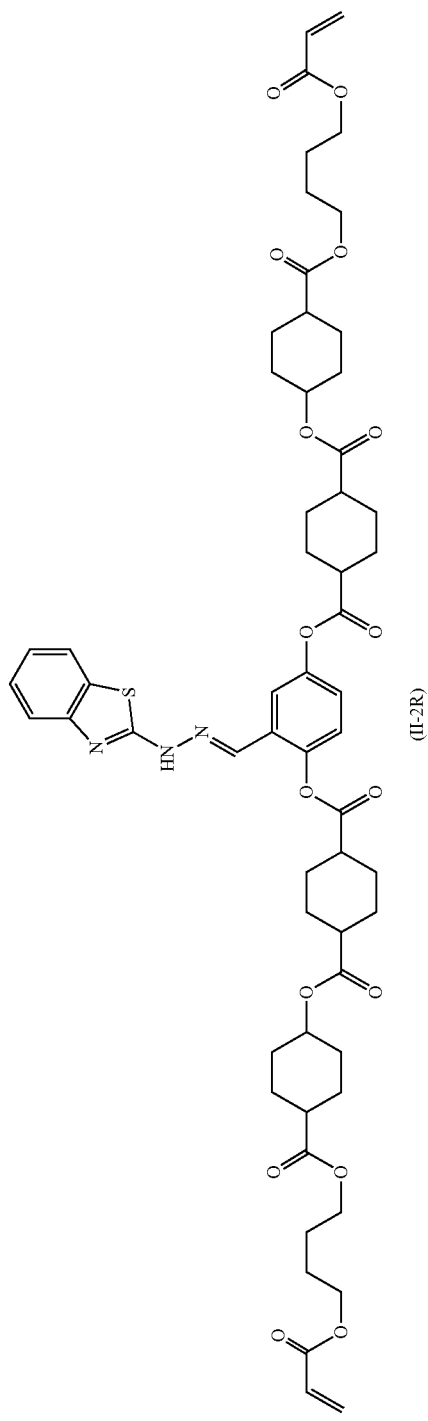

A compound represented by formula (II-2R) was produced in the same manner as in Example 14 except that the compound represented by formula (I-4) was replaced with the compound represented by formula (I-4R).

(Example 15) Production of Compound Represented by Formula (II-3) Using Compound Represented by Formula (I-5) and Produced by Production Method of Invention

[Chem. 84]

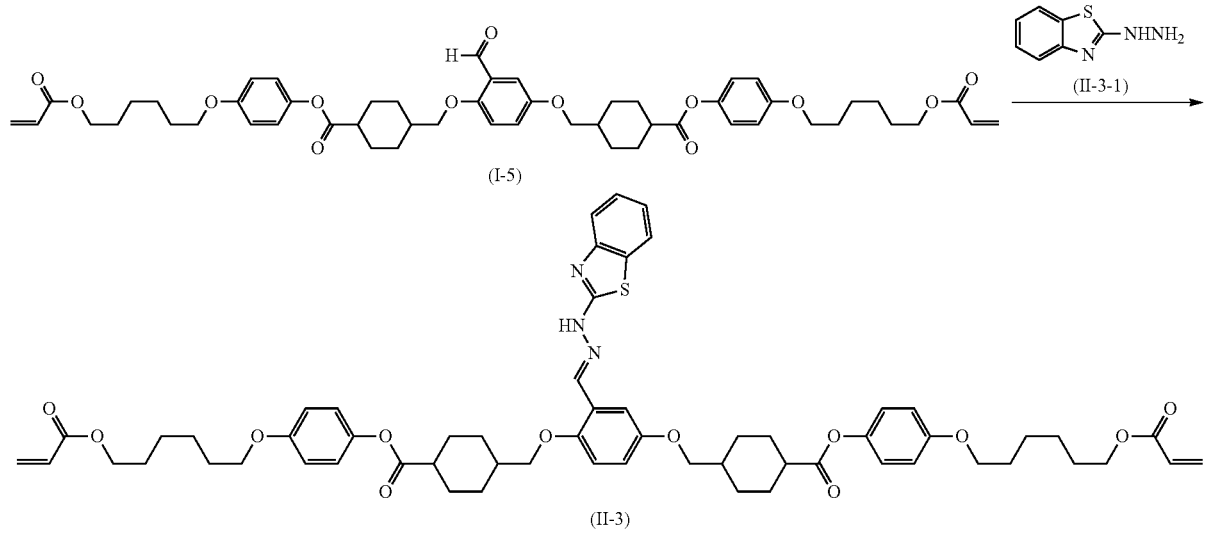

A reaction vessel was charged with 3.0 g of the compound represented by formula (I-5), 0.54 g of a compound represented by formula (II-3-1), 0.15 g of (±)-10-camphorsulfonic acid, 10 mL of tetrahydrofuran, and 5 mL of ethanol in a nitrogen atmosphere, and the mixture was stirred at room temperature for 8 hours. The solvent was removed by evaporation, and the solid obtained was dispersed in methanol and washed. The product was purified by column chromatography (silica gel, dichloromethane) and recrystallization (dichloromethane/methanol) to thereby obtain 2.6 g of a compound represented by formula (II-3).

Transition temperature (temperature rise rate: ° C./minute) C 90-110 N 182-187 I $^1$H NMR (CDCl$_3$) δ 1.07 (q, 2H), 1.24 (q, 2H), 1.47-1.90 (m, 24H), 2.09 (m, 4H), 2.22 (d, 2H), 2.39 (t, 1H), 2.53 (t, 1H), 3.74 (d, 2H), 3.85 (d, 2H), 3.94 (td, 4H), 4.17 (td, 4H), 5.82 (d, 2H), 6.13 (dd, 2H), 6.40 (d, 2H), 6.80-6.99 (m, 6H), 6.98 (d, 4H), 7.16 (t, 1H), 7.33 (t, 1H), 7.55 (m, 2H), 7.67 (d, 1H), 8.40 (s, 1H) ppm.

LC-MS: 1058 [M+1]

(Comparative Example 15) Production of Compound Represented by Formula (II-3R) Using Compound Represented by Formula (I-5R) and Produced by Known Production Method

[Chem. 85]
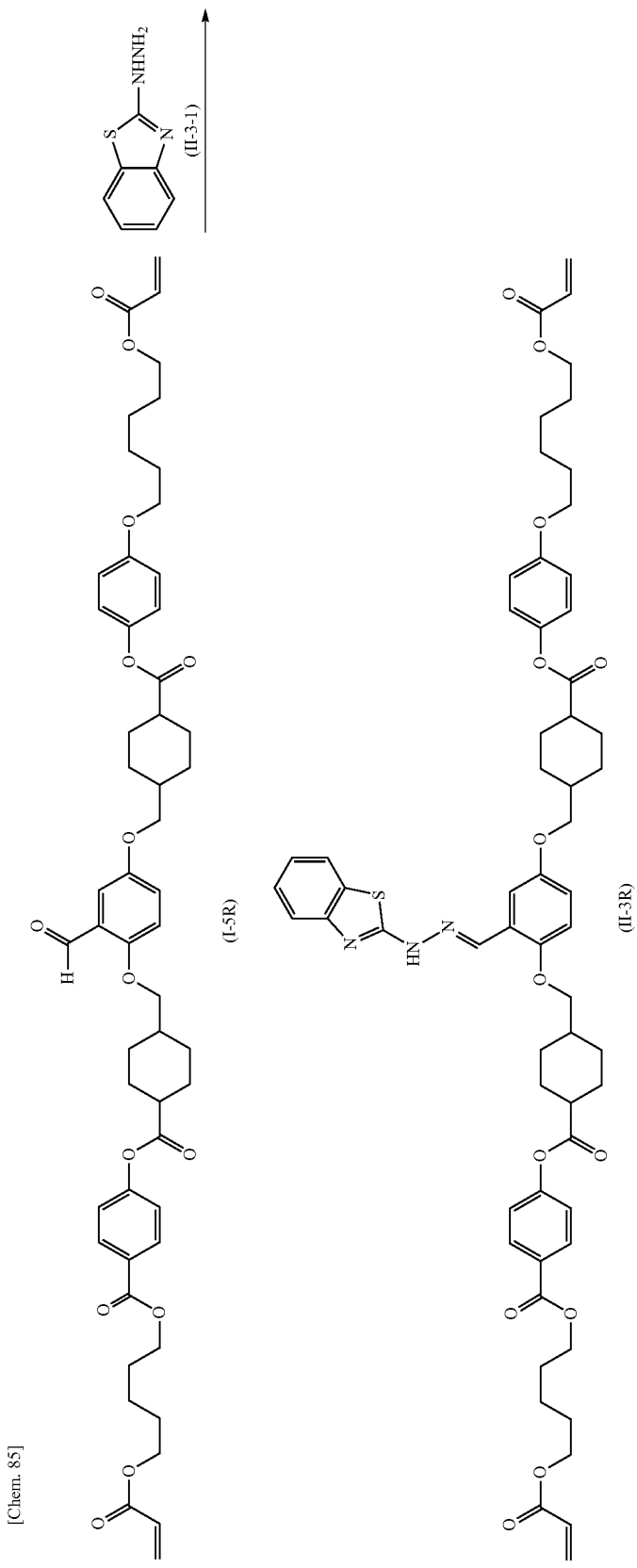

A compound represented by formula (II-3R) was produced in the same manner as in Example 15 except that the compound represented by formula (I-5) was replaced with the compound represented by formula (I-5R).

(Example 16) Production of Compound Represented by Formula (II-4) Using Compound Represented by Formula (I-7) and Produced by Production Method of Invention

[Chem. 86]

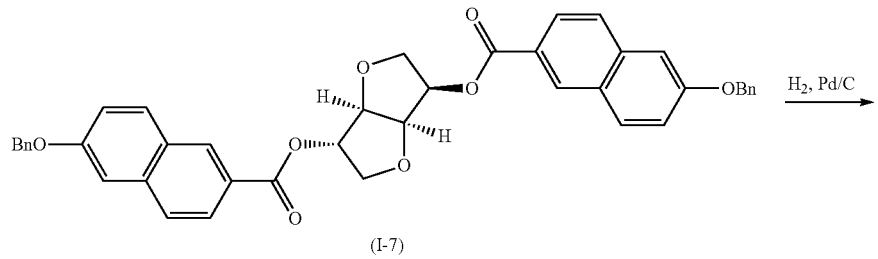

(I-7)

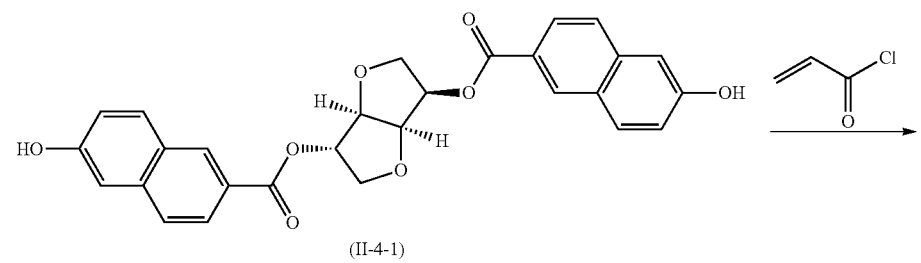

(II-4-1)

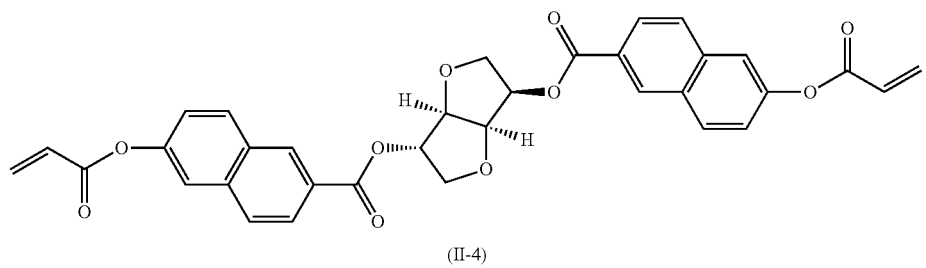

(II-4)

A pressure vessel was charged with 5.0 g of the compound represented by formula (I-7), 50 mL of tetrahydrofuran, 10 mL of ethanol, and 0.50 g of palladium 5% on carbon, and the mixture was heated to 50° C. and stirred at a hydrogen pressure of 0.5 MPa for 8 hours. After the catalyst was removed, the solvent was removed by evaporation, and the product was dried to thereby obtain 3.5 g of a compound represented by formula (II-4-1).

A reaction vessel was charged with 3.5 g of the compound represented by formula (II-4-1), 2.2 g of diisopropylethylamine, and 70 mL of dichloromethane in a nitrogen atmosphere. While the reaction vessel was cooled with ice, 1.5 g of acryloyl chloride was added dropwise, and the mixture was stirred at room temperature for 6 hours. The resulting mixture was washed with 1% hydrochloric acid, then water, and brine. The product was purified by column chromatography (silica gel, dichloromethane) and recrystallization (dichloromethane/methanol) to thereby obtain 3.2 g of a compound represented by formula (II-4).

LC-MS: 595 [M+1]

(Comparative Example 16) Production of Compound Represented by Formula (II-4R) Using Compound Represented by Formula (I-7R) and Produced by Well-Known Method

[Chem. 87]

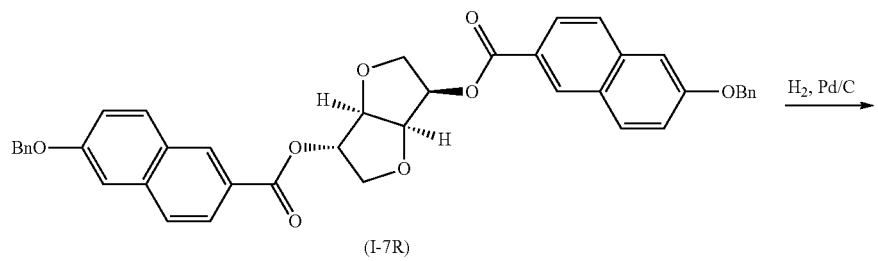

(I-7R)

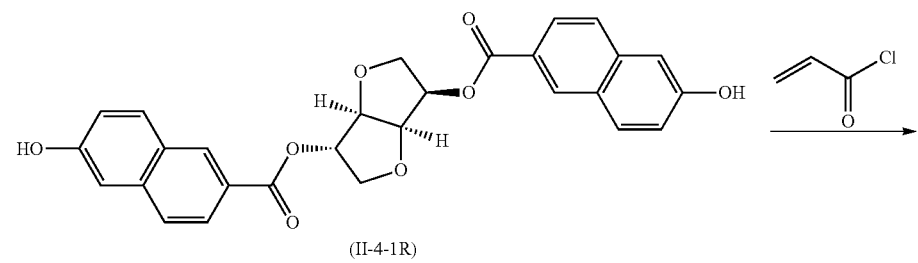

(II-4-1R)

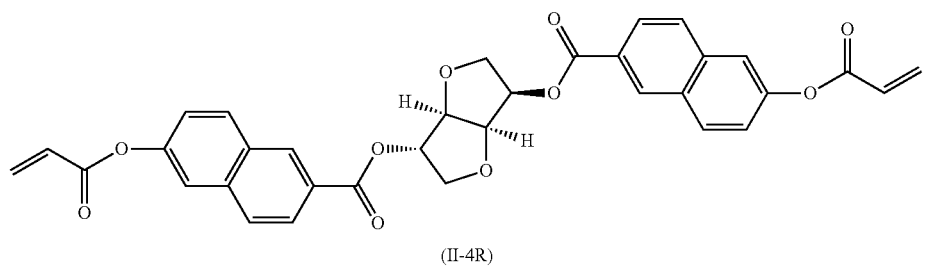

(II-4R)

A compound represented by formula (II-4R) was produced in the same manner as in Example 16 except that the compound represented by formula (I-7) was replaced with the compound represented by formula (I-7R).

(Example 17) Production of Compound Represented by Formula (II-5) Using Compound Represented by Formula (I-11) and Produced by Production Method of Invention

[Chem. 88]

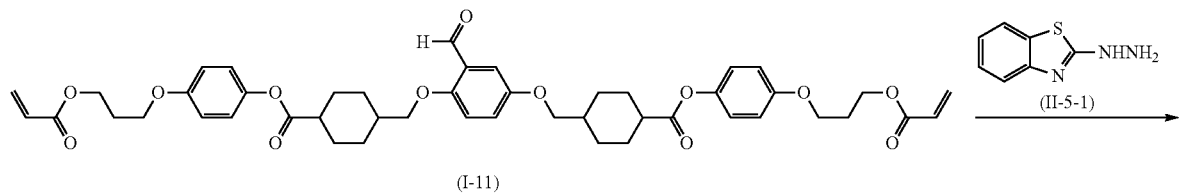

(I-11)

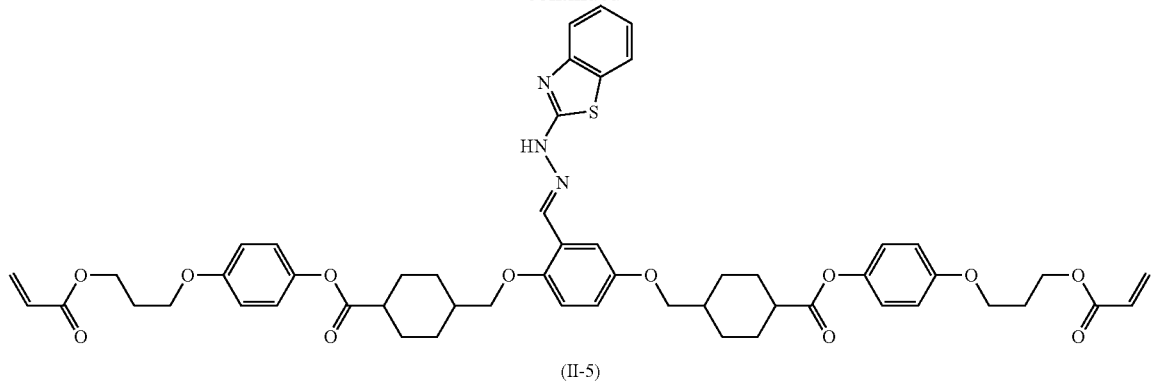

(II-5)

A reaction vessel was charged with 3.0 g of the compound represented by formula (I-11), 0.60 g of a compound represented by formula (II-5-1), 0.25 g of (±)-10-camphorsulfonic acid, 20 mL of tetrahydrofuran, and 5 mL of ethanol in a nitrogen atmosphere, and the mixture was stirred at room temperature for 8 hours. The solvent was removed by evaporation, and the solid obtained was dispersed in methanol and washed. The product was purified by column chromatography (silica gel, dichloromethane) and recrystallization (dichloromethane/methanol) to thereby obtain 2.5 g of a compound represented by formula (II-5).

Transition temperature (temperature rise rate: 5° C./minute) C 155 N>220 I $^1$H NMR (CDCl$_3$) δ 1.12 (q, 2H), 1.26 (q, 2H), 1.50 (q, 2H), 1.67 (qd, 2H), 1.91-2.27 (m, 14H), 2.43 (t, 1H), 2.56 (tt, 2H), 3.77 (d, 2H), 3.88 (d, 2H), 4.09 (t, 4H), 4.40 (t, 4H), 5.88 (d, 2H), 6.17 (ddd, 2H), 6.45 (d, 2H), 6.85 (d, 1H), 6.92 (m, 5H), 7.02 (d, 4H), 7.19 (t, 1H), 7.37 (t, 1H), 7.59 (m, 2H), 7.71 (d, 1H), 8.44 (s, 1H) ppm.

LC-MS: 974 [M+1]

(Comparative Example 17) Production of Compound Represented by Formula (II-5R) Using Compound Represented by Formula (I-11R) and Produced by Known Production Method

[Chem. 89]

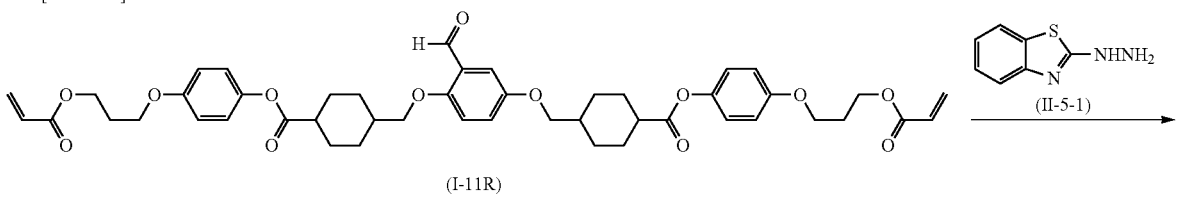

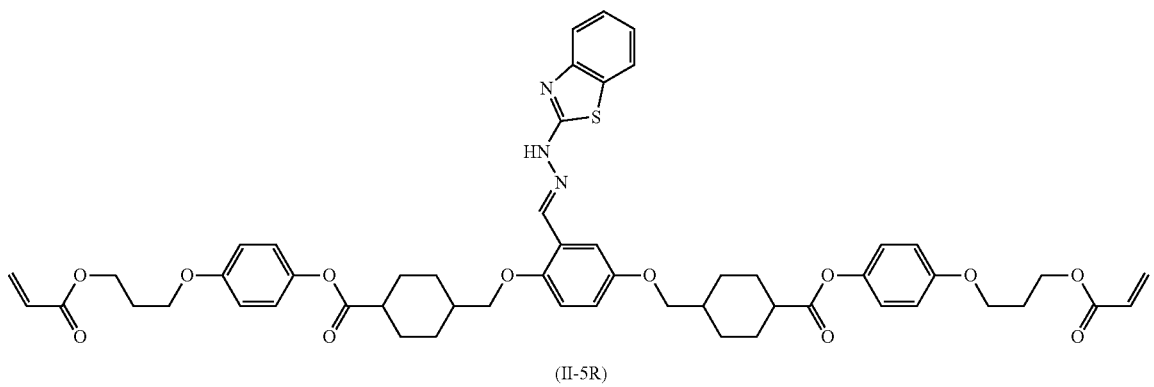

A compound represented by formula (II-5R) was produced in the same manner as in Example 17 except that the compound represented by formula (I-11) was replaced with the compound represented by formula (I-11R).

(Example 18) Production of Compound Represented by Formula (II-6) Using Compound Represented by Formula (I-5) and Produced by Production Method of Invention

[Chem. 90]

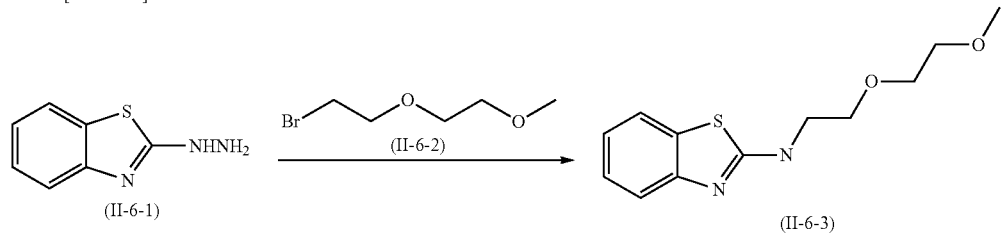

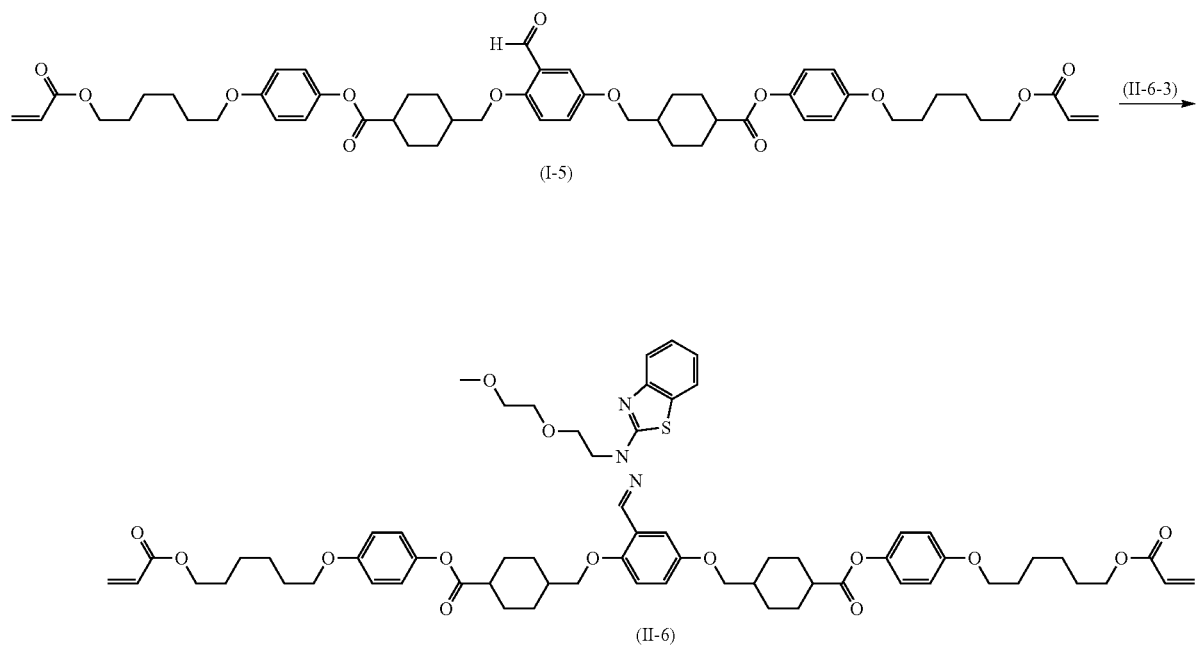

A reaction vessel was charged with 1.2 g of sodium amide and 5 mL of tetrahydrofuran in a nitrogen atmosphere. While the reaction vessel was cooled with ice, a solution mixture prepared by suspending 5.0 g of a compound represented by formula (II-6-1) in 10 mL of tetrahydrofuran was added dropwise, and the mixture was stirred at room temperature for 3 hours. After nitrogen gas was blown for two hours, a solution prepared by dissolving 6.1 g of a compound represented by formula (II-6-2) in 6 mL of tetrahydrofuran was added dropwise, and the mixture was stirred at room temperature for 5 hours. The resulting mixture was diluted with dichloromethane and washed with water and then brine. The product was purified by column chromatography (alumina, dichloromethane) and dispersion washing (hexane) to thereby obtain 6.5 g of a compound represented by formula (II-6-3).

A reaction vessel was charged with 3.0 g of the compound represented by formula (I-5), 0.88 g of a compound represented by formula (II-6-3), 0.23 g of (±)-10-camphorsulfonic acid, 20 mL of tetrahydrofuran, and 5 mL of ethanol in a nitrogen atmosphere, and the mixture was heated to 50° C. and stirred for 6 hours. The solvent was removed by evaporation, and the solid obtained was dispersed in methanol and washed. The product was purified by column chromatography (silica gel, dichloromethane) and recrystallization (dichloromethane/methanol) to thereby obtain 3.1 g of a compound represented by formula (II-6).

Transition temperature (temperature rise: 5° C./minute): C 85 N 128 I $^1$H NMR (CDCl$_3$) δ 1.22-1.28 (m, 4H), 1.44-1.47 (m, 8H), 1.60-1.82 (m, 12H), 1.90 (m, 2H), 2.07 (t, 4H), 2.24 (d, 4H), 2.53 (m, 2H), 3.30 (s, 3H), 3.50 (t, 2H), 3.66 (t, 2H), 3.85-3.89 (m, 6H), 3.93 (t, 4H), 4.17 (t, 4H), 4.53 (t, 2H), 5.82 (d, 2H), 6.13 (q, 2H), 6.40 (d, 2H), 6.83-6.90 (m, 6H), 6.95-6.98 (m, 4H), 7.14 (t, 1H), 7.32 (t, 1H), 7.52 (t, 1H), 7.67 (t, 2H), 8.33 (s, 1H) ppm.

LC-MS: 1160 [M+1]

(Comparative Example 18) Production of Compound Represented by Formula (II-6R) Using Compound Represented by Formula (I-5R) and Produced by Known Production Method

[Chem. 91]

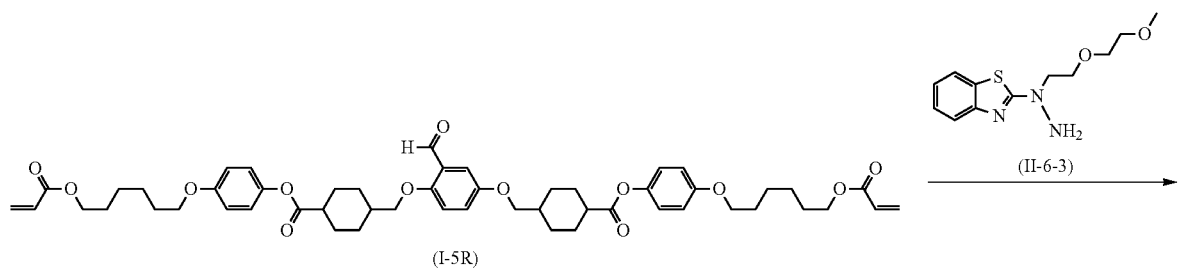

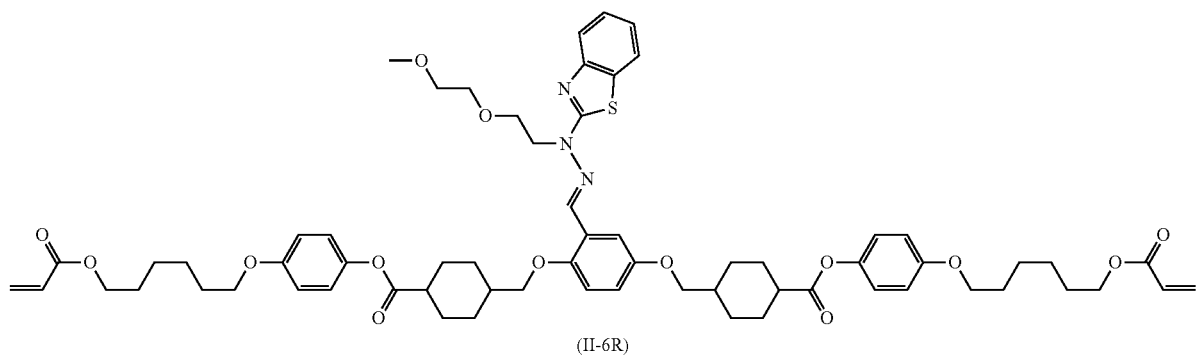

A compound represented by formula (II-6R) was produced in the same manner as in Example 18 except that the compound represented by formula (I-5) was replaced with the compound represented by formula (I-5R).

(Example 19) Production of Compound Represented by Formula (II-7) Using Compound Represented by Formula (I-11) and Produced by Production Method of Invention

[Chem. 92]

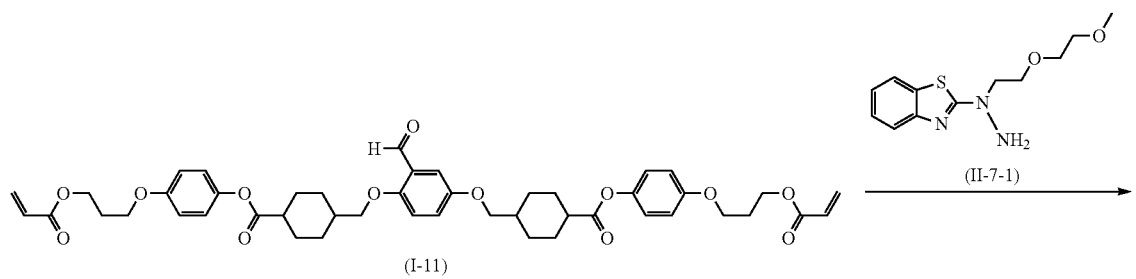

-continued

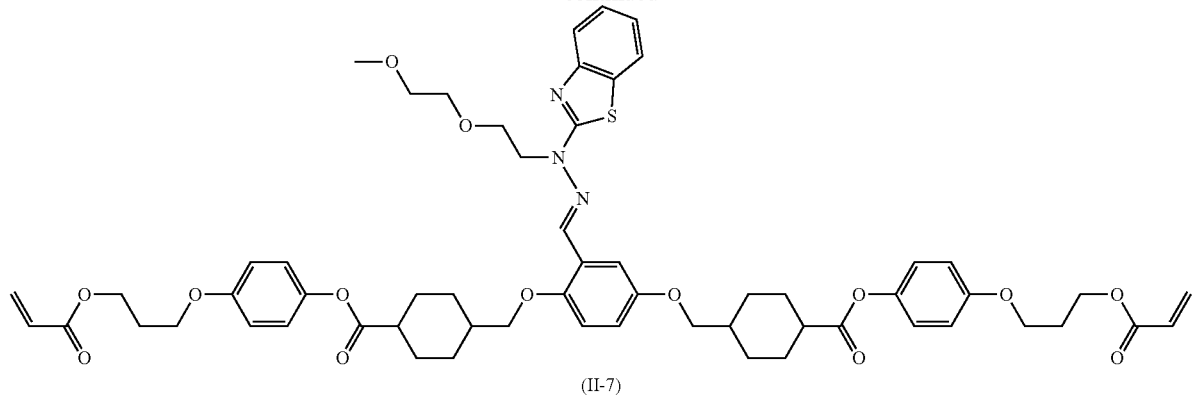

(II-7)

A reaction vessel was charged with 3.0 g of the compound represented by formula (I-11), 0.97 g of a compound represented by formula (II-7-1), 0.25 g of (±)-10-camphorsulfonic acid, 30 mL of tetrahydrofuran, and 5 mL of ethanol in a nitrogen atmosphere, and the mixture was heated to 50° C. and stirred for 6 hours. The solvent was removed by evaporation, and the solid obtained was dispersed in methanol and washed. The product was purified by column chromatography (silica gel, dichloromethane) and recrystallization (dichloromethane/methanol) to thereby obtain 3.1 g of a compound represented by formula (II-7).

Transition temperature (temperature rise: 5° C./minute): C 89-95 N 145 I $^1$H NMR (CDCl$_3$) δ 1.24 (m, 4H), 1.65 (m, 4H), 1.91 (m, 2H), 2.05-2.25 (m, 12H), 2.55 (m, 2H), 3.30 (s, 3H), 3.51 (m, 2H), 3.67 (m, 2H), 3.84-3.89 (m, 6H), 4.05 (t, 4H), 4.36 (t, 4H), 4.54 (t, 2H), 5.84 (dd, 2H), 6.13 (dd, 2H), 6.41 (dd, 2H), 6.84-6.89 (m, 6H), 6.97-7.00 (m, 4H), 7.14 (t, 1H), 7.33 (t, 1H), 7.52 (d, 1H), 7.67 (dd, 2H), 8.34 (s, 1H) ppm.

LC-MS: 1076 [M+1]

(Comparative Example 19) Production of Compound Represented by Formula (II-7R) Using Compound Represented by Formula (I-11R) and Produced by Known Production Method

[Chem. 93]
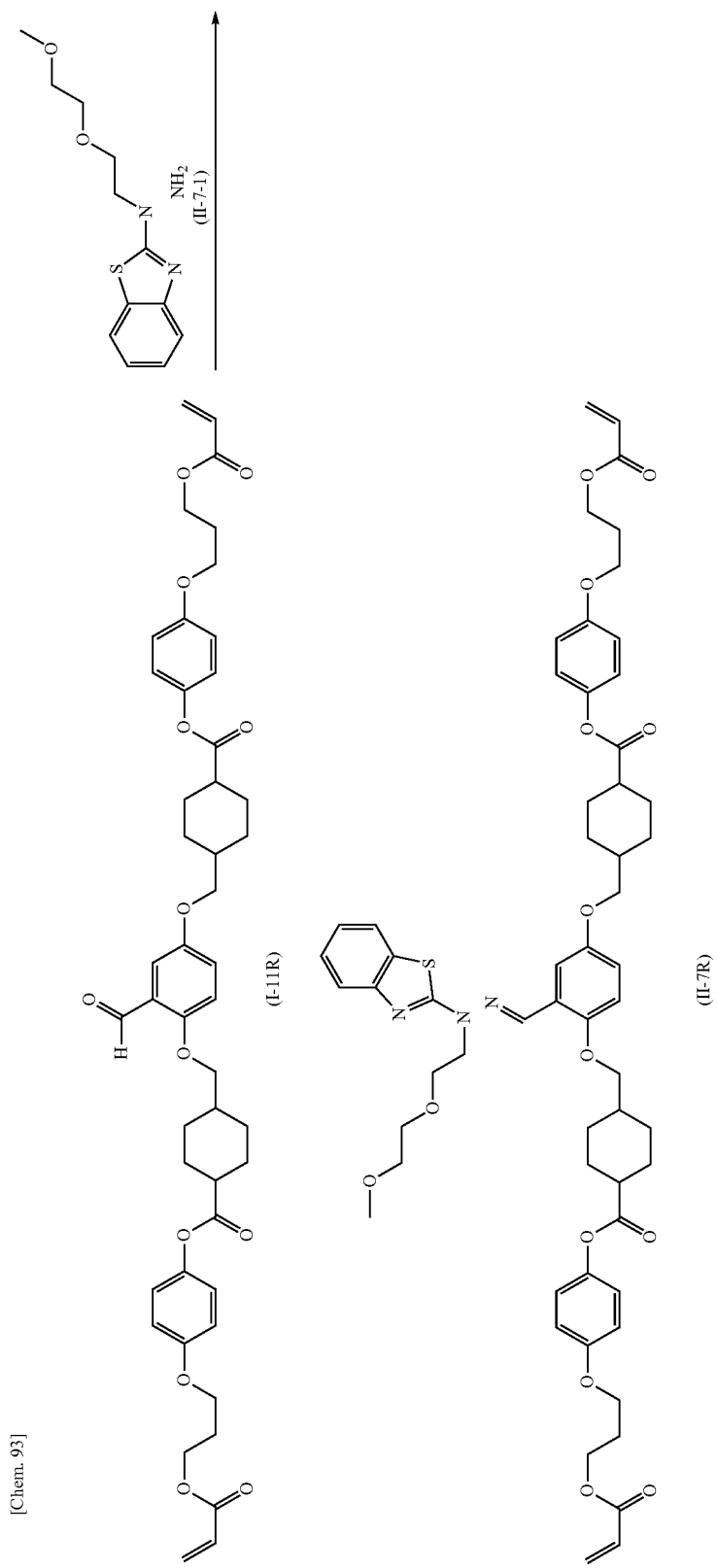

A compound represented by formula (II-7R) was produced in the same manner as in Example 19 except that the compound represented by formula (I-11) was replaced with the compound represented by formula (I-11R).

(Example 20) Production of Compound Represented by Formula (II-8) Using Compound Represented by Formula (I-5) and Produced by Production Method of Invention

[Chem. 94]

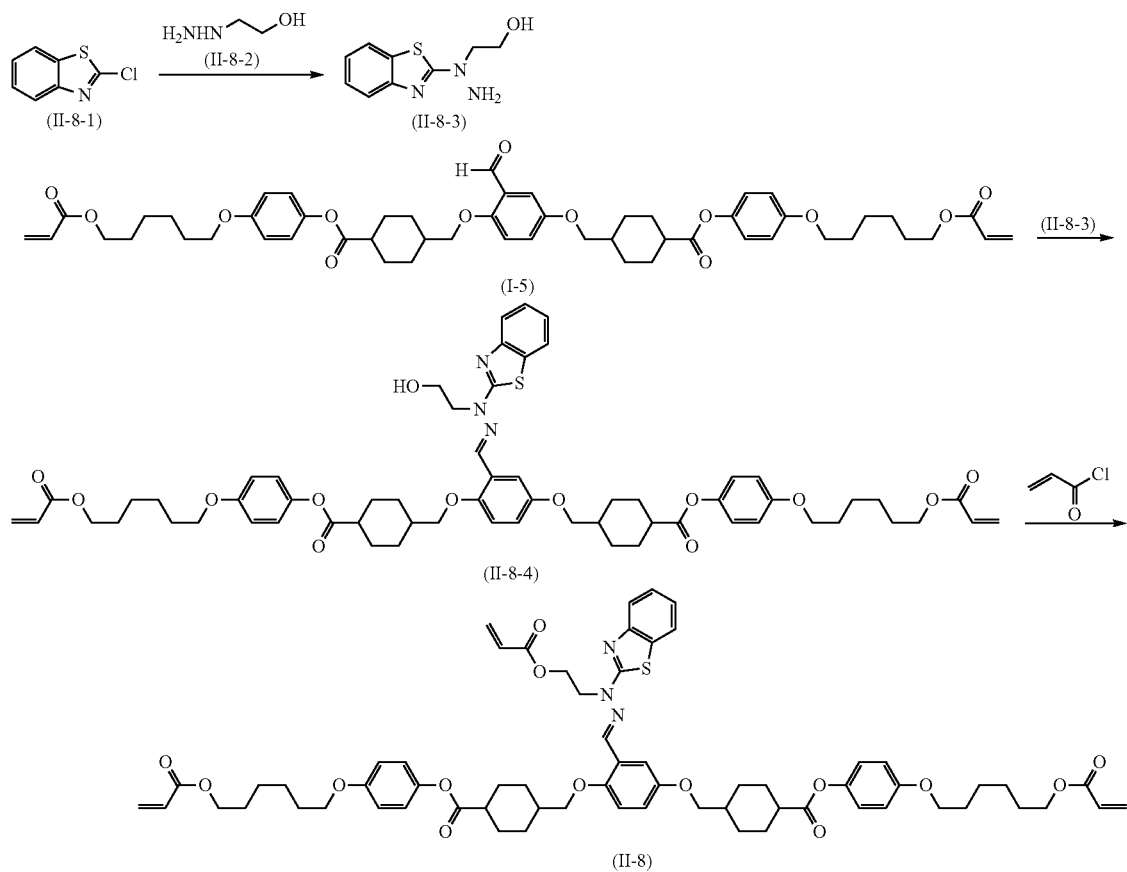

A reaction vessel was charged with 5.0 g of a compound represented by formula (II-8-1), 4.5 g of triethylamine, and 30 mL of dimethoxyethane in a nitrogen atmosphere. While the mixture was heated to 50° C., a solution prepared by dissolving 2.5 g of compound represented by formula (II-8-2) in 5 mL of dimethoxyethane was added dropwise, and the resulting mixture was stirred for 5 hours under heating. The resulting mixture was diluted with dichloromethane and washed with water and then brine. The solvent was removed by evaporation, and the product was dispersed in hexane and washed to thereby obtain 4.3 g of a compound represented by formula (II-8-3).

A reaction vessel was charged with 3.0 g of the compound represented by formula (I-5), 0.69 g of the compound represented by formula (II-8-3), 0.23 g of (±)-10-camphorsulfonic acid, 30 mL of tetrahydrofuran, and 5 mL of ethanol in a nitrogen atmosphere, and the mixture was heated to 50° C. and stirred for 6 hours. The solvent was removed by evaporation, and the solid obtained was dispersed in methanol and washed. The product was purified by column chromatography (silica gel, dichloromethane) and recrystallization (dichloromethane/methanol) to thereby obtain 2.9 g of a compound represented by formula (II-8-4).

A reaction vessel was charged with 2.9 g of the compound represented by formula (II-8-4), 0.41 g of diisopropylethylamine, and 30 mL of dichloromethane in a nitrogen atmosphere. While the reaction vessel was cooled with ice, 0.26 g of acryloyl chloride was added dropwise, and the mixture was stirred at room temperature for 5 hours. The resulting mixture was washed with 1% hydrochloric acid, then water, and brine. The product was purified by column chromatography (silica gel, dichloromethane) and recrystallization (dichloromethane/methanol) to thereby obtain 2.3 g of a compound represented by formula (II-8).

Transition temperature (temperature rise rate: 5° C./minute) C 122 N 142 I $^1$H NMR (CDCl$_3$) δ 1.24 (m, 4H), 1.48 (m, 8H), 1.60-1.83 (m, 12H), 1.93 (m, 2H), 2.08 (t, 4H), 2.23 (m, 4H), 2.54 (m, 2H), 3.86 (dd, 4H), 3.94 (t, 4H), 4.17 (t, 4H), 4.53 (t, 2H), 4.65 (t, 2H), 5.78 (dd, 1H), 5.82 (dd, 2H), 6.08 (dd, 1H), 6.12 (dd, 2H), 6.39 (dd, 1H), 6.40 (dd, 2H), 6.88 (m, 6H), 6.97 (dd, 4H), 7.16 (t, 1H), 7.34 (t, 1H), 7.54 (d, 1H), 7.66 (d, 1H), 7.70 (d, 1H), 8.36 (s, 1H) ppm.

LC-MS: 1156 [M+1]

(Comparative Example 20) Production of Compound Represented by Formula (II-8R) Using Compound Represented by Formula (I-5R) and Produced by Known Production Method

[Chem. 95]
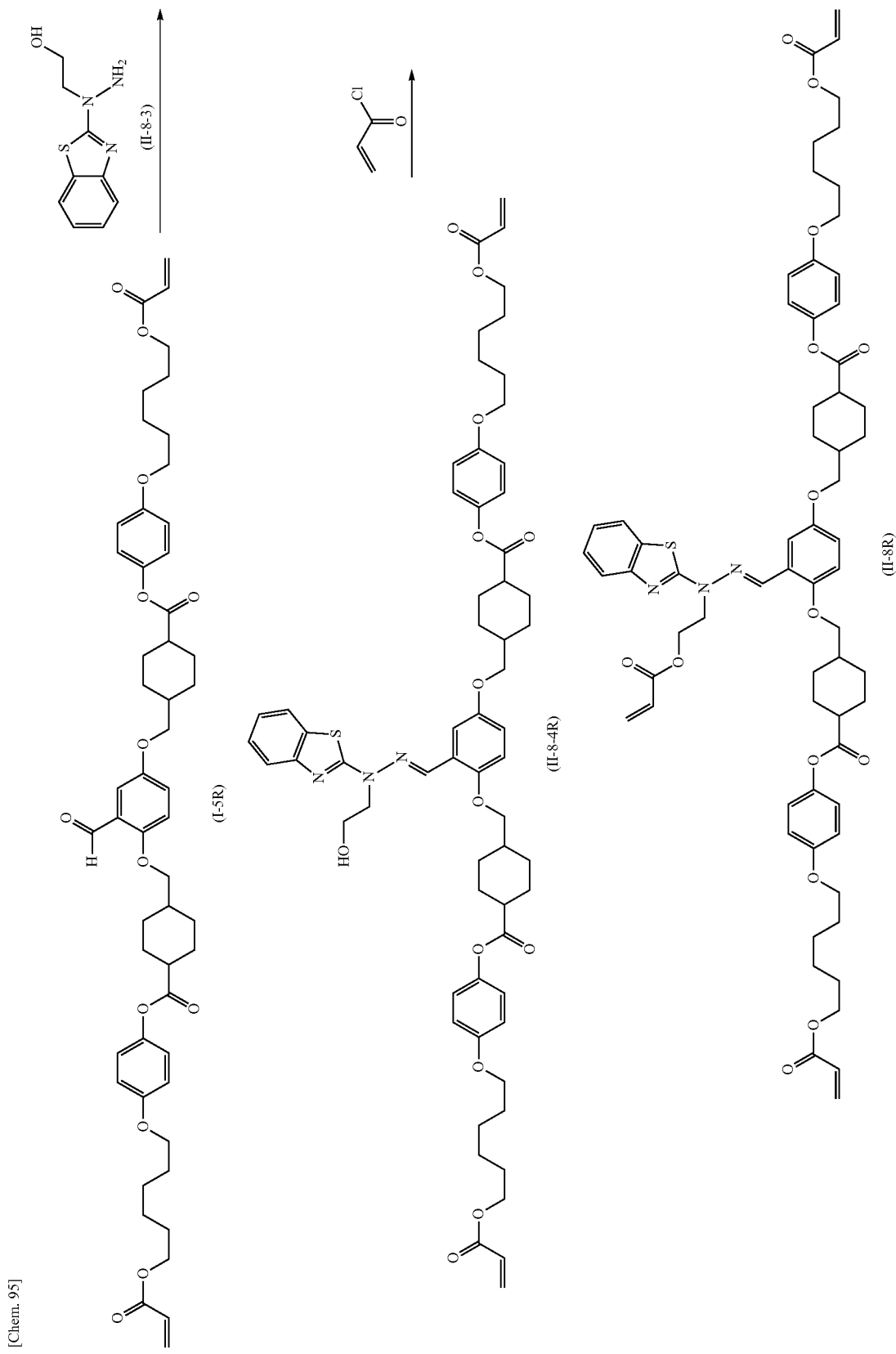

A compound represented by formula (II-8R) was produced in the same manner as in Example 20 except that the compound represented by formula (I-5) was replaced with the compound represented by formula (I-5R).

(Example 21) Production of Compound Represented by Formula (II-9) Using Compound Represented by Formula (I-5) and Produced by Production Method of Invention

[Chem. 96]
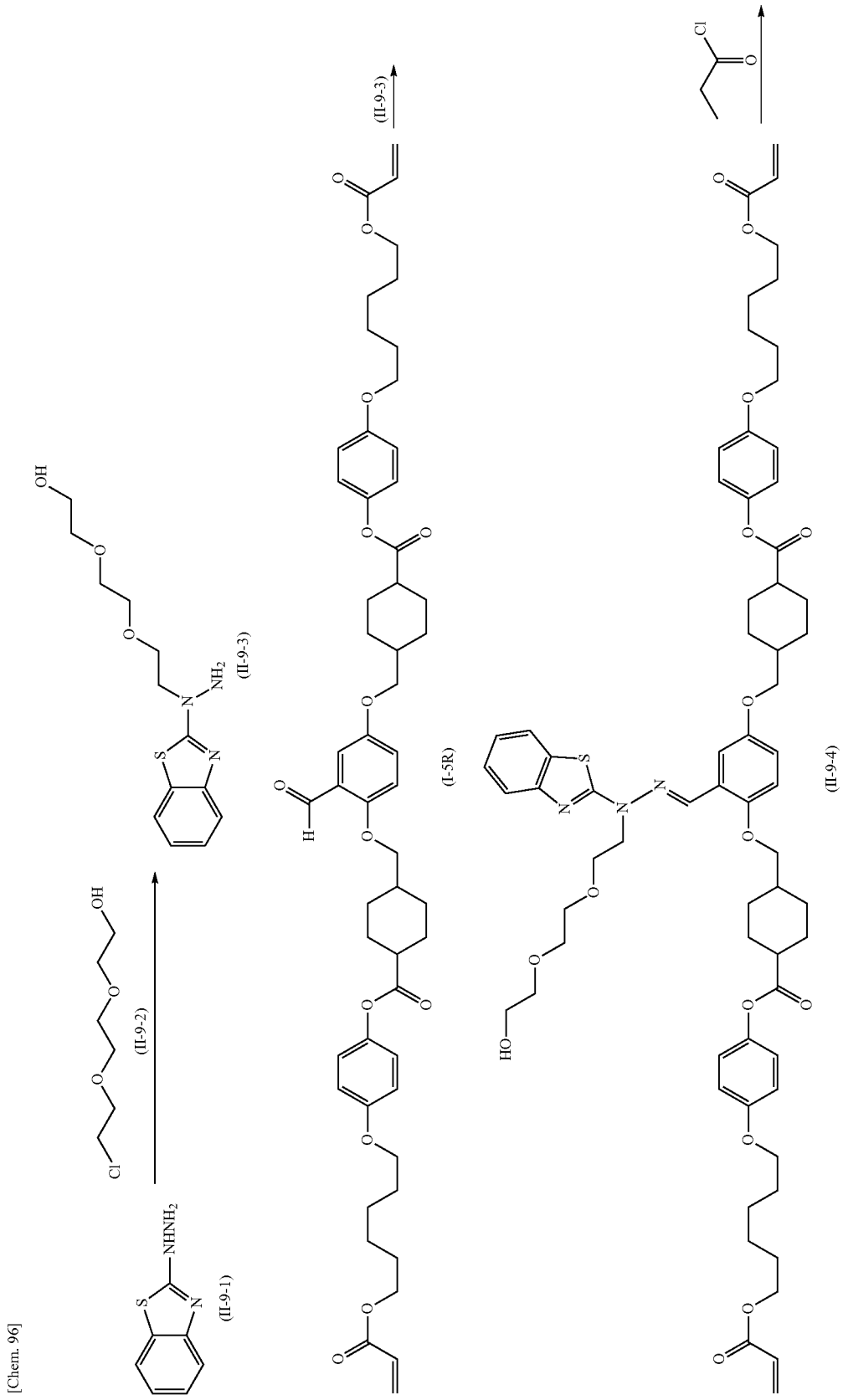

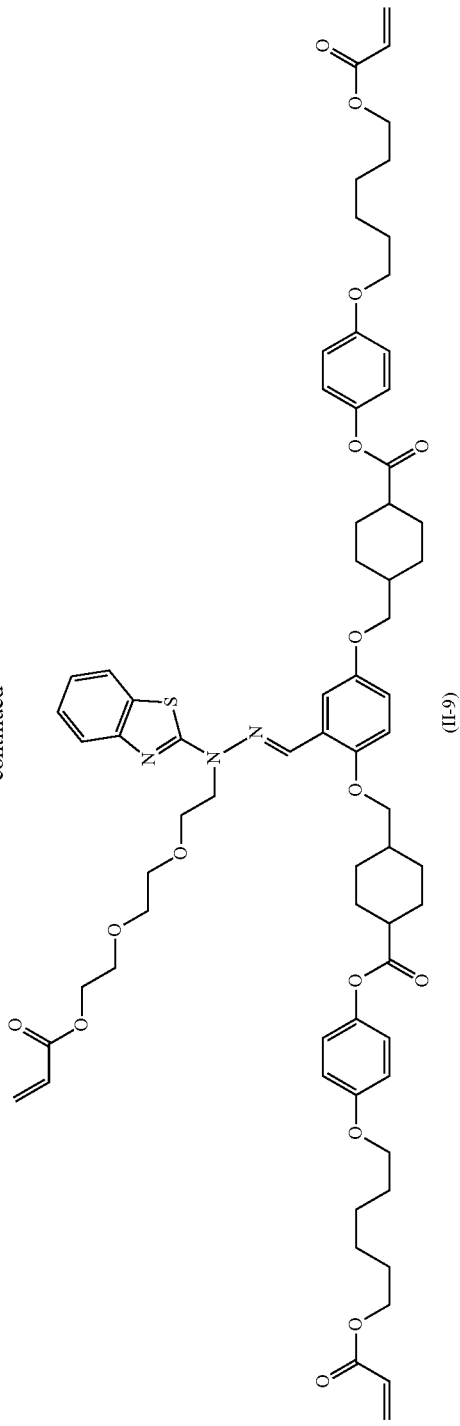

A reaction vessel was charged with 5.0 g of a compound represented by formula (II-9-1) and 25 mL of tetrahydrofuran in a nitrogen atmosphere. Then 6.8 g of potassium tert-butoxide was added, and the mixture was stirred at room temperature for 2 hours. A solution prepared by dissolving 5.6 g of a compound represented by formula (II-9-2) in 6 mL of tetrahydrofuran was added dropwise, and the mixture was stirred at room temperature for 8 hours. The resulting mixture was diluted with dichloromethane and washed with water and then brine. The product was purified by column chromatography (alumina, dichloromethane) to thereby obtain 6.3 g of a compound represented by formula (II-9-3).

A reaction vessel was charged with 3.0 g of the compound represented by formula (I-5), 0.98 g of the compound represented by formula (II-9-3), 0.23 g of (±)-10-camphorsulfonic acid, 30 mL of tetrahydrofuran, and 5 mL of ethanol in a nitrogen atmosphere, and the mixture was heated to 50° C. and stirred for 6 hours. The solvent was removed by evaporation, and the solid obtained was dispersed in methanol and washed. The product was purified by column chromatography (silica gel, dichloromethane) and recrystallization (dichloromethane/methanol) to thereby obtain 2.7 g of a compound represented by formula (II-9-4).

A reaction vessel was charged with 2.7 g of the compound represented by formula (II-9-4), 0.36 g of diisopropylethylamine, and 30 mL of dichloromethane in a nitrogen atmosphere. While the reaction vessel was cooled with ice, 0.23 g of acryloyl chloride was added dropwise, and the mixture was stirred at room temperature for 5 hours. The resulting mixture was washed with 1% hydrochloric acid, then water, and brine. The product was purified by column chromatography (silica gel, dichloromethane) and recrystallization (dichloromethane/methanol) to thereby obtain 2.0 g of a compound represented by formula (II-9).

Transition temperature (temperature rise: 5° C./minute) C 71 N 115 I $^1$H NMR (CDCl$_3$) δ 1.19-1.29 (m, 4H), 1.41-1.82 (m, 22H), 1.91 (m, 2H), 2.08 (m, 4H), 2.24 (m, 4H), 2.53 (m, 2H), 3.62 (m, 3H), 3.67 (m, 2H), 3.84-3.90 (m, 5H), 3.94 (t, 4H), 4.15-4.19 (m, 6H), 4.53 (t, 2H), 5.76 (dd, 1H), 5.82 (dd, 2H), 6.08 (dd, 1H), 6.12 (dd, 2H), 6.37 (dd, 1H), 6.40 (dd, 2H), 6.84-6.90 (m, 6H), 6.95-6.98 (m, 4H), 7.14 (t, 1H), 7.32 (t, 1H), 7.53 (d, 1H), 7.65 (d, 1H), 7.69 (d, 1H), 8.34 (s, 1H) ppm.

LC-MS: 1244 [M+1]

(Comparative Example 21) Production of Compound Represented by Formula (II-9R) Using Compound Represented by Formula (I-5R) and Produced by Known Production Method

[Chem. 97]
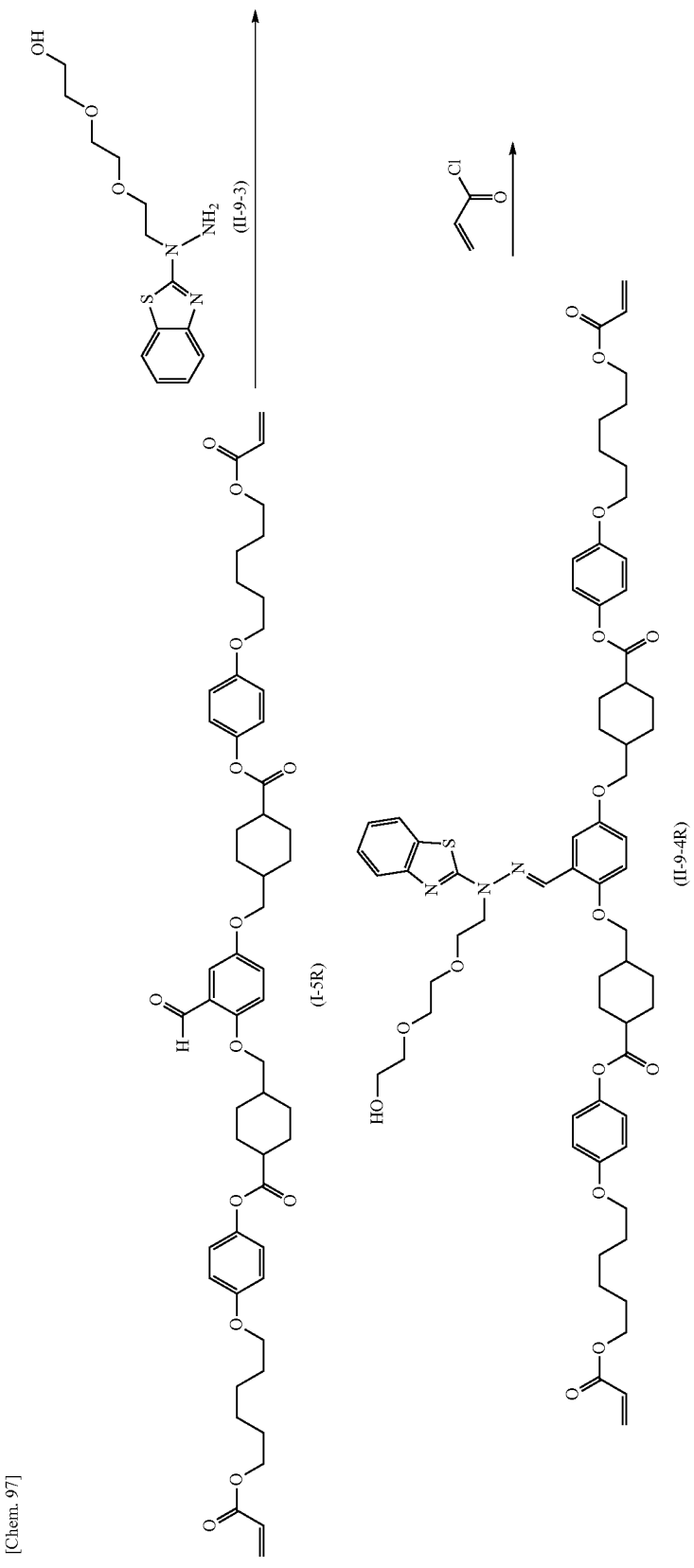

-continued
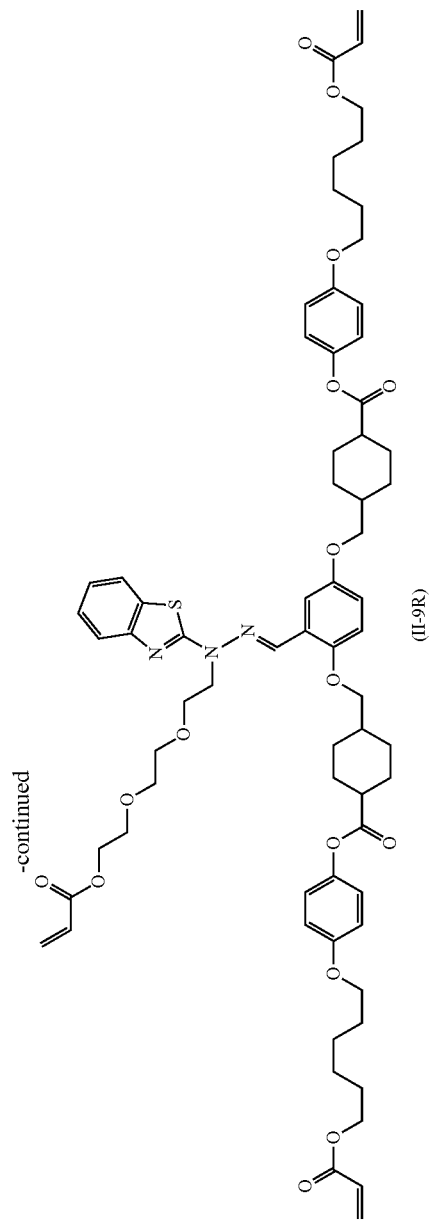
(II-9R)

A compound represented by formula (II-9R) was produced in the same manner as in Example 21 except that the compound represented by formula (I-5) was replaced with the compound represented by formula (I-5R).

Ester group-containing compounds were produced using the methods described in the above Examples, and compounds represented by the following formula (II-10) to formula (II-29) were produced from the ester group-containing compounds using known methods.

[Chem. 98]

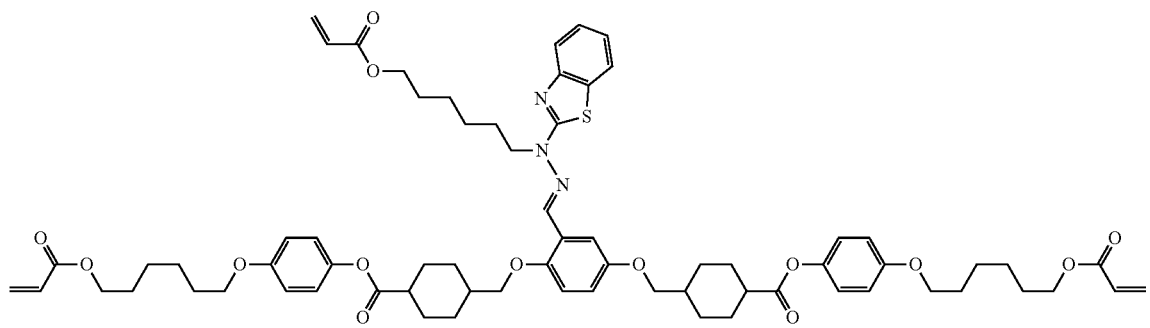

(II-10)

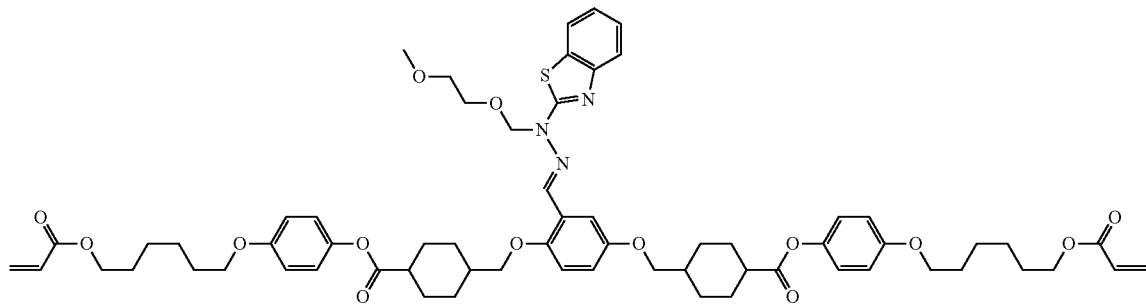

(II-11)

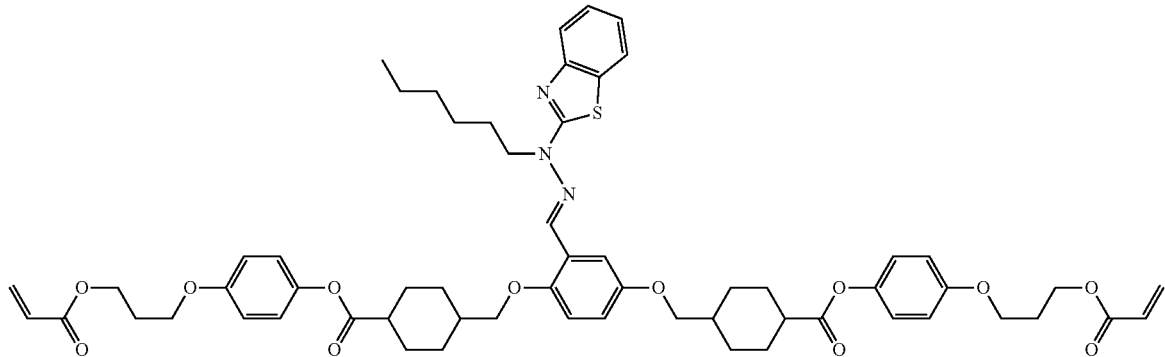

(II-12)

-continued
(II-13)
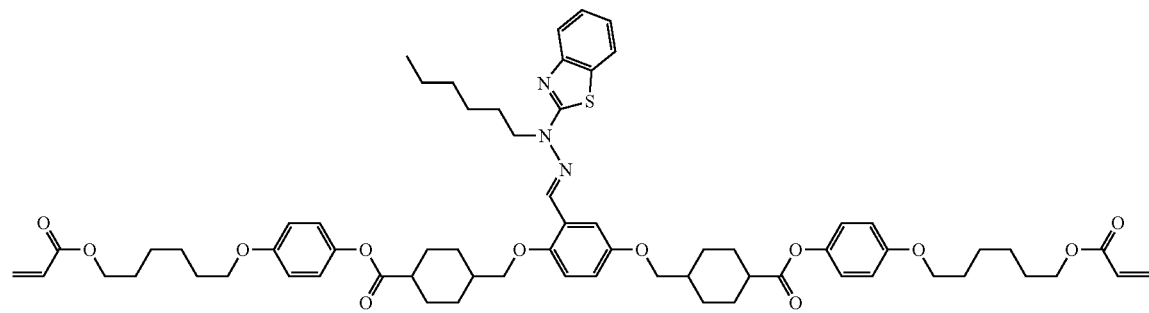
(II-14)
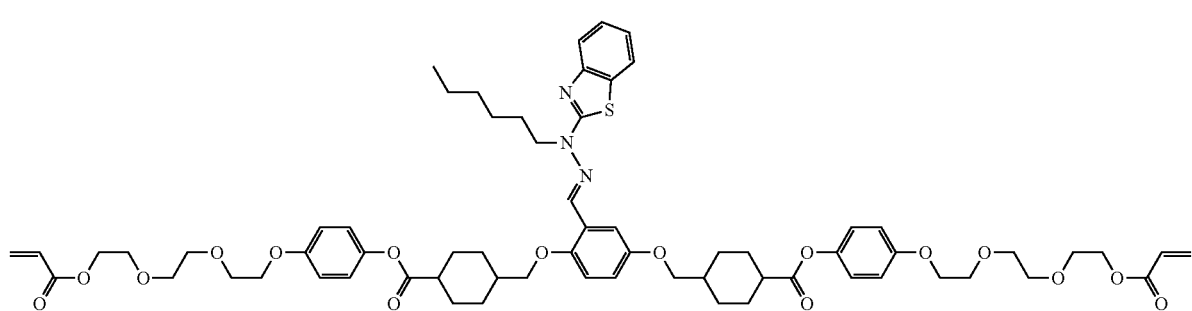
[Chem. 99]
(II-15)
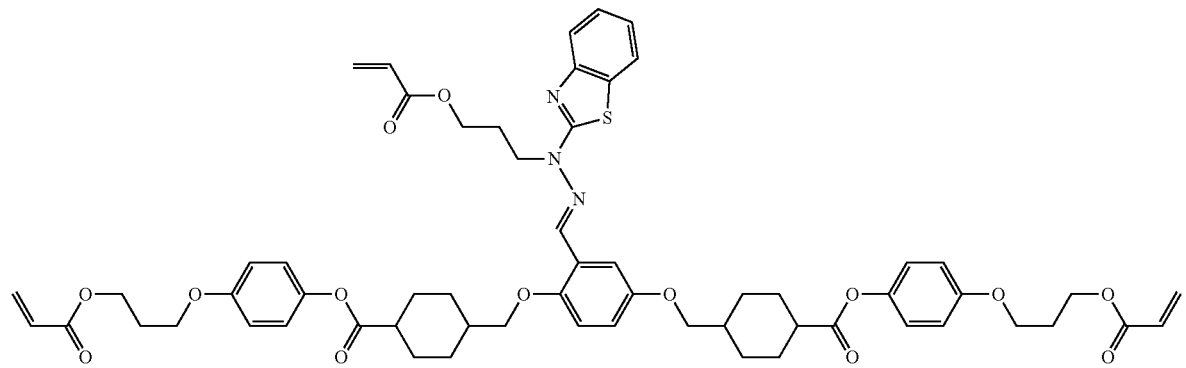
(II-16)
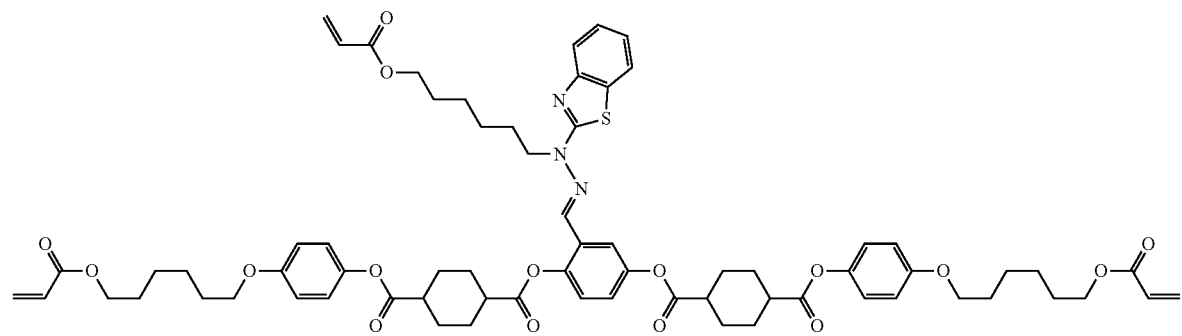

-continued
(II-17)
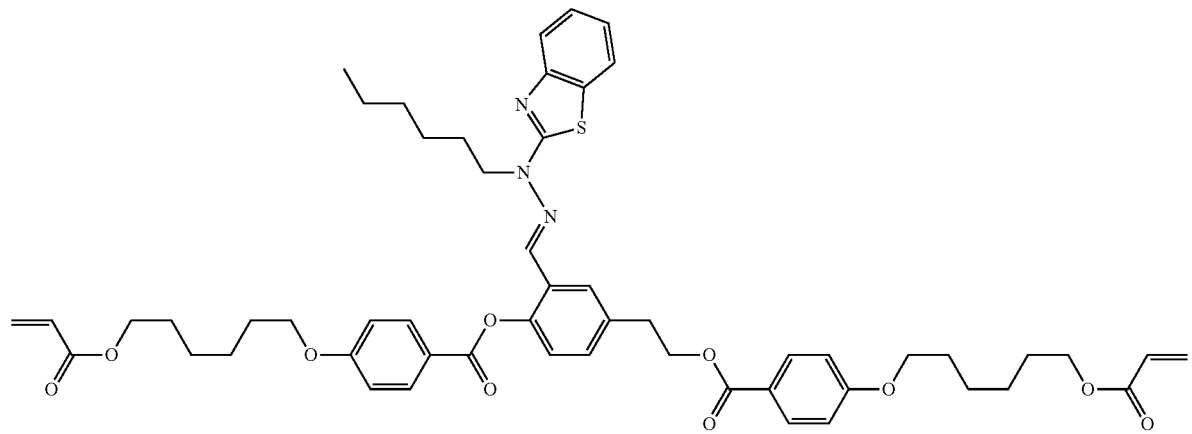
(II-18)
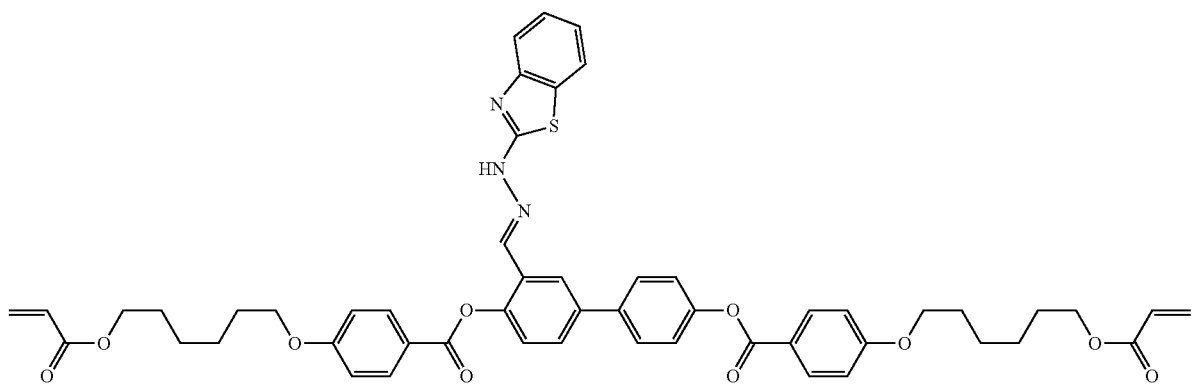
(II-19)
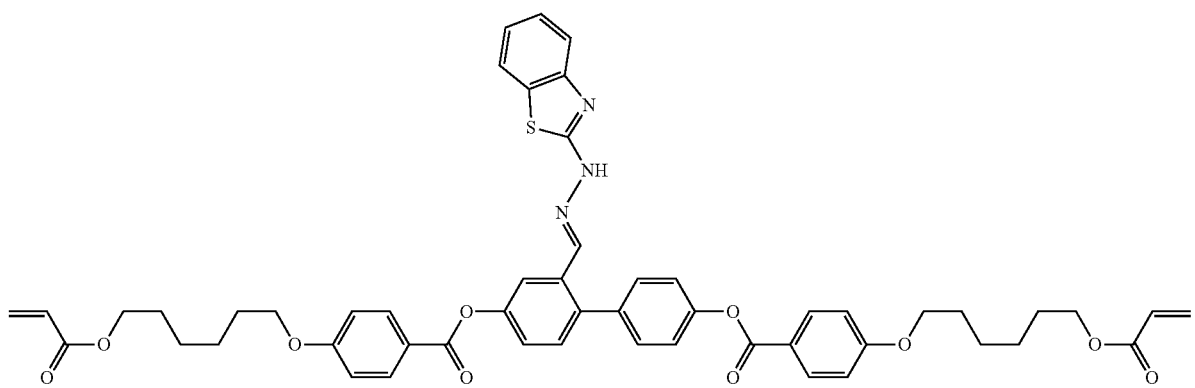

[Chem. 100]
(II-20)
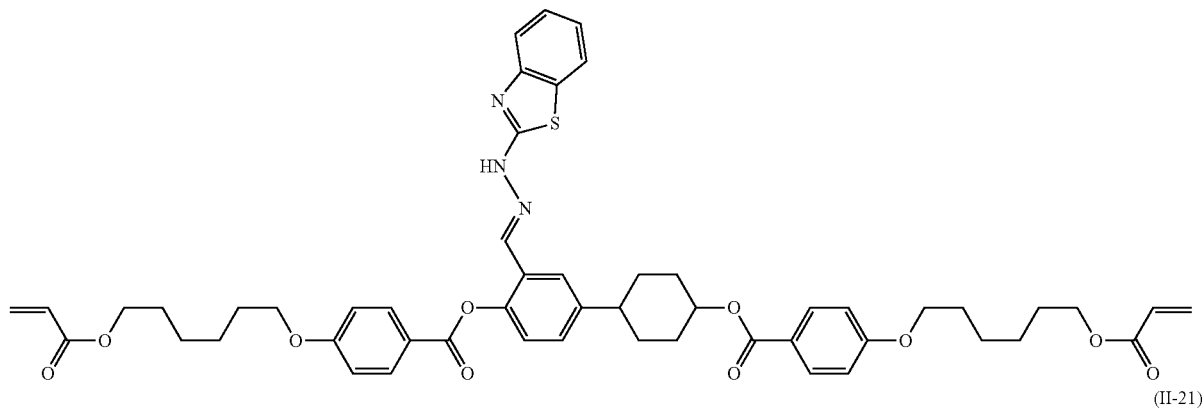
(II-21)
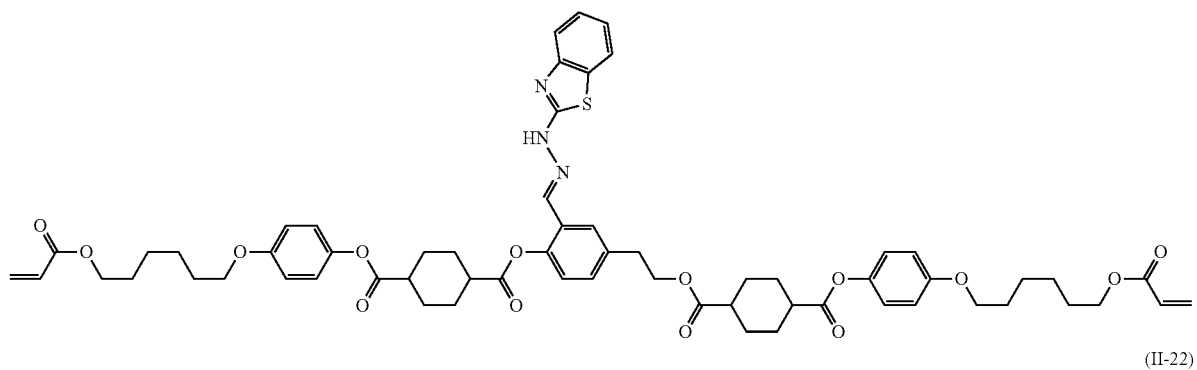
(II-22)
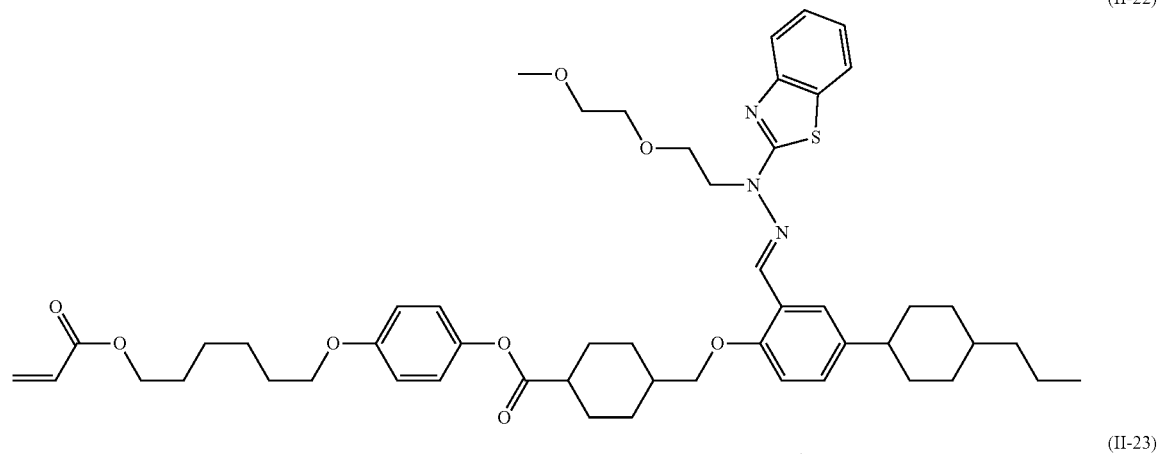
(II-23)
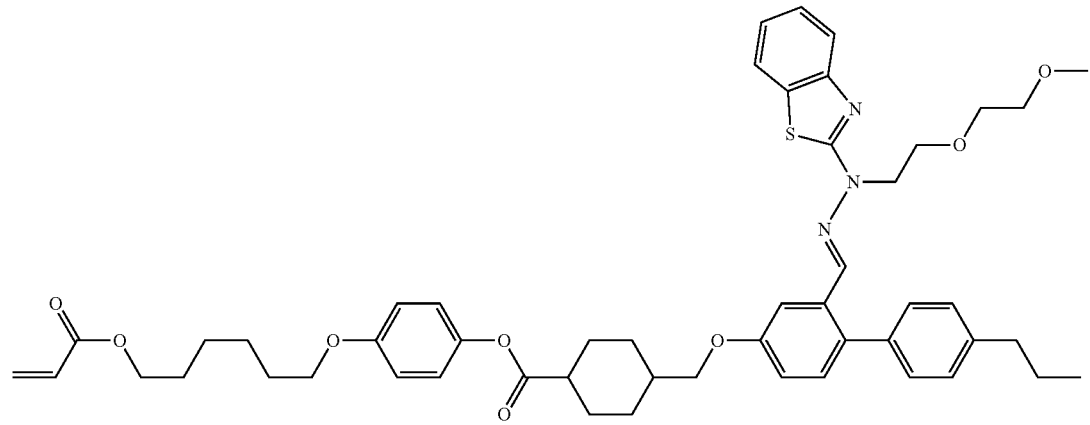

(II-24)
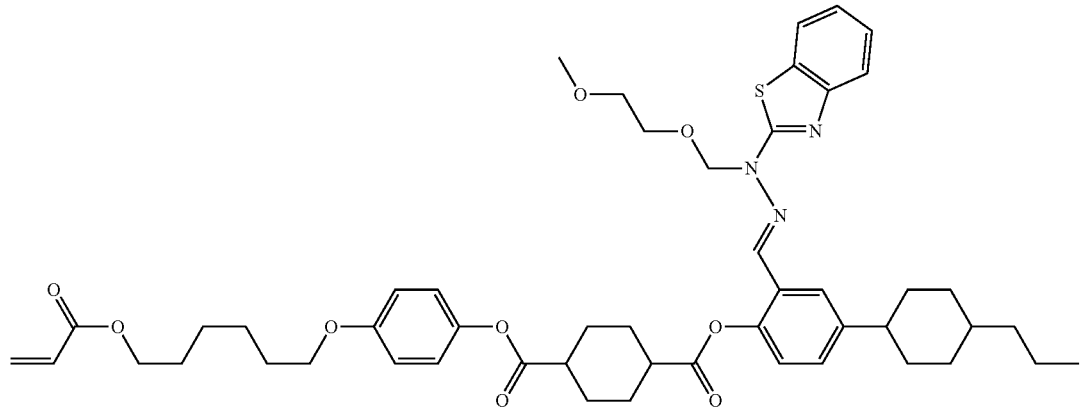
(II-25)
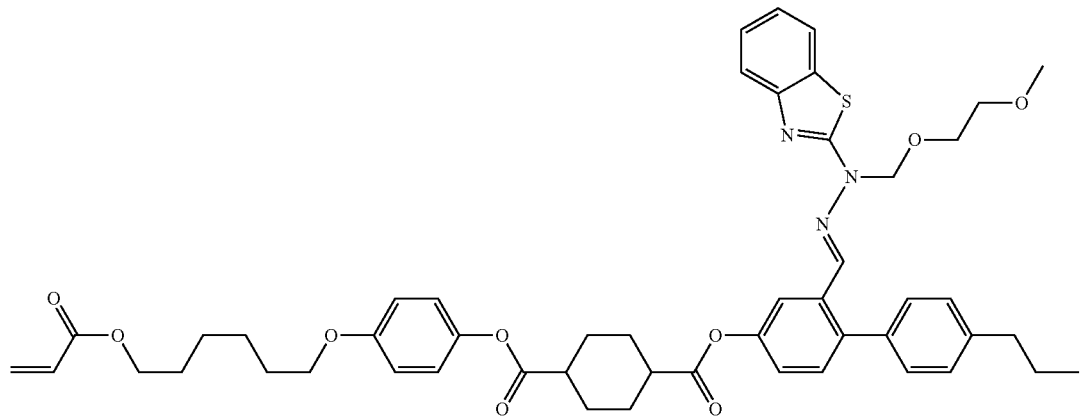
(II-26)
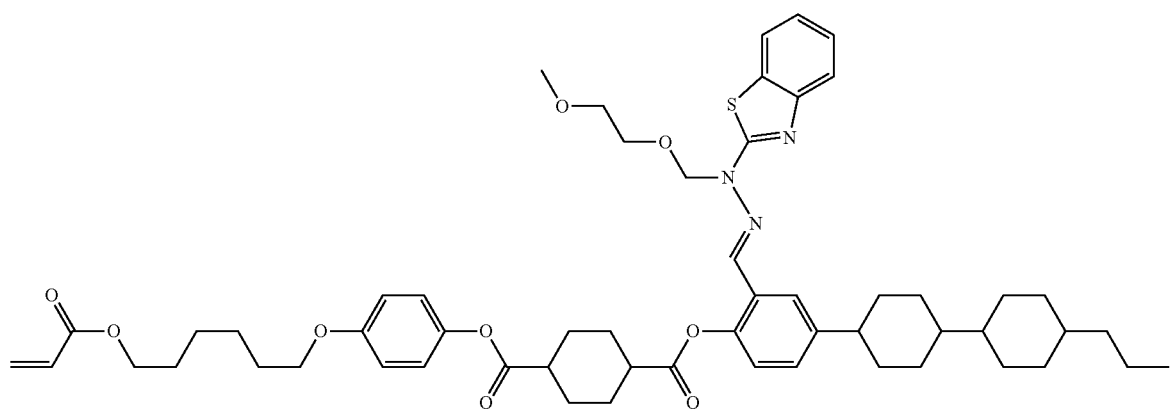

-continued

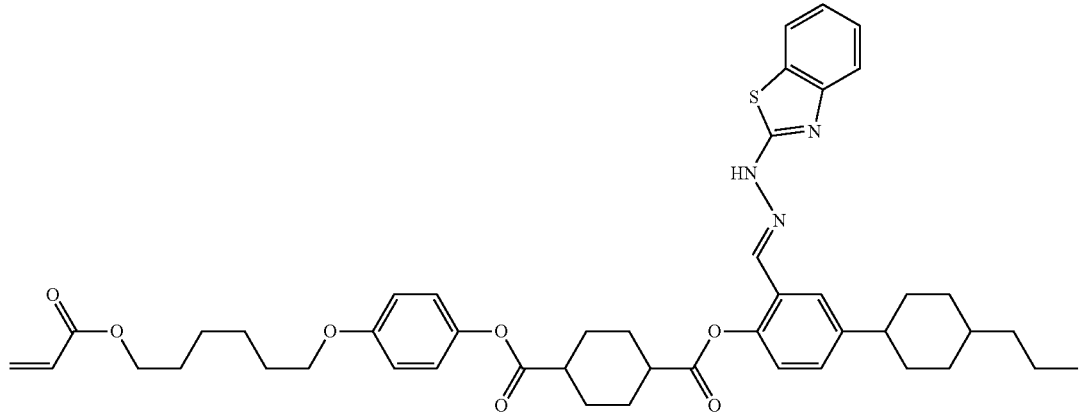
(II-27)

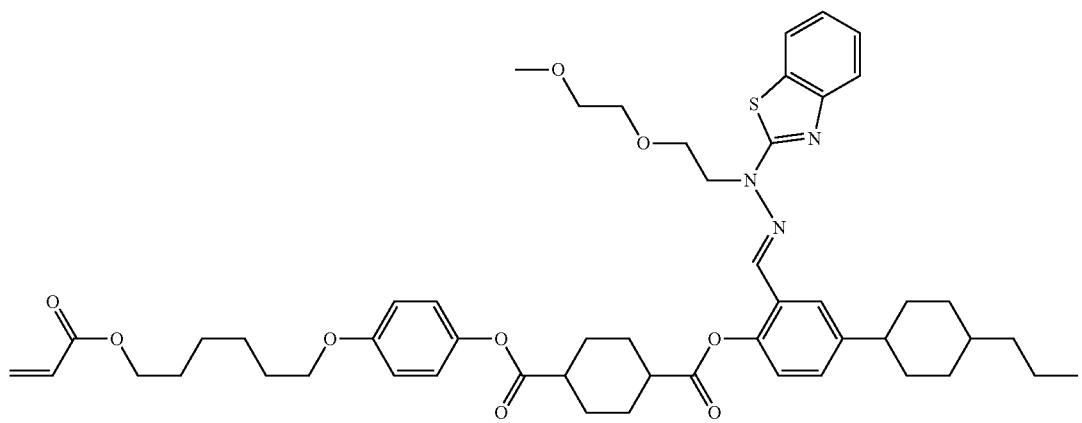
(II-28)

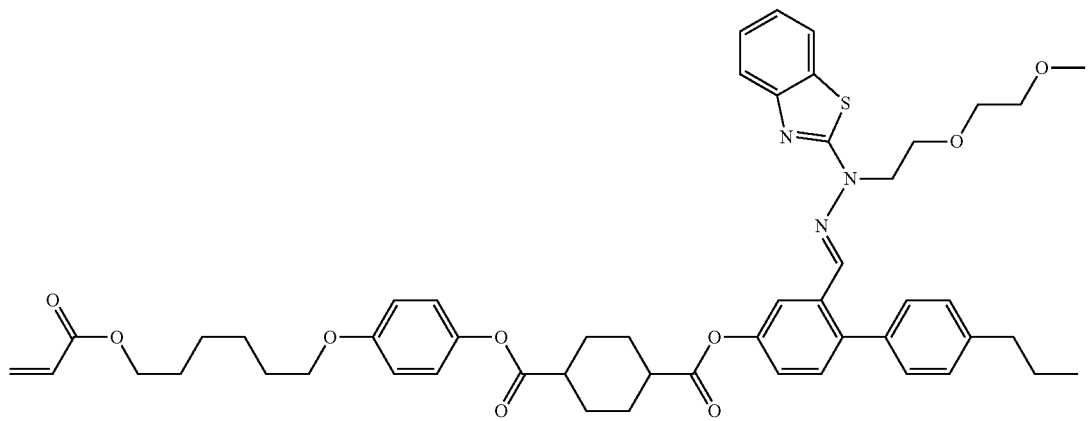
(II-29)

Examples 22 to 32 and Comparative Examples 22 to 32

The compounds represented by formula (I-2), formula (I-6), and formula (II-1) to formula (II-9) described in the above Examples and the compounds represented by formula (I-2R), formula (I-6R), and formulas (II-1R) to formula (II-9R) were used as compounds for evaluation.

A polyimide solution for an alignment film was applied to a 100×100 mm glass substrate with a thickness of 0.7 mm by spin coating, dried at 100° C. for 10 minutes, and fired at 200° C. for 60 minutes to thereby obtain a coating film. The coating film obtained was subjected to rubbing treatment. A commercial rubbing apparatus was used for the rubbing treatment.

A liquid crystal composition composed of the following known compounds: (X-1): 30%, (X-2): 30%, and (X-3): 40% was used as a host liquid crystal (X).

[Chem. 102]

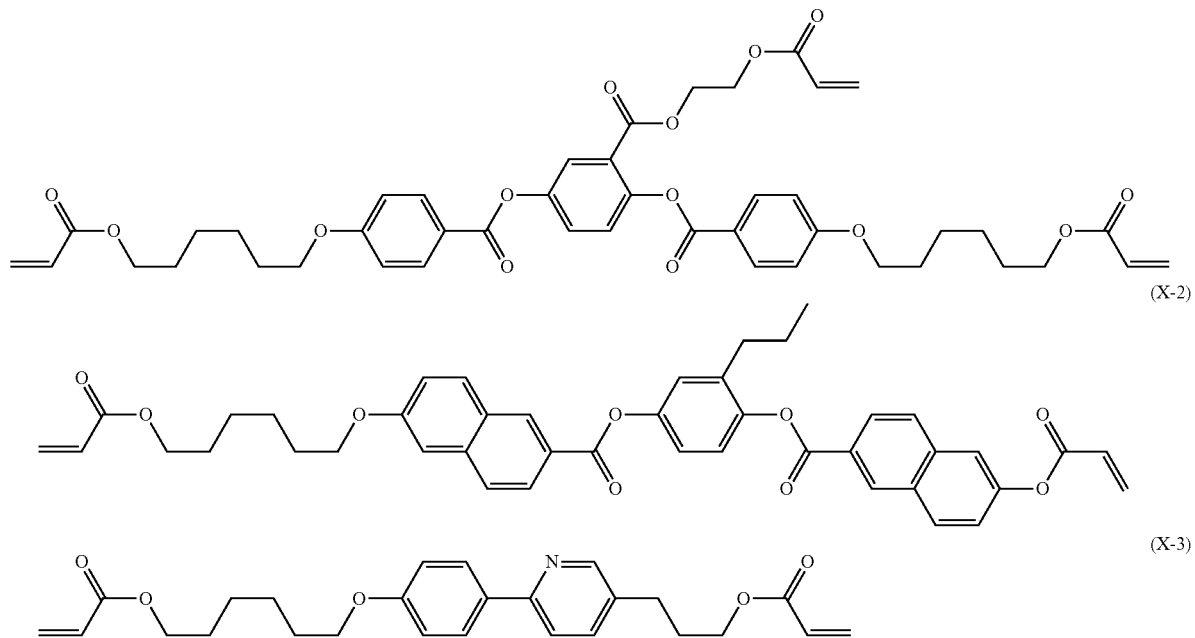

A composition containing the host liquid crystal (X) and 20% of one of the compounds for evaluation was prepared. 1% of a photopolymerization initiator Irgacure 907 (manufactured by BASF), 0.1% of 4-methoxyphenol, and 80% of chloroform were added to the composition to prepare a coating solution. The coating solution was applied to the rubbed glass substrate by spin coating, dried at 80° C. for 1 minute, and then dried at 120° C. for 1 minute. Then a high-pressure mercury lamp was used to irradiate the resulting glass substrate with ultraviolet rays at an intensity of 40 mW/cm² for 25 seconds to prepare a film for evaluation. The correspondence between the film for evaluation and the compound for evaluation used is shown in the following tables.

TABLE 1

| Film for evaluation | Compound for evaluation |
| --- | --- |
| Example 22 | Inventive compound (I-2) |
| Example 23 | Inventive compound (I-6) |
| Example 24 | Inventive compound (II-1) |
| Example 25 | Inventive compound (II-2) |
| Example 26 | Inventive compound (II-3) |
| Example 27 | Inventive compound (II-4) |
| Example 28 | Inventive compound (II-5) |
| Example 29 | Inventive compound (II-6) |
| Example 30 | Inventive compound (II-7) |
| Example 31 | Inventive compound (II-8) |
| Example 32 | Inventive compound (II-9) |

TABLE 2

| Film for evaluation | Compound for evaluation |
| --- | --- |
| Comparative Example 22 | Comparative compound (I-2R) |
| Comparative Example 23 | Comparative compound (I-6R) |
| Comparative Example 24 | Comparative compound (II-1R) |

TABLE 2-continued

| Film for evaluation | Compound for evaluation |
| --- | --- |
| Comparative Example 25 | Comparative compound (II-2R) |
| Comparative Example 26 | Comparative compound (II-3R) |
| Comparative Example 27 | Comparative compound (II-4R) |
| Comparative Example 28 | Comparative compound (II-5R) |
| Comparative Example 29 | Comparative compound (II-6R) |
| Comparative Example 30 | Comparative compound (II-7R) |
| Comparative Example 31 | Comparative compound (II-8R) |
| Comparative Example 32 | Comparative compound (II-9R) |

Each of the films for evaluation obtained was subjected to heat treatment at 90° C. for 200 hours. Then a xenon lamp irradiation tester (SUNTEST XLS manufactured by ATLAS) was used to perform a sun-test at 60 mW/cm², 28° C., and 120 J. After the sun test, the film was divided into a 10×10 vertical-horizontal grid, i.e., hundred 10 mm-square regions, and polarizing microscope observation was performed to count the number of regions in which deterioration such as uneven alignment, discoloration, or partial or full delamination was found. The ratio (%) of the number of regions with deterioration is shown in the following tables.

TABLE 3

| Film for evaluation | Ratio of number of regions with deterioration |
| --- | --- |
| Example 22 | 2% |
| Example 23 | 0% |
| Example 24 | 2% |
| Example 25 | 3% |
| Example 26 | 1% |
| Example 27 | 1% |
| Example 28 | 1% |
| Example 29 | 0% |
| Example 30 | 0% |

TABLE 3-continued

| Film for evaluation | Ratio of number of regions with deterioration |
|---|---|
| Example 31 | 0% |
| Example 32 | 0% |

TABLE 4

| Film for evaluation | Ratio of number of regions with deterioration |
|---|---|
| Comparative Example 22 | 8% |
| Comparative Example 23 | 4% |
| Comparative Example 24 | 7% |
| Comparative Example 25 | 7% |
| Comparative Example 26 | 8% |
| Comparative Example 27 | 12% |
| Comparative Example 28 | 8% |
| Comparative Example 29 | 13% |
| Comparative Example 30 | 12% |
| Comparative Example 31 | 8% |
| Comparative Example 32 | 7% |

As can be seen from the tables, the deterioration ratio is smaller in the films using the compounds represented by formula (I-2), formula (I-6), and formula (II-1) to formula (II-9) and produced by the production method of the present invention than in the films using the compounds represented by formula (I-2R), formula (I-6R), and formula (II-1R) to formula (II-9R) and produced by the known production methods. This shows that high heat resistance and high lightfastness can be obtained by the production method of the present invention. Therefore, the compounds produced by the production method of the present invention are useful as components of polymerizable compositions. An optically anisotropic body using a polymerizable liquid crystal composition containing a compound produced by the production method of the present invention is useful for optical film applications etc.

The invention claimed is:

1. A method for producing a derivative of an ester group-containing compound, the method comprising:
a first production step of mixing a condensing agent, a Bronsted acid, a carboxylic acid represented by formula (I-5-8), and a phenol or an alcohol represented by formula (ma2-1) to prepare a reaction mixture and then subjecting the carboxylic acid and the phenol or alcohol to a condensation reaction in the reaction mixture,

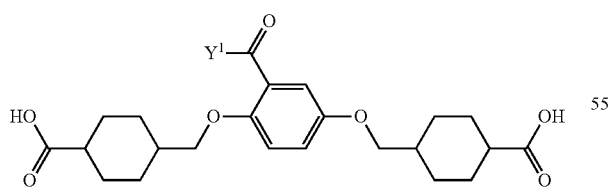
(I-5-8)

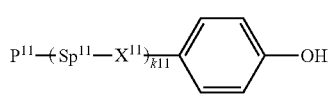
(ma2-1)

wherein the Bronsted acid is other than the condensing agent, the carboxylic acid, and the phenol, wherein the first production step thereby produces a synthetic intermediate represented by general formula (I-i-1-1-1-1-1):

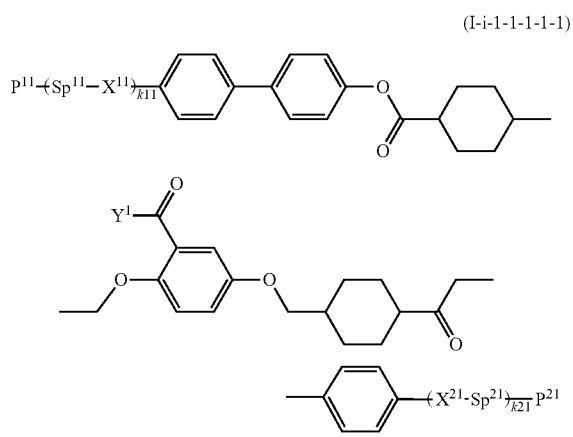
(I-i-1-1-1-1-1)

where in formulae (I-5-8), (ma2-1) and (I-i-1-1-1-1-1), $P^{11}$ and $P^{21}$ each independently represent a group selected from the following formula (P-1) to formula (P-20);

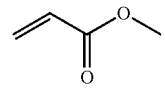
(P-1)

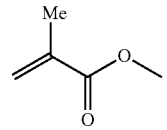
(P-2)

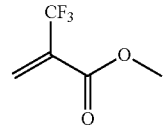
(P-3)

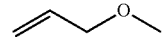
(P-4)

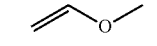
(P-5)

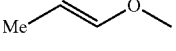
(P-6)

(P-7)

(P-8)

(P-9)

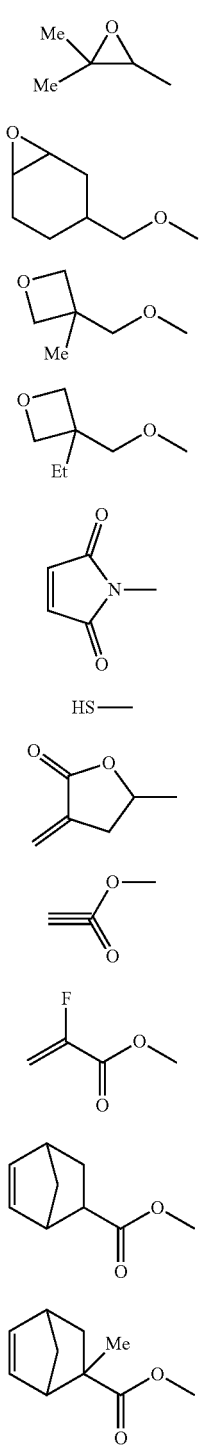

(P-10)
(P-11)
(P-12)
(P-13)
(P-14)
(P-15)
(P-16)
(P-17)
(P-18)
(P-19)
(P-20)

$Sp^{11}$ and $Sp^{21}$ each independently represent a single bond, or an alkylene group which has 1 to 10 carbon atoms and in which one —$CH_2$— group or two or more non-adjacent —$CH_2$— groups are each independently optionally replaced with —O—, —COO— or —OCO—, $X^{11}$ and $X^{21}$ each represent —O—, —$OCH_2$—, —$CH_2O$—, —COO—, —OCO—, —COO—$CH_2CH_2$—, —OCO—$CH_2CH_2$—, —$CH_2CH_2$—COO—, —$CH_2CH_2$—OCO—, or a single bond, k11 and k21 each independently represent an integer of 1, and $Y^1$ represents a hydrogen atom; and a second production step comprising a step of reacting the synthetic intermediate with a compound represented by formula (I-iii-1) or formula (I-iii-2),

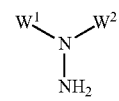

(I-iii-1)

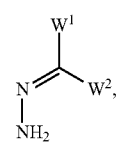

(I-iii-2)

wherein $W^1$ represents a group represented by a formula

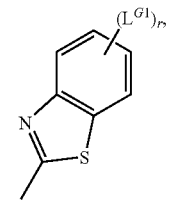

in which $L^{G1}$ represents a fluorine atom, a chlorine atom, a nitro group, a cyano group, a dimethylamino group, a diethylamino group, or a linear alkyl group which has 1 or 2 carbon atoms in which one —$CH_2$— group or two or more non-adjacent —$CH_2$— groups are each independently optionally replaced with —O—, and any hydrogen atom in the alkyl group being optionally replaced with a fluorine atom; r represents an integer from 0 to 4, wherein $W^2$ represents a hydrogen atom or a linear or branched alkyl group which has 1 to 20 carbon atoms and in which one —$CH_2$— group or two or more non-adjacent —$CH_2$— groups are each independently optionally replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom in the alkyl group being optionally replaced with a fluorine atom, wherein the second production step produces a compound represented by general formula (I-ii-1-1-1-2-1):

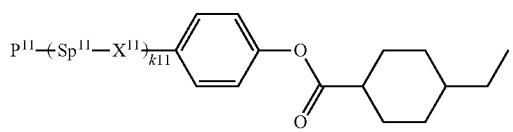

(I-ii-1-1-1-2-1)

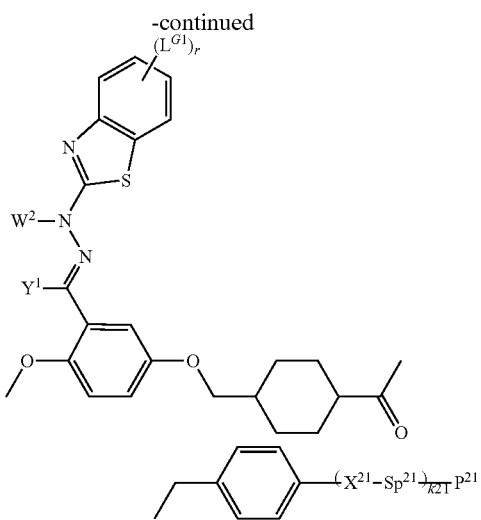

where in formula (I-ii-1-1-1-2-1), $Y^1$, $W^2$, $L^{G1}$, r, $P^{11}$, $P^{21}$, $Sp^{11}$, $Sp^{21}$, $X^{11}$, $X^{21}$, k11, and k21 have the same meanings as in the formula (I-i-1-1-1-1-1), the formula (I-iii-1) or the formula (I-iii-2).

2. The method for producing a derivative of an ester group-containing compound according to claim 1, wherein the synthetic intermediate obtained in the first production step is represented by formula (I-5), (I-5)

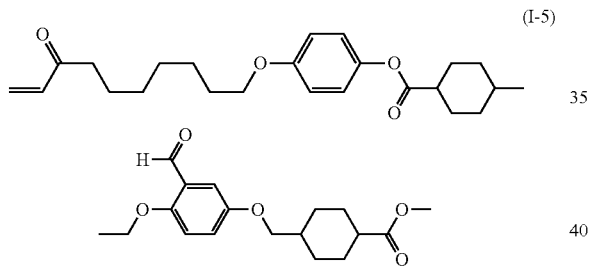

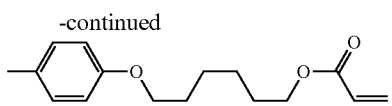

wherein the compound represented by general formula (I-ii) obtained in the second production step is represented by formula (II-9), (II-9)

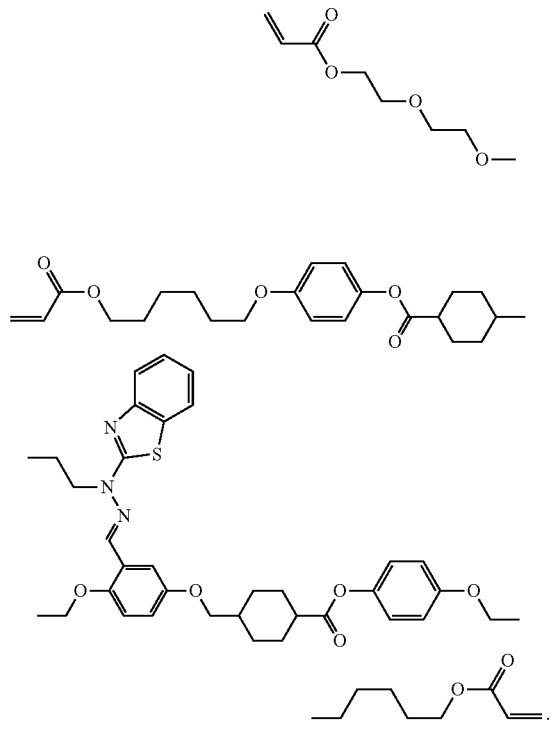

* * * * *